(12) United States Patent
Le Hir de Fallois et al.

(10) Patent No.: US 9,339,033 B2
(45) Date of Patent: *May 17, 2016

(54) 1-ARYL-5-ALKYL PYRAZOLE DERIVATIVE COMPOUNDS, PROCESSES OF MAKING AND METHODS OF USING THEREOF

(71) Applicant: MERIAL, INC., Duluth, GA (US)

(72) Inventors: Loic Patrick Le Hir de Fallois, Atlanta, GA (US); Hyoung Ik Lee, Cary, NC (US); Philip Reid Timmons, Durham, NC (US); William Glenn Cawthorne, Jr., Henderson, NC (US); Adalberto Perez de Leon, Wake Forest, NC (US)

(73) Assignee: MERIAL, INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/325,761

(22) Filed: Jul. 8, 2014

(65) Prior Publication Data

US 2015/0133506 A1 May 14, 2015

Related U.S. Application Data

(63) Continuation of application No. 13/894,601, filed on May 15, 2013, now Pat. No. 8,785,372, which is a continuation of application No. 12/814,289, filed on Jun. 11, 2010, now Pat. No. 8,445,519, which is a continuation of application No. 11/825,050, filed on Jul. 3, 2007, now Pat. No. 7,759,381.

(51) Int. Cl.

| | |
|---|---|
| A01N 43/56 | (2006.01) |
| C07D 401/04 | (2006.01) |
| C07D 231/18 | (2006.01) |
| A01N 47/02 | (2006.01) |
| A61K 31/415 | (2006.01) |
| A61K 31/4439 | (2006.01) |
| A61K 45/06 | (2006.01) |
| A01N 25/02 | (2006.01) |

(52) U.S. Cl.
CPC ............... *A01N 43/56* (2013.01); *A01N 25/02* (2013.01); *A01N 47/02* (2013.01); *A61K 31/415* (2013.01); *A61K 31/4439* (2013.01); *A61K 45/06* (2013.01); *C07D 231/18* (2013.01); *C07D 401/04* (2013.01)

(58) Field of Classification Search
None
See application file for complete search history.

(56) References Cited

U.S. PATENT DOCUMENTS 7,759,381 B2 * 7/2010 Lee et al. .................. 514/406
8,785,372 B2 * 7/2014 Lee et al. .................. 514/1.1

* cited by examiner

*Primary Examiner* — Kamal Saeed
(74) *Attorney, Agent, or Firm* — Judy Jarecki-Black; Peter Dolan; Merial, Inc.

(57) ABSTRACT

Provided are 1-aryl-5-alkyl pyrazole compounds, of formula (I):

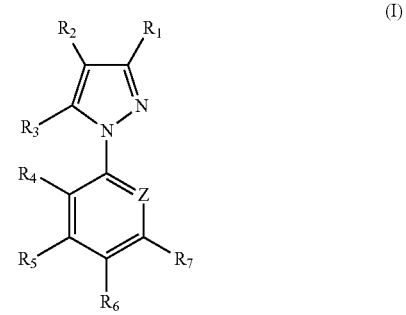

wherein: $R_1$ is hydrogen, cyano, halogen, $R_8$, formyl, —C(O)$R_8$, —C(O)O$R_8$, —C(O)N$R_9R_{10}$, or —C(S)NH$_2$; $R_2$ is $R_8$ or —S(O)$_m R_{11}$; $R_3$ is methyl, ethyl or $C_1$-$C_4$ haloalkyl; $R_4$, $R_5$ and $R_7$ are independently hydrogen, halogen, alkyl, haloalkyl, cyano or nitro; $R_6$ is halogen, alkyl, haloalkyl, alkoxy, haloalkyloxy, cyano, nitro, —C(O)$R_{12}$, —S(O)$_n R_{12}$ or $SF_5$; Z is a nitrogen atom or C—$R_{13}$; $R_8$ is alkyl, haloalkyl, cycloalkyl or halocycloalkyl; $R_9$ is hydrogen, alkyl, haloalkyl or alkoxy; $R_{10}$ is hydrogen, alkyl, haloalkyl or alkoxy; $R_{11}$ is alkyl, haloalkyl, alkenyl, haloalkenyl, alkynyl, haloalkynyl or cycloalkyl; $R_{12}$ is alkyl or haloalkyl; $R_{13}$ is hydrogen, halogen, cyano, nitro, alkyl, haloalkyl, alkoxy or haloalkoxy; m is 0, 1 or 2; and n is 0, 1 or 2; or a salt thereof, the method of making compounds of formula (I) and the use of these compounds against ectoparasites, endoparasites and pests.

20 Claims, No Drawings

1-ARYL-5-ALKYL PYRAZOLE DERIVATIVE COMPOUNDS, PROCESSES OF MAKING AND METHODS OF USING THEREOF

INCORPORATION BY REFERENCE

This application is a continuation of, and claims benefit of, U.S. patent application Ser. No. 13/894,601, filed May 15, 2013, now U.S. Pat. No. 8,785,372, which is a continuation of, and claims benefit of, U.S. patent application Ser. No. 12/814,289, filed Jun. 11, 2010, now U.S. Pat. No. 8,445,519, which claims benefit of, U.S. patent application Ser. No. 11/825,050, filed Jul. 3, 2007, now U.S. Pat. No. 7,759,381, which claims the benefit of U.S. Provisional Application Ser. No. 60/818,585, filed Jul. 5, 2006 and Ser. No. 60/925,913 filed Apr. 24, 2007, which are incorporated herein by reference in their entirely.

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to 1-aryl-5-alkyl pyrazole compounds, of general formula (I):

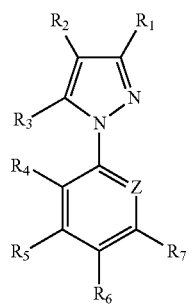

wherein:
$R_1$, $R_2$, $R_3$, $R_4$, $R_5$, $R_6$, $R_7$ and p are as defined below; or a salt thereof and the use of these compounds against ectoparasites such as insects, arthropods and acarina.

BACKGROUND OF THE INVENTION

Animals such as mammals and birds are often susceptible to parasite infestations. These parasites may be ectoparasites, such as insects, and endoparasites such as filariae and worms.

Domesticated animals, such as cats and dogs, are often infested with one or more of the following ectoparasites:
  fleas (*Ctenocephalides felis, Ctenocephalides* sp. and the like),
  ticks (*Rhipicephalus* sp., *Ixodes* sp., *Dermacentor* sp., *Amblyomma* sp. and the like),
  mites (*Demodex* sp., *Sarcoptes* sp., *Otodectes* sp. and the like),
  lice (*Trichodectes* sp., *Cheyletiella* sp., *Linognathus* sp., and the like), and
  flies (*Hematobia* sp., *Musca* sp., *Stomoxys* sp., *Dermatobia* sp., *Cochliomyia* sp., mosquitoes (family Culicidae) and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and may also transmit pathogens to humans.

Similarly, ticks are also harmful to the physical and psychological health of the animal or human. However, the most serious problem associated with ticks is that they are the vector of pathogenic agents, which cause diseases in both humans and animals Major diseases which are caused by ticks include borreliosis (Lyme disease caused by *Borrelia burgdorferi*), babesiosis (or piroplasmosis caused by *Babesia* sp.) and rickettsiosis (also known as Rocky Mountain spotted fever). Ticks also release toxins which cause inflammation or paralysis in the host. Occasionally, these toxins are fatal to the host, such as in the case of the Australian paralysis tick, *Ixodes holocyclus*.

Moreover, mites and lice are particularly difficult to combat since there are very few active substances which act on these parasites and they require frequent treatment.

Likewise, farm animals are also susceptible to parasite infestations. For example, cattle are affected by a large number of parasites. Likewise, arthropod pests, such as fleas, lice and ticks, and mites infest poultry. A parasite that is very prevalent among farm animals is the tick genus *Boophilus*, especially those of the species *microplus* (cattle tick), *decoloratus* and *anulatus*. Ticks, such as *Boophilus microplus*, are particularly difficult to control because they live in the pasture where the farm animals graze. Other important parasites of cattle and sheep are listed as follows in order of decreasing importance:
(a) myiases such as *Dermatobia hominis* (known as Berne in Brazil), Hyooderma, and *Cochlyomia hominivorax* (greenbottle); sheep myiases such as *Lucilia sericata, Lucilia cuprina* (known as blowfly strike in Australia, New Zealand and South Africa). These are flies whose larva constitutes the animal parasite;
(b) flies proper, namely those whose adult constitutes the parasite, such as *Haematobia irritans* (horn fly);
(c) lice such as *Linognathus vituli* etc.; and
(d) mites such as *Sarcoptes scabiei* and *Psoroptes ovis*.

The compounds of the invention may also be useful against household pests including, but not limited to, cockroach, *Blatella* sp., clothes moth, *Tineola* sp., carpet beetle, *Attagenus* sp. and the housefly *Musca domestica* and against *Solenopsis invicta* (imported fire ants), termites, and the like.

These compounds may further be useful against agricultural pests such as aphids (*Acyrthiosiphon* sp.), locusts, and boll weevils as well as against insect pests that attack stored grains, such as *Tribolium* sp., and against immature stages of insects living on plant tissue.

The above list is not exhaustive and other ectoparasites are well known in the art to be harmful to animals, humans and crops.

Compounds that exhibit a degree of activity against a wide range of ectoparasites including arthropods and insects are known in the art. One such class of compounds is the arylpyrazoles which are referred to, for example, in U.S. Pat. Nos. 5,122,530; 5,246,255; 5,576,429; 5,885,607; 6,010,710; 6,083,519; 6,096,329; 6,685,954; EP 0 234 119 and EP 0 295 117 (U.S. Pat. Nos. 5,232,940; 5,547,974; 5,608,077; 5,714, 191; 5,916,618 and 6,372,774); EP 0 352 944 (U.S. Pat. No. 4,963,575); EP 0 780 378 (U.S. Pat. Nos. 5,817,688; 5,922,885; 5,994,386; 6,124,339; 6,180,798 and 6,395,906); EP 0 846 686 (U.S. Pat. No. 6,069,157); and WO 98/28278.

The arylpyrazoles are known to possess excellent activity against insects, such as fleas and ticks. Fipronil is a specific type of 1-N-aryl pyrazole that is particularly effective against fleas and ticks and is the active ingredient in Frontline® and Frontline Plus®. Fipronil has the following chemical structure:

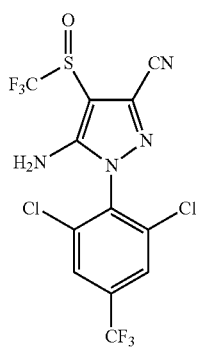 [SMILES: N#Cc1nn(-c2c(Cl)cc(C(F)(F)F)cc2Cl)c(N)c1S(=O)C(F)(F)F]

However, ectoparasiticidal agents can vary in their effectiveness to a particular parasite as well as vary in their cost of production. Moreover, the results of ectoparasiticidal agents may not always be satisfactory because of, for example, the development of resistance by the parasite to the therapeutic agent, as is the case, for example, with carbamates, organophosphorus compounds and pyrethroids.

It is known from the literature that hydrazines may react with 1,3-dicarbonyl compounds to form pyrazoles. For example, U.S. Pat. No. 6,750,230 refers to the synthesis of pyrazoles unsubstituted at the one position or substituted by an alkylene group from 1,3-diketones. WO 01/32663 refers to the synthesis of pyrazolecarboxylic acid tricyclic compounds. WO 03/057674 refers to the synthesis of 4-sulfide/sulfoxidepyrazoles bearing a substituted alkyl group at the 1-position, which may be prepared from the reaction of a 2-thio-1,3-diketone with a hydrazine (see page 24, Reaction Scheme 1). However, there appeared to be no examples where this 2-thio-1,3-diketone derivative was made directly by reacting a sulfenyl halide reagent with 1,3-diketone compounds.

WO 02/058690 and US 2004/0876627 refer to the synthesis of pyrazoles bearing a (2,2,2-trifluoro-1-hydroxy-1-(trifluoromethyl)ethyl substituent by reaction between a 1,3-diketone and phenylhydrazine bearing the 1-hydroxy-1-(trifluoromethyl)ethyl substituent (Scheme 4, page 11, US 2004/0876627). The synthesis of a specific compound by this method, 5-methyl-1-[(1-hydroxy-1-(trifluoromethyl)ethyl)phenyl)-1H-pyrazole-3-carboxylic acid ethyl ester is mentioned (US 2004/0876627, pages 23-24, Example 8). However, there appeared to be no examples where a 3,4,5-disubstituted pyrazole is prepared except in the presence of a 5-amino group or when all three substitutions are the same (methyl).

Synthesis of 3-ester-4-unsubstituted pyrazoles is also referred to in US 2005/00020564 (page 10, Scheme 3).

However, a general problem with obtaining pyrazoles by reacting hydrazines with 1,3-dicarbonyl compounds is the difficulty in preparing compounds with regioselectivity, as there is competition in the reaction at the different carbonyl groups of the 1,3-dicarbonyl compound Thus, there is still a need in the art for more effective and rapidly acting antiparasitic composition for the treatment and protection of animals, e.g. mammals, fish and birds, from a wide range of parasites. There is a need in the art for an antiparasitic formulation which is easy to use on any type of domestic animal, irrespective of its size and the nature of its coat and which do not need to be sprinkled over the entire body of the mammal, fish or bird. Further, the formulation should be effective for a long period of time thereby reducing the number of times it has to be applied.

Citation or identification of any document in this application is not an admission that such document is available as prior art to the present invention.

OBJECTS AND SUMMARY OF THE INVENTION

The invention provides, and it is an object of the invention to provide, novel compounds, compositions and uses thereof for the treatment or prophylaxis of parasites of animals (either wild or domesticated), e.g., livestock and companion animals such as cats, dogs, horses, chickens, sheep, goats, pigs, turkeys and cattle, with the aim of ridding these hosts of parasites commonly encountered by such animals.

Accordingly, it is an object of the invention to not encompass within the invention any previously known compounds, compositions, and uses such that applicant(s) reserve the right and hereby disclose a disclaimer of any previously known compounds, compositions and uses.

The invention also provides for effective and long lasting destruction of ectoparasites, such as fleas, ticks, mites, mosquitoes, flies and lice. The invention may also be effective against endoparasites, cestodes, nematodes, such as filariae, and roundworms of the digestive tract of animals and humans.

The 1-aryl-5-alkyl pyrazole compounds of the invention, alone or in combination, are able to provide superior protection against ectoparasites which may include speed of efficacy, long lasting efficacy (e.g. for a period of at least one month) and enhanced selectivity.

One aspect of the invention is to provide a 1-aryl-5-alkyl pyrazole compound of the formula (I):

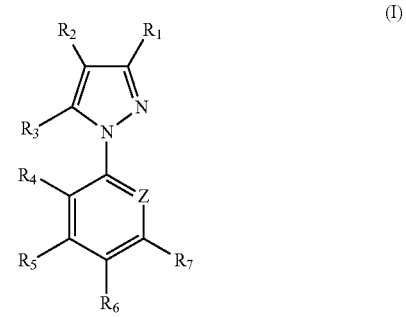

wherein:
$R_1$ is hydrogen, cyano, halogen, $R_8$, formyl, —C(O)$R_8$, —C(O)O$R_8$, —C(O)NR$_9$R$_{10}$, or —C(S)NH$_2$;
$R_2$ is $R_8$ or —S(O)$_m$R$_{11}$;
$R_3$ is methyl, ethyl or $C_1$-$C_4$ haloalkyl;
$R_4$, $R_5$ and $R_7$ are independently hydrogen, halogen, alkyl, haloalkyl, cyano or nitro;

$R_6$ is halogen, alkyl, haloalkyl, alkoxy, haloalkyloxy, cyano, nitro, —C(O)$R_{12}$, —S(O)$_n R_{12}$ or $SF_5$;

Z is a nitrogen atom or C—$R_{13}$;

$R_8$ is alkyl, haloalkyl, cycloalkyl or halocycloalkyl;

$R_9$ is hydrogen, alkyl, haloalkyl or alkoxy;

$R_{10}$ is hydrogen, alkyl, haloalkyl or alkoxy;

$R_{11}$ is alkyl, haloalkyl, alkenyl, haloalkenyl, alkynyl, haloalkynyl or cycloalkyl;

$R_{12}$ is alkyl or haloalkyl;

$R_{13}$ is hydrogen, halogen, cyano, nitro, alkyl, haloalkyl, alkoxy or haloalkoxy;

m is 0, 1 or 2; and n is 0, 1 or 2; or a salt thereof.

A second aspect of the invention, provides for a process for the preparation of a compound of formula (I), or a pharmaceutically, veterinarily or agriculturally acceptable salt thereof, or a pharmaceutically, veterinarily or agriculturally acceptable solvate (including hydrate) of either entity.

A third aspect of the present invention is to provide compositions for treatment of animals against ectoparasites, wherein the compositions comprise the compounds of the invention and an acceptable carrier.

A fourth aspect of the invention is to provide pesticidal methods of use of the 1-aryl-5-alkyl pyrazole compounds/compositions of the invention against ectoparasites (e.g. arthropods, acarina and insects), in veterinary medicine or livestock husbandry, in public health, or in agricultural or horticultural crops.

A fifth aspect of the present invention is to provide compounds with high activity and improved safety to the user and the environment, which are obtained by optimization of chemical, physical and biological properties such as solubility, melting point, stability, electronic and steric parameters, and the like.

A sixth aspect of the present invention is to provide a method for preventing or interrupting the transmission of parasite-borne diseases from an actual or putative amplifying or incipient host, such as an animal or bird (wild or domesticated) or human, to a second actual or putative amplifying or incipient host, such as an animal, bird or human, using a composition comprising the 1-aryl-5-alkyl pyrazole compounds of the invention.

A seventh aspect of the present invention is to provide novel intermediate compounds for the production of the compounds of formula (I).

Finally, it has been found that the novel compounds of the formula (I) have strongly pronounced biological properties and are suitable especially for controlling animal pests, in particular insects, arachnids and nematodes encountered in agriculture, in forests, in the protection of stored products and in the protection of materials, and also in the hygiene sector.

For the purposes of this application, unless otherwise stated in the specification, the following terms have the definitions cited below:

(1) Alkyl refers to both straight and branched carbon chains; references to individual alkyl groups are specific for the straight chain (e.g. butyl=n-butyl). In one embodiment of alkyl, the number of carbons atoms is 1-20, in another embodiment of alkyl, the number of carbon atoms is 1-8 carbon atoms and in yet another embodiment of alkyl, the number of carbon atoms is 1-4 carbon atoms. Other ranges of carbon numbers are also contemplated depending on the location of the alkyl moiety on the molecule;

(2) Alkenyl refers to both straight and branched carbon chains which have at least one carbon-carbon double bond. In one embodiment of alkenyl, the number of double bonds is 1-3; in another embodiment of alkenyl, the number of double bonds is one. In one embodiment of alkenyl, the number of carbons atoms is 2-20, in another embodiment of alkenyl, the number of carbon atoms is 2-8 and in yet another embodiment of alkenyl, the number of carbon atoms is 2-4. Other ranges of carbon-carbon double bonds and carbon numbers are also contemplated depending on the location of the alkenyl moiety on the molecule;

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in another embodiment of alkynyl, the number of carbon atoms is 2-8 and in yet another embodiment of alkynyl, the number of carbon atoms is 2-4. Other ranges of carbon-carbon double bonds and carbon numbers are also contemplated depending on the location of the alkenyl moiety on the molecule;

(4) Aryl refers to a $C_6$-$C_{10}$ aromatic ring structure. In one embodiment of aryl, the moiety is phenyl, naphthyl, tetrahydronaphthyl, phenylcyclopropyl and indanyl; in another embodiment of aryl, the moiety is phenyl.

(5) Alkoxy refers to —O-alkyl, wherein alkyl is as defined in (1);

(6) Alkanoyl refers to formyl (—C(=O)H) and —C(=O)-alkyl, wherein alkyl is as defined in (1);

(7) Alkanoyloxy refers to —O—C(=O)-alkyl, wherein alkanoyl is as defined in (6);

(8) Alkanoylamino refers to —$NH_2$—C(=O)-alkyl, wherein alkanoyl is as defined in (6) and the amino ($NH_2$) moiety can be substituted by alkyl as defined in (1);

(9) Aminocarbonyl refers to —$NH_2$—C(=O), wherein the amino ($NH_2$) moiety can be substituted by alkyl as defined in (1);

(10) Alkoxycarbonyl refers to —C(=O)—O-alkyl, wherein alkoxy is as defined in (5);

(11) Alkenoyl refers to —C(=O)-alkenyl, wherein alkenyl is as defined in (2);

(12) Alkynoyl refers to —C(=O)-alkynyl, wherein alkynyl is as defined in (3);

(13) Aroyl refers to —C(=O)-aryl, wherein aryl is as defined above;

(14) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(15) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

(16) Heterocycle, heterocyclic or heterocyclo refer to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means a 1-aryl-5-alkyl pyrazole compound of the invention It is also noted that this disclosure and in the claims and/or paragraphs, the term "1-aryl-5-alkyl pyrazole compound" as used to describe the invention is intended to include all stereoisomers and crystalline forms (which includes hydrated forms, polymorphic forms and amorphous forms with up to 15% by weight crystalline structure) thereof.

It is noted that in this disclosure and in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

It is further noted that the invention does not intend to encompass within the scope of the invention any previously disclosed compound, product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned, including without limitation U.S. Pat. Nos. 5,122,530; 5,246,255; 5,576,429; 5,885,607; 6,010,710; 6,083,519; 6,096,329; 6,685,954; EP 0 234 119 and EP 0 295 117 (eq. to U.S. Pat. Nos. 5,232,940; 5,547,974; 5,608,077; 5,714,191; 5,916,618 and 6,372,774); EP 0 352 944 (eq. to U.S. Pat. No. 4,963,575); EP 0 780 378 (eq. to U.S. Pat. Nos. 5,817,688; 5,922,885; 5,994,386; 6,124,339; 6,180,798 and 6,395,906); EP 0 846 686 (eq. to U.S. Pat. No. 6,069,157); and WO 98/28278; and, applicant(s) explicitly reserve the right to introduce into any claim a disclaimer as to any previously disclosed compound, product, process of making the product or method of using the product. Specifically, the compounds of formula (I) and (Ia) are not intended to encompass fipronil or previously disclosed derivatives of fipronil.

These and other embodiments are disclosed or are apparent from and encompassed by, the following Detailed Description.

DETAILED DESCRIPTION

A first aspect of the invention provides a 1-aryl-5-alkyl pyrazole compound of formula (I):

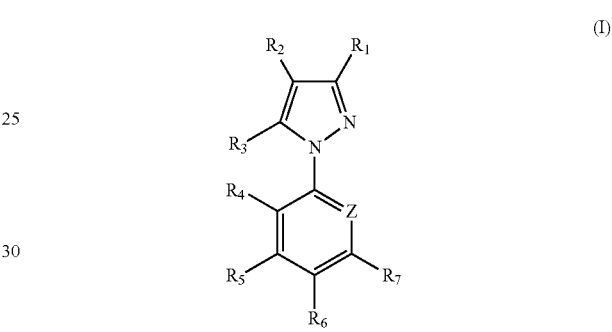

wherein:
$R_1$ is hydrogen, cyano, halogen, $R_8$, formyl, —C(O)$R_8$, —C(O)O$R_8$, —C(O)N$R_9R_{10}$, or —C(S)NH$_2$;
$R_2$ is $R_8$ or —S(O)$_mR_{11}$;
$R_3$ is methyl, ethyl or $C_1$-$C_4$ haloalkyl;
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —C(O)$R_{12}$, —S(O)$_nR_{12}$ or SF$_5$;
Z is a nitrogen atom or C—$R_{13}$;
$R_8$ is alkyl, haloalkyl, cycloalkyl or halocycloalkyl;
$R_9$ is hydrogen, alkyl, haloalkyl or alkoxy;
$R_{10}$ is hydrogen, alkyl, haloalkyl or alkoxy;
$R_{11}$ is alkyl, haloalkyl, alkenyl, haloalkenyl, alkynyl, haloalkynyl or cycloalkyl;
$R_{12}$ is alkyl or haloalkyl;
$R_{13}$ is hydrogen, halogen, cyano, nitro, alkyl, haloalkyl, alkoxy or haloalkoxy;
m is 0, 1 or 2; and
n is 0, 1 or 2; or
a salt thereof.

A second aspect of the invention provides a 1-aryl-5-alkyl pyrazole compound of formula (I) wherein:
$R_3$ is methyl or ethyl; and
$R_1$, $R_2$, $R_4$, $R_5$, $R_6$, $R_7$, $R_8$, $R_9$, $R_{10}$, $R_{11}$, $R_{12}$, $R_{13}$, m and n are as defined above; or
a salt thereof.

A third aspect of the invention provides a 1-aryl-5-alkyl pyrazole compound of formula (I) wherein:
$R_3$ is $C_1$-$C_4$ haloalkyl; and
$R_1$, $R_2$, $R_4$, $R_5$, $R_6$, $R_7$, $R_8$, $R_9$, $R_{10}$, $R_{11}$, $R_{12}$, $R_{13}$, m and n are as defined above; or
a salt thereof.

Another embodiment of the first aspect of the invention provides a 1-aryl-5-alkyl pyrazole compound of formula (I): wherein:
$R_1$ is hydrogen, cyano, halogen, $R_8$, formyl, —C(O)$R_8$, —C(O)O$R_8$, —C(O)N$R_9R_{10}$, or —C(S)NH$_2$;
$R_2$ is $R_8$ or —S(O)$_m R_{11}$,
$R_3$ is a methyl, ethyl or $C_1$-$C_4$ haloalkyl,
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —C(O)$R_{12}$, —S(O)$_n R_{12}$ or SF$_5$;
Z is a nitrogen atom or C—$R_{13}$;
$R_8$ is alkyl, haloalkyl, cycloalkyl or halocycloalkyl;
$R_9$ is hydrogen, alkyl, haloalkyl or alkoxy;
$R_{10}$ is hydrogen, alkyl, haloalkyl or alkoxy;
$R_{11}$ is alkyl, haloalkyl, alkenyl, haloalkenyl, alkynyl, haloalkynyl or cycloalkyl;
$R_{12}$ is alkyl or haloalkyl;
$R_{13}$ is hydrogen, halogen, cyano, nitro, alkyl, haloalkyl, alkoxy or haloalkoxy;
m is 0, 1 or 2; and
n is 0, 1 or 2; or
a salt thereof.

Another embodiment of the first aspect of the invention provides a 1-aryl-5-alkyl pyrazole compound of formula (I) is:
$R_1$ is hydrogen, cyano, halogen, $R_8$, formyl, —C(O)$R_8$, —C(O)O$R_8$, —C(O)N$R_9R_{10}$, or —C(S)NH$_2$;
$R_2$ is alkyl, haloalkyl or —S(O)$_m R_{11}$;
$R_3$ is a methyl, ethyl or $C_1$-$C_4$ haloalkyl,
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —C(O)$R_{12}$, —S(O)$_n R_{12}$ or —SF$_5$;
Z is a nitrogen atom or C—$R_{13}$;
$R_8$ is alkyl, haloalkyl, cycloalkyl or halocycloalkyl;
$R_9$ is hydrogen, alkyl, haloalkyl or alkoxy;
$R_{10}$ is hydrogen, alkyl, haloalkyl or alkoxy;
$R_{11}$ is alkyl, haloalkyl, alkenyl, haloalkenyl, alkynyl, haloalkynyl or cycloalkyl;
$R_{12}$ is alkyl or haloalkyl;
$R_{13}$ is hydrogen, halogen, cyano, nitro, alkyl, haloalkyl, alkoxy or haloalkoxy;
m is 0, 1 or 2; and
n is 0, 1 or 2; or
a salt thereof.

Another embodiment of the first aspect of the invention provides a 1-aryl-5-alkyl pyrazoles of formula (I) wherein:
$R_1$ is hydrogen, cyano, halogen, $R_8$, formyl, —C(O)$R_8$, —C(O)O$R_8$, —C(O)N$R_9R_{10}$, or —C(S)NH$_2$;
$R_2$ is $C_1$-$C_4$ alkyl, $C_1$-$C_4$ haloalkyl, or —S(O)$_m R_{11}$, $R_3$ is a methyl, ethyl or $C_1$-$C_4$ haloalkyl,
$R_4$, $R_5$ and $R_7$ are independently hydrogen, halogen, $C_1$-$C_4$ alkyl, $C_1$-$C_4$ haloalkyl, cyano or nitro;
$R_6$ is halogen, $C_1$-$C_4$ alkyl, $C_1$-$C_4$ haloalkyl, $C_1$-$C_4$ alkoxy, $C_1$-$C_4$ haloalkyloxy, cyano, nitro, —C(O)$R_{12}$, —S(O)$_n R_{12}$ or SF$_5$;
Z is a nitrogen atom or C—$R_{13}$;
$R_8$ is $C_1$-$C_4$ alkyl, $C_1$-$C_4$ haloalkyl or cycloalkyl optionally substituted with one or more halogens;
$R_9$ is hydrogen, $C_1$-$C_4$ alkyl, $C_1$-$C_4$ haloalkyl or $C_1$-$C_4$ alkoxy;
$R_{10}$ is hydrogen, $C_1$-$C_4$ alkyl, $C_1$-$C_4$ haloalkyl or $C_1$-$C_4$ alkoxy;
$R_{11}$ is $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl or cycloalkyl;
$R_{12}$ is $C_1$-$C_4$ alkyl or $C_1$-$C_4$ haloalkyl;
$R_{13}$ is hydrogen, halogen, cyano, nitro, $C_1$-$C_4$ alkyl, $C_1$-$C_4$ haloalkyl, $C_1$-$C_4$ alkoxy or $C_1$-$C_4$ haloalkoxy;
m is 0, 1 or 2; and
n is 0, 1 or 2; or
a salt thereof.

Another embodiment of the first aspect of the invention provides a 1-aryl-5-alkyl pyrazoles of formula (I) wherein:
$R_1$ is hydrogen, cyano, fluoro, chloro, $R_8$, formyl, —C(O)$R_8$, —C(O)O$R_8$, —C(O)N$R_9R_{10}$, or —C(S)NH$_2$;
$R_2$ is $C_1$-$C_2$ alkyl, $C_1$-$C_2$ fluoroalkyl, $C_1$-$C_2$ chloroalkyl or —S(O)$_m R_{11}$;
$R_3$ is a methyl, ethyl optionally substituted with one to three halogens;
$R_4$, $R_5$ and $R_7$ are independently selected from the group consisting of hydrogen, fluoro, chloro, $C_1$-$C_2$ alkyl, $C_1$-$C_2$ fluoroalkyl, $C_1$-$C_2$ chloroalkyl, cyano and nitro;
$R_6$ is fluoro, chloro, $C_1$-$C_2$ alkyl, $C_1$-$C_2$ fluoroalkyl, $C_1$-$C_2$ chloroalkyl, $C_1$-$C_2$ alkoxy, $C_1$-$C_2$ fluoroalkyloxy, $C_1$-$C_2$ chloroalkyloxy, cyano, nitro, —C(O)$R_{12}$, —S(O)$_n R_{12}$ or SF$_5$;
Z is a nitrogen atom or C—$R_{13}$;
$R_8$ is $C_1$-$C_2$ alkyl, $C_1$-$C_2$ fluoroalkyl or $C_1$-$C_2$ chloroalkyl;
$R_9$ is hydrogen, $C_1$-$C_2$ alkyl, $C_1$-$C_2$ fluoroalkyl, $C_1$-$C_2$ chloroalkyl or $C_1$-$C_2$ alkoxy;
$R_{10}$ is hydrogen, $C_1$-$C_2$ alkyl, $C_1$-$C_2$ fluoroalkyl, $C_1$-$C_2$ chloroalkyl or $C_1$-$C_2$ alkoxy;
$R_{11}$ is $C_1$-$C_2$ alkyl, $C_1$-$C_2$ fluoroalkyl, $C_1$-$C_2$ chloroalkyl, $C_2$-$C_4$ alkenyl, $C_2$-$C_4$ fluoroalkenyl, $C_2$-$C_4$ chloroalkenyl, $C_2$-$C_4$ alkynyl, $C_2$-$C_4$ fluoroalkynyl or $C_2$-$C_4$ chloroalkynyl;
$R_{12}$ is $C_1$-$C_2$ alkyl, $C_1$-$C_2$ fluoroalkyl or $C_1$-$C_2$ chloroalkyl;
$R_{13}$ is hydrogen, fluoro, chloro, cyano, nitro, $C_1$-$C_2$ alkyl, $C_1$-$C_2$ fluoroalkyl, $C_1$-$C_2$ chloroalkyl, $C_1$-$C_2$ alkoxy, $C_1$-$C_2$ fluoroalkoxy or $C_1$-$C_2$ chloroalkoxy;
m is 0, 1 or 2; and
n is 0, 1 or 2; or
a salt thereof.

Another embodiment of the first aspect of the invention, wherein Z is C—$R_{13}$, provides a 1-aryl-5-alkyl pyrazoles of formula (I) wherein:
$R_1$ is cyano;
$R_2$ is —S(O)$_m R_{11}$;
$R_3$ is a methyl, ethyl optionally substituted with one to three halogens;
$R_4$, $R_5$, $R_7$ are independently hydrogen or halogen;
$R_6$ is $C_1$-$C_4$ haloalkyl, $C_1$-$C_4$ haloalkoxy or SF$_5$;
$R_{11}$ is $C_1$-$C_4$ haloalkyl;
$R_{13}$ is $C_1$-$C_4$ alkyl optionally substituted with one or more fluoro or chloro or halogen; and
m is 0, 1 or 2; or
a salt thereof.

Another embodiment of the first aspect of the invention, wherein Z is C—$R_{13}$, provides a 1-aryl-5-alkyl pyrazoles of formula (I) wherein:
$R_1$ is cyano;
$R_2$ is —S(O)$_m R_{11}$;
$R_3$ is a methyl, ethyl, —CH$_2$F or —CHF$_2$;
$R_4$, $R_5$, and $R_7$ are independently hydrogen or halogen;
$R_6$ is —CF$_3$, —OCF$_3$ or —SF$_5$;
$R_{11}$ is —CF$_3$, —CClF$_2$ or —CCl$_2$F;
$R_{13}$ is methyl, chloro or fluoro; and
m is 0, 1 or 2; or
a salt thereof.

Another embodiment of the first aspect of the invention wherein Z is C—$R_{13}$, provides a 1-aryl-5-alkyl pyrazoles of formula (I) wherein:

$R_1$ is cyano;
$R_2$ is —S(O)$_m$R$_{11}$;
$R_3$ is a methyl, ethyl, —CH$_2$F or —CHF$_2$;
$R_4$ is hydrogen, Cl or F;
$R_5$ and $R_7$ are both hydrogen;
$R_6$ is —CF$_3$, —OCF$_3$ or —SF$_5$;
$R_{11}$ is —CF$_3$, —CClF$_2$ or —CCl$_2$F;
$R_{13}$ is methyl, chloro or fluoro; and
m is 0, 1 or 2; or
a salt thereof.

Another embodiment of the second aspect of the invention provides a 1-aryl-5-alkyl pyrazole compound of formula (I): wherein:
$R_1$ is hydrogen, cyano, halogen, $R_8$, formyl, —C(O)R$_8$, —C(O)OR$_8$, —C(O)NR$_9$R$_{10}$, or —C(S)NH$_2$;
$R_2$ is $R_8$ or —S(O)$_m$R$_{11}$,
$R_3$ is a methyl or ethyl,
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —C(O)R$_{12}$, —S(O)$_n$R$_{12}$ or SF$_5$;
Z is a nitrogen atom or C—R$_{13}$;
$R_8$ is alkyl, haloalkyl, cycloalkyl or halocycloalkyl;
$R_9$ is hydrogen, alkyl, haloalkyl or alkoxy;
$R_{10}$ is hydrogen, alkyl, haloalkyl or alkoxy;
$R_{11}$ is alkyl, haloalkyl, alkenyl, haloalkenyl, alkynyl, haloalkynyl or cycloalkyl;
$R_{12}$ is alkyl or haloalkyl;
$R_{13}$ is hydrogen, halogen, cyano, nitro, alkyl, haloalkyl, alkoxy or haloalkoxy;
m is 0, 1 or 2; and
n is 0, 1 or 2; or
a salt thereof.

Another embodiment of the second aspect of the invention provides a 1-aryl-5-alkyl pyrazole compound of formula (I) is:
$R_1$ is hydrogen, cyano, halogen, $R_8$, formyl, —C(O)R$_8$, —C(O)OR$_8$, —C(O)NR$_9$R$_{10}$, or —C(S)NH$_2$;
$R_2$ is alkyl, haloalkyl or —S(O)$_m$R$_{11}$,
$R_3$ is a methyl or ethyl,
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —C(O)R$_{12}$, —S(O)$_n$R$_{12}$ or —SF$_5$;
Z is a nitrogen atom or C—R$_{13}$;
$R_8$ is alkyl, haloalkyl, cycloalkyl or halocycloalkyl;
$R_9$ is hydrogen, alkyl, haloalkyl or alkoxy;
$R_{10}$ is hydrogen, alkyl, haloalkyl or alkoxy;
$R_{11}$ is alkyl, haloalkyl, alkenyl, haloalkenyl, alkynyl, haloalkynyl or cycloalkyl;
$R_{12}$ is alkyl or haloalkyl;
$R_{13}$ is hydrogen, halogen, cyano, nitro, alkyl, haloalkyl, alkoxy or haloalkoxy;
m is 0, 1 or 2; and
n is 0, 1 or 2; or
a salt thereof.

Another embodiment of the second aspect of the invention provides a 1-aryl-5-alkyl pyrazoles of formula (I) wherein:
$R_1$ is hydrogen, cyano, halogen, $R_8$, formyl, —C(O)R$_8$, —C(O)OR$_8$, —C(O)NR$_9$R$_{10}$, or —C(S)NH$_2$;
$R_2$ is C$_1$-C$_4$ alkyl, C$_1$-C$_4$ haloalkyl or —S(O)$_m$R$_{11}$;
$R_3$ is methyl or ethyl,
$R_4$, $R_5$ and $R_7$ are independently hydrogen, halogen, C$_1$-C$_4$ alkyl, C$_1$-C$_4$ haloalkyl, cyano or nitro;
$R_6$ is halogen, C$_1$-C$_4$ alkyl, C$_1$-C$_4$ haloalkyl, C$_1$-C$_4$ alkoxy, C$_1$-C$_4$ haloalkyloxy, cyano, nitro, —C(O)R$_{12}$, —S(O)$_n$R$_{12}$ or SF$_5$;
Z is a nitrogen atom or C—R$_{13}$;
$R_8$ is C$_1$-C$_4$ alkyl, C$_1$-C$_4$ haloalkyl or cycloalkyl optionally substituted with one or more halogens;
$R_9$ is hydrogen, C$_1$-C$_4$ alkyl, C$_1$-C$_4$ haloalkyl or C$_1$-C$_4$ alkoxy;
$R_{10}$ is hydrogen, C$_1$-C$_4$ alkyl, C$_1$-C$_4$ haloalkyl or C$_1$-C$_4$ alkoxy;
$R_{11}$ is C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_2$-C$_4$ haloalkynyl or cycloalkyl;
$R_{12}$ is C$_1$-C$_4$ alkyl or C$_1$-C$_4$ haloalkyl;
$R_{13}$ is hydrogen, halogen, cyano, nitro, C$_1$-C$_4$ alkyl, C$_1$-C$_4$ haloalkyl, C$_1$-C$_4$ alkoxy or C$_1$-C$_4$ haloalkoxy;
m is 0, 1 or 2; and
n is 0, 1 or 2; or
a salt thereof.

Another embodiment of the second aspect of the invention provides a 1-aryl-5-alkyl pyrazoles of formula (I) wherein:
$R_1$ is hydrogen, cyano, fluoro, chloro, $R_8$, formyl, —C(O)R$_8$, —C(O)OR$_8$, —C(O)NR$_9$R$_{10}$, or —C(S)NH$_2$;
$R_2$ is C$_1$-C$_2$ alkyl, C$_1$-C$_2$ fluoroalkyl, C$_1$-C$_2$ chloroalkyl, or —S(O)$_m$R$_{11}$;
$R_3$ is methyl or ethyl,
$R_4$, $R_5$ and $R_7$ are independently selected from the group consisting of hydrogen, fluoro, chloro, C$_1$-C$_2$ alkyl, C$_1$-C$_2$ fluoroalkyl, C$_1$-C$_2$ chloroalkyl, cyano and nitro;
$R_6$ is fluoro, chloro, C$_1$-C$_2$ alkyl, C$_1$-C$_2$ fluoroalkyl, C$_1$-C$_2$ chloroalkyl, C$_1$-C$_2$ alkoxy, C$_1$-C$_2$ fluoroalkyloxy, C$_1$-C$_2$ chloroalkyloxy, cyano, nitro, —C(O)R$_{12}$, —S(O)$_n$R$_{12}$ or SF$_5$;
Z is a nitrogen atom or C—R$_{13}$;
$R_8$ is C$_1$-C$_2$ alkyl, C$_1$-C$_2$ fluoroalkyl or C$_1$-C$_2$ chloroalkyl;
$R_9$ is hydrogen, C$_1$-C$_2$ alkyl, C$_1$-C$_2$ fluoroalkyl or C$_1$-C$_2$ chloroalkyl;
$R_{10}$ is hydrogen, C$_1$-C$_2$ alkyl, C$_1$-C$_2$ fluoroalkyl or C$_1$-C$_2$ chloroalkyl;
$R_{11}$ is C$_1$-C$_2$ alkyl, C$_1$-C$_2$ fluoroalkyl, C$_1$-C$_2$ chloroalkyl, C$_2$-C$_4$ alkenyl, C$_2$-C$_4$ fluoroalkenyl, C$_2$-C$_4$ chloroalkenyl, C$_2$-C$_4$ alkynyl, C$_2$-C$_4$ fluoroalkynyl or C$_2$-C$_4$ chloroalkynyl;
$R_{12}$ is C$_1$-C$_2$ alkyl, C$_1$-C$_2$ fluoroalkyl or C$_1$-C$_2$ chloroalkyl;
$R_{13}$ is hydrogen, fluoro, chloro, cyano, nitro, C$_1$-C$_2$ alkyl, C$_1$-C$_2$ fluoroalkyl, C$_1$-C$_2$ chloroalkyl C$_1$-C$_2$ alkoxy, C$_1$-C$_2$ fluoroalkoxy or C$_1$-C$_2$ chloroalkoxy;
m is 0, 1 or 2; and
n is 0, 1 or 2; or
a salt thereof.

An embodiment of the second aspect of the invention, wherein Z is C—R$_{13}$, provides a 1-aryl-5-alkyl pyrazoles of formula (I) wherein:
$R_1$ is cyano;
$R_2$ is —S(O)$_m$R$_{11}$;
$R_3$ is methyl or ethyl,
$R_4$, $R_5$, $R_7$ are independently hydrogen or halogen;
$R_6$ is C$_1$-C$_4$ haloalkyl, C$_1$-C$_4$ haloalkoxy or SF$_5$;
$R_{11}$ is C$_1$-C$_4$ haloalkyl;
$R_{13}$ is C$_1$-C$_4$ alkyl optionally substituted with one or more fluoro or chloro or halogen;
and
m is 0, 1 or 2; or
a salt thereof.

Another embodiment of the second aspect of the invention, wherein Z is C—R$_{13}$, provides a 1-aryl-5-alkyl pyrazoles of formula (I) wherein:
$R_1$ is cyano;
$R_2$ is —S(O)$_m$R$_{11}$;
$R_3$ is methyl or ethyl;

$R_4$, $R_5$, and $R_7$ are independently hydrogen or halogen;
$R_6$ is —$CF_3$, —$OCF_3$ or —$SF_5$;
$R_{11}$ is —$CF_3$, —$CClF_2$ or —$CCl_2F$;
$R_{13}$ is methyl, chloro or fluoro; and
m is 0, 1 or 2; or
a salt thereof.

Another embodiment of the second aspect of the invention wherein Z is C—$R_{13}$, provides a 1-aryl-5-alkyl pyrazoles of formula (I) wherein:
$R_1$ is cyano;
$R_2$ is —$S(O)_mR_{11}$;
$R_3$ is methyl or ethyl;
$R_4$ is hydrogen, Cl or F;
$R_5$ and $R_7$ are both hydrogen;
$R_6$ is —$CF_3$, —$OCF_3$ or —$SF_5$;
$R_{11}$ is —$CF_3$, —$CClF_2$ or —$CCl_2F$;
$R_{13}$ is methyl, chloro or fluoro; and
m is 0, 1 or 2; or
a salt thereof.

Another embodiment of the third aspect of the invention provides a 1-aryl-5-alkyl pyrazole compound of formula (I) wherein:
$R_3$ is selected from the group consisting of $C_1$-$C_4$ haloalkyl, $C_1$-$C_4$ alkyl substituted by one to three halogens, $CH_2F$ and $CHF_2$; and
$R_1$, $R_2$, $R_4$, $R_5$, $R_6$, $R_7$, $R_8$, $R_9$, $R_{10}$, $R_{11}$, $R_{12}$, $R_{13}$, m and n are as defined above; or a salt thereof.

Another embodiment of the third aspect of the invention provides a 1-aryl-5-alkyl pyrazole compound of formula (I) wherein:
$R_1$ is hydrogen, cyano, halogen, $R_8$, formyl, —$C(O)R_8$, —$C(O)OR_8$, —$C(O)NR_9R_{10}$, or —$C(S)NH_2$,
$R_2$ is alkyl, haloalkyl or —$S(O)_mR_{11}$,
$R_3$ is a $C_1$-$C_4$ haloalkyl,
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —$C(O)R_{12}$, —$S(O)_nR_{12}$ or —$SF_5$;
Z is a nitrogen atom or C—$R_{13}$;
$R_8$ is alkyl, haloalkyl, cycloalkyl or halocycloalkyl;
$R_9$ is hydrogen, alkyl, haloalkyl or alkoxy;
$R_{10}$ is hydrogen, alkyl, haloalkyl or alkoxy;
$R_{11}$ is alkyl, haloalkyl, alkenyl, haloalkenyl, alkynyl, haloalkynyl or cycloalkyl;
$R_{12}$ is alkyl or haloalkyl;
$R_{13}$ is hydrogen, halogen, cyano, nitro, alkyl, haloalkyl, alkoxy or haloalkoxy;
m is 0, 1 or 2; and
n is 0, 1 or 2; or
a salt thereof.

Another embodiment of the third aspect of the invention provides a 1-aryl-5-alkyl pyrazoles of formula (I) wherein:
$R_1$ is hydrogen, cyano, halogen, $R_8$, formyl, —$C(O)R_8$, —$C(O)OR_8$, —$C(O)NR_9R_{10}$, or —$C(S)NH_2$;
$R_2$ is $C_1$-$C_4$ alkyl, $C_1$-$C_4$ haloalkyl or —$S(O)_mR_{11}$,
$R_3$ is $C_1$-$C_4$ haloalkyl,
$R_4$, $R_5$ and $R_7$ are independently hydrogen, halogen, $C_1$-$C_4$ alkyl, $C_1$-$C_4$ haloalkyl, cyano or nitro;
$R_6$ is halogen, $C_1$-$C_4$ alkyl, $C_1$-$C_4$ haloalkyl, $C_1$-$C_4$ alkoxy, $C_1$-$C_4$ haloalkyloxy, cyano, nitro, —$C(O)R_{12}$, —$S(O)_nR_{12}$ or $SF_5$;
Z is a nitrogen atom or C—$R_{13}$;
$R_8$ is $C_1$-$C_4$ alkyl, $C_1$-$C_4$ haloalkyl or cycloalkyl optionally substituted with one or more halogens;
$R_9$ is hydrogen, $C_1$-$C_4$ alkyl, $C_1$-$C_4$ haloalkyl or $C_1$-$C_4$ alkoxy;
$R_{10}$ is hydrogen, $C_1$-$C_4$ alkyl, $C_1$-$C_4$ haloalkyl or $C_1$-$C_4$ alkoxy;
$R_{11}$ is $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl or cycloalkyl;
$R_{12}$ is $C_1$-$C_4$ alkyl or $C_1$-$C_4$ haloalkyl;
$R_{13}$ is hydrogen, halogen, cyano, nitro, $C_1$-$C_4$ alkyl, $C_1$-$C_4$ haloalkyl, $C_1$-$C_4$ alkoxy or $C_1$-$C_4$ haloalkoxy;
m is 0, 1 or 2; and
n is 0, 1 or 2; or
a salt thereof.

Another embodiment of the third aspect of the invention provides a 1-aryl-5-alkyl pyrazoles of formula (I) wherein:
$R_1$ is hydrogen, cyano, fluoro, chloro, $R_8$, formyl, —$C(O)R_8$, —$C(O)OR_8$, —$C(O)NR_9R_{10}$, or —$C(S)NH_2$;
$R_2$ is $C_1$-$C_2$ alkyl, $C_1$-$C_2$ fluoroalkyl or —$S(O)_mR_{11}$;
$R_3$ is methyl or ethyl substituted with one to three halogens,
$R_4$, $R_5$ and $R_7$ are independently selected from the group consisting of hydrogen, fluoro, chloro, $C_1$-$C_2$ alkyl, $C_1$-$C_2$ fluoroalkyl, $C_1$-$C_2$ chloroalkyl, cyano and nitro;
$R_6$ is fluoro, chloro, $C_1$-$C_2$ alkyl, $C_1$-$C_2$ fluoroalkyl, $C_1$-$C_2$ chloroalkyl, $C_1$-$C_2$ alkoxy, $C_1$-$C_2$ fluoroalkyloxy, $C_1$-$C_2$ chloroalkyloxy, cyano, nitro, —$C(O)R_{12}$, —$S(O)_nR_{12}$ or $SF_5$;
Z is a nitrogen atom or C—$R_{13}$;
$R_8$ is $C_1$-$C_2$ alkyl, $C_1$-$C_2$ fluoroalkyl or $C_1$-$C_2$ chloroalkyl;
$R_9$ is hydrogen, $C_1$-$C_2$ alkyl, $C_1$-$C_2$ fluoroalkyl or $C_1$-$C_2$ chloroalkyl;
$R_{10}$ is hydrogen, $C_1$-$C_2$ alkyl, $C_1$-$C_2$ fluoroalkyl or $C_1$-$C_2$ chloroalkyl;
$R_{11}$ is $C_1$-$C_2$ alkyl, $C_1$-$C_2$ fluoroalkyl, $C_1$-$C_2$ chloroalkyl, $C_2$-$C_4$ alkenyl, $C_2$-$C_4$ fluoroalkenyl, $C_2$-$C_4$ chloroalkenyl, $C_2$-$C_4$ alkynyl, $C_2$-$C_4$ fluoroalkynyl or $C_2$-$C_4$ chloroalkynyl;
$R_{12}$ is $C_1$-$C_2$ alkyl, $C_1$-$C_2$ fluoroalkyl or $C_1$-$C_2$ chloroalkyl;
$R_{13}$ is hydrogen, fluoro, chloro, cyano, nitro, $C_1$-$C_2$ alkyl, $C_1$-$C_2$ fluoroalkyl, $C_1$-$C_2$ chloroalkyl $C_1$-$C_2$ alkoxy, $C_1$-$C_2$ fluoroalkoxy or $C_1$-$C_2$ chloroalkoxy;
m is 0, 1 or 2; and
n is 0, 1 or 2; or
a salt thereof.

Another embodiment of the third aspect of the invention, wherein Z is C—$R_{13}$, provides a 1-aryl-5-alkyl pyrazoles of formula (I) wherein:
$R_1$ is cyano;
$R_2$ is —$S(O)_mR_{11}$;
$R_3$ is methyl or ethyl substituted with one to three halogens,
$R_4$, $R_5$, $R_7$ are independently hydrogen or halogen;
$R_6$ is $C_1$-$C_4$ haloalkyl, $C_1$-$C_4$ haloalkoxy or $SF_5$;
$R_{11}$ is $C_1$-$C_4$ haloalkyl;
$R_{13}$ is $C_1$-$C_4$ alkyl or halogen; and
m is 0, 1 or 2; or
a salt thereof.

Another embodiment of the third aspect of the invention, wherein Z is C—$R_{13}$, provides a 1-aryl-5-alkyl pyrazoles of formula (I) wherein:
$R_1$ is cyano;
$R_2$ is —$S(O)_mR_{11}$;
$R_3$ is methyl or ethyl substituted with one to three halogens;
$R_4$, $R_5$, and $R_7$ are independently hydrogen or halogen;
$R_6$ is $C_1$-$C_4$ haloalkyl, $C_1$-$C_4$ haloalkoxy or —$SF_5$;
$R_{11}$ is $C_1$-$C_4$ haloalkyl;
$R_{13}$ is $C_1$-$C_4$ alkyl or halogen; and
m is 0, 1 or 2; or
a salt thereof.

Another embodiment of the third aspect of the invention wherein Z is C—$R_{13}$, provides a 1-aryl-5-alkyl pyrazoles of formula (I) wherein:
$R_1$ is cyano;
$R_2$ is —$S(O)_m R_{11}$;
$R_3$ is —$CH_2F$, or —$CHF_2$;
$R_4$ is hydrogen, fluoro or chloro;
$R_5$ and $R_7$ are both hydrogen;
$R_6$ is —$CF_3$, —$OCF_3$ or $SF_5$;
$R_{11}$ is —$CF_3$, —$CClF_2$ or —$CCl_2F$;
$R_{13}$ is methyl, fluoro or chloro; and
m is 0, 1 or 2; or
a salt thereof.

Another embodiment of the third aspect of the invention wherein Z is C—$R_{13}$, provides a 1-aryl-5-alkyl pyrazoles of formula (I):
$R_1$ is cyano;
$R_2$ is —$S(O)_m R_{11}$;
$R_3$ is —$CH_2F$, or —$CHF_2$;
$R_4$ is Cl;
$R_5$ and $R_7$ are both hydrogen;
$R_6$ is —$CF_3$, —$OCF_3$ or —$SF_5$;
$R_{11}$ is —$CF_3$, —$CClF_2$ or —$CCl_2F$;
$R_{13}$ is chloro or fluoro; and
m is 0, 1 or 2; or
a salt thereof.

The invention also provides novel intermediate compounds (Ia) for the production of a 1-aryl-5-alkyl pyrazole compound of formula (Ia):

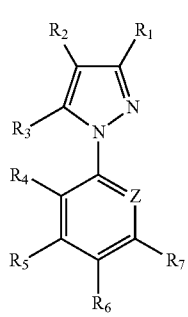

(Ia)

wherein:
$R_1$ is hydrogen, cyano, halogen, $R_8$, formyl, —$C(O)R_8$, —$C(O)OR_8$, —$C(O)NR_9R_{10}$, or —$C(S)NH_2$;
$R_2$ is $R_8$ or —$S(O)_m R_{11}$;
$R_3$ is $C_1$-$C_4$ alkyl, substituted with at least one —OH;
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —$C(O)R_{12}$, —$S(O)_n R_{12}$ or $SF_5$;
Z is C—F;
$R_8$ is alkyl, haloalkyl, cycloalkyl or halocycloalkyl;
$R_9$ is hydrogen, alkyl or haloalkyl;
$R_{10}$ is hydrogen, alkyl or haloalkyl;
$R_{11}$ is alkyl, haloalkyl, alkenyl, haloalkenyl, alkynyl, haloalkynyl or cycloalkyl;
$R_{12}$ is alkyl or haloalkyl;
m is 0, 1 or 2; and
n is 0, 1 or 2; or
a salt thereof.

Another embodiment of the 1-aryl-5-alkyl pyrazole compound of formula (Ia) is:
$R_1$ is hydrogen, cyano, halogen, $R_8$, formyl, —$C(O)R_8$, —$C(O)OR_8$, —$C(O)NR_9R_{10}$, or —$C(S)NH_2$;
$R_2$ is $R_8$ or —$S(O)_m R_{11}$;
$R_3$ is $C_1$-$C_4$ alkyl, substituted with at least one —OH;
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —$C(O)R_{12}$, —$S(O)_n R_{12}$ or $SF_5$;
Z is a nitrogen atom or C—F;
$R_8$ is alkyl, haloalkyl, cycloalkyl or halocycloalkyl;
$R_9$ is hydrogen, alkyl or haloalkyl;
$R_{10}$ is hydrogen, alkyl or haloalkyl;
$R_{11}$ is alkyl, haloalkyl, alkenyl, haloalkenyl, alkynyl, haloalkynyl or cycloalkyl;
$R_{12}$ is alkyl or haloalkyl;
m is 0, 1 or 2; and
n is 0, 1 or 2; or
a salt thereof.

Another embodiment of the 1-aryl-5-alkyl pyrazole compound of formula (Ia) is:
$R_1$ is hydrogen, cyano, halogen, $R_8$, formyl, —$C(O)R_8$, —$C(O)OR_8$, —$C(O)NR_9R_{10}$, or —$C(S)NH_2$;
$R_2$ is alkyl, haloalkyl or, —$S(O)_m R_{11}$, or cycloalkyl
$R_3$ is $C_1$-$C_4$ alkyl, substituted with at least one —OH;
$R_4$, $R_5$ and $R_7$ are independently hydrogen, halogen, alkyl, haloalkyl, alkoxy, cyano or nitro;
$R_6$ is halogen, alkyl, haloalkyl, alkoxy, haloalkyloxy, cyano, nitro, —$C(O)R_{12}$, —$S(O)_n R_{12}$ or $SF_5$;
Z is C—F;
$R_8$ is alkyl, haloalkyl, cycloalkyl or halocycloalkyl;
$R_9$ is hydrogen, alkyl or haloalkyl;
$R_{10}$ is hydrogen, alkyl or haloalkyl;
$R_{11}$ is alkyl, haloalkyl, alkenyl, haloalkenyl, alkynyl, haloalkynyl or cycloalkyl;
$R_{12}$ is alkyl or haloalkyl;
m is 0, 1 or 2; and
n is 0, 1 or 2; or
a salt thereof.

Another embodiment of the invention provides 1-aryl-5-alkyl pyrazoles of formula (I) wherein:
$R_1$ is hydrogen, cyano, halogen, $R_8$, formyl, —$C(O)R_8$, —$C(O)OR_8$, —$C(O)NR_9R_{10}$, or —$C(S)NH_2$;
$R_2$ is $C_1$-$C_4$ alkyl, $C_1$-$C_4$ haloalkyl, or —$S(O)_m R_{11}$,
$R_3$ is a $C_1$-$C_4$ alkyl, substituted with an —OH;
$R_4$, $R_5$ and $R_7$ are independently hydrogen, halogen, $C_1$-$C_4$ alkyl, $C_1$-$C_4$ haloalkyl, cyano or nitro;
$R_6$ is halogen, $C_1$-$C_4$ alkyl, $C_1$-$C_4$ haloalkyl, $C_1$-$C_4$ alkoxy, $C_1$-$C_4$ haloalkyloxy, cyano, nitro, —$C(O)R_{12}$, —$S(O)_n R_{12}$ or $SF_5$;
Z is C—F;
$R_8$ is $C_1$-$C_4$ alkyl, $C_1$-$C_4$ haloalkyl or cycloalkyl optionally substituted with one or more halogens;
$R_9$ is hydrogen, $C_1$-$C_4$ alkyl or $C_1$-$C_4$ haloalkyl;
$R_{10}$ is hydrogen, $C_1$-$C_4$ alkyl or $C_1$-$C_4$ haloalkyl;
$R_{11}$ is $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl or cycloalkyl;
$R_{12}$ is $C_1$-$C_4$ alkyl or $C_1$-$C_4$ haloalkyl;
m is 0, 1 or 2; and
n is 0, 1 or 2; or
a salt thereof.

Another embodiment of the invention provides 1-aryl-5-alkyl pyrazoles of formula (I) wherein:
$R_1$ is hydrogen, cyano, fluoro, chloro, $R_8$, formyl, —$C(O)R_8$, —$C(O)OR_8$, —$C(O)NR_9R_{10}$, or —$C(S)NH_2$;

$R_2$ is $C_1$-$C_2$ alkyl, $C_1$-$C_2$ fluoroalkyl or —S(O)$_m$R$_{11}$;

$R_3$ is $C_1$-$C_4$ alkyl, substituted with an —OH;

$R_4$, $R_5$ and $R_7$ are independently selected from the group consisting of hydrogen, fluoro, chloro, $C_1$-$C_2$ alkyl, $C_1$-$C_2$ fluoroalkyl, $C_1$-$C_2$ chloroalkyl, $C_1$-$C_2$ alkoxy, $C_1$-$C_2$ fluoroalkoxy, $C_1$-$C_2$ chloroalkoxy, $C_1$-$C_2$ alkylthio, $C_1$-$C_2$ fluoroalkylthio, $C_1$-$C_2$ chloroalkylthio, cyano and nitro;

$R_6$ is fluoro, chloro, $C_1$-$C_2$ alkyl, $C_1$-$C_2$ fluoroalkyl, $C_1$-$C_2$ chloroalkyl, $C_1$-$C_2$ alkoxy, $C_1$-$C_2$ fluoroalkyloxy, $C_1$-$C_2$ chloroalkyloxy, cyano, nitro, —C(O)R$_{12}$, —S(O)$_n$R$_{12}$ or SF$_5$;

Z is C—F;

$R_8$ is $C_1$-$C_2$ alkyl, $C_1$-$C_2$ fluoroalkyl or $C_1$-$C_2$ chloroalkyl;

$R_9$ is hydrogen, $C_1$-$C_2$ alkyl, $C_1$-$C_2$ fluoroalkyl or $C_1$-$C_2$ chloroalkyl;

$R_{10}$ is hydrogen, $C_1$-$C_2$ alkyl, $C_1$-$C_2$ fluoroalkyl or $C_1$-$C_2$ chloroalkyl;

$R_{11}$ is $C_1$-$C_2$ alkyl, $C_1$-$C_2$ fluoroalkyl, $C_1$-$C_2$ chloroalkyl, $C_2$-$C_4$ alkenyl, $C_2$-$C_4$ fluoroalkenyl, $C_2$-$C_4$ chloroalkenyl, $C_2$-$C_4$ alkynyl, $C_2$-$C_4$ fluoroalkynyl or $C_2$-$C_4$ chloroalkynyl;

$R_{12}$ is $C_1$-$C_2$ alkyl, $C_1$-$C_2$ fluoroalkyl or $C_1$-$C_2$ chloroalkyl;

m is 0, 1 or 2; and n is 0, 1 or 2; or a salt thereof.

Compositions

Also contemplated within the scope of the invention are acid or base salts, where applicable, of the 1-aryl-5-alkyl-pyrazoles provided for herein.

The term "acid" contemplates all pharmaceutically, veterinary or agriculturally acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylstearic acid. Other acids include gluconic acid, glucoheptonic acid and lactobionic acid.

The term "base" contemplates all pharmaceutically, veterinary or agriculturally acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

Ectoparasiticidal compositions of the invention comprise a 1-aryl-5-alkyl pyrazole and an acceptable carrier, for example a veterinarily acceptable carrier or an ectoparasiticidally acceptable carrier. In one embodiment of the invention, the ectoparasiticidally acceptable carrier is an organic solvent commonly used in the formulation art. These organic solvents may be found, for example, in Remington Pharmaceutical Science, 16$^{th}$ Edition (1986). These solvents include, for example, acetone, ethyl acetate, methanol, ethanol, isopropanol, dimethylformamide, dichloromethane or diethylene glycol monoethyl ether (Transcutol). These solvents can be supplemented by various excipients according to the nature of the desired phases, such as $C_8$-$C_{10}$ caprylic/capric triglyceride (Estasan or Miglyol 812), oleic acid or propylene glycol.

Pesticidal compositions of the invention comprise a 1-aryl-5-alkyl pyrazole and an acceptable carrier, for example a agriculturally acceptable carrier. In one embodiment of the invention, the agriculturally acceptable carrier is an organic solvent commonly used in the formulation art. These organic solvents may be found, for example, in C. Marsden, "Solvents Guide", 2nd Ed., Interscience, N.Y. 1963. These solvents include, for example, acetone, butanol, cyclohexanone, dimethylformamide, xylene or else higher-boiling aromatics or hydrocarbons or mixtures of these. These solvents can be supplemented by various ionic and/or nonionic surfactants (emulsifiers).

Formulations and Administration for Pharmaceutical/Veterinary Use

The composition of the invention can also be in a variety of forms which include, but are not limited to, oral formulations, injectable formulations, and topical, dermal or subdermal formulations.

The composition of the invention may be in a form suitable for oral use, for example, as baits (see, e.g., U.S. Pat. No. 4,564,631), dietary supplements, troches, lozenges, chewables, tablets, hard or soft capsules, emulsions, aqueous or oily suspensions, aqueous or oily solutions, oral drench formulations, dispersible powders or granules, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the 1-aryl-5-alkyl pyrazole compound of the invention, the paste can also contain fumed silica; a viscosity modifier; a carrier; optionally, an absorbent; and optionally, a colorant, stabilizer, surfactant, or preservative.

The process for preparing a paste formulation comprises the steps of:

(a) dissolving or dispersing the 1-aryl-5-alkyl compound into the carrier by mixing;

(b) adding the fumed silica to the carrier containing the dissolved 1-aryl-5-alkyl pyrazole compound and mixing until the silica is dispersed in the carrier;

(c) allowing the intermediate formed in (b) to settle for a time sufficient in order to allow the air entrapped during step (b) to escape; and (d) adding the viscosity modifier to the intermediate with mixing to produce a uniform paste.

The above steps are illustrative, but not limiting. For example, step (a) can be the last step.

In one embodiment of the formulation, the formulation is a paste containing 1-aryl-5-alkyl pyrazole compound, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (polysorbate 80 or Tween 80), and polyoxamers (e.g., Pluronic L 81); an absorbent selected from the group consisting of magnesium carbonate, calcium carbonate, starch, and cellulose and its derivatives; and a colorant selected from the group consisting of titanium dioxide iron oxide, and FD&C Blue #1 Aluminum Lake.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions. Topical application of an inventive compound or of a composition including at least one inventive compound among active agent(s) therein, a spot-on composition, can allow for the inventive compound to be distributed through the glands (e.g. sebaceous glands) of the animal and/or allow active agent(s) to achieve a systemic effect (plasma concentration) or throughout the haircoat. When the compound is distributed throughout glands, the glands can act as a reservoir, whereby there can be a long-lasting, e.g. 1-2 months effect. Spot-on formulations are typically applied in a localized region which refers to an area other than the entire animal. In one embodiment of a localized region, the location is between the shoulders. In another embodiment of a localized region is a stripe, e.g. a stripe from head to tail of the animal.

Pour-on formulations are described in U.S. Pat. No. 6,010,710, incorporated herein by reference. The pour-on formulations are advantageously oily, and generally comprise a diluent or vehicle and also a solvent (e.g. an organic solvent) for the active ingredient if the latter is not soluble in the diluent.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, mention may be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent will be added. One embodiment of the emollient and/or spreading and/or film-forming agent are those agents selected from the group consisting of:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+R'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the 1-aryl-5-alkyl pyrazole compound and its solubility in this solvent. It will be sought to have the lowest possible volume. The vehicle makes up the difference to 100%.

In one embodiment of the amount of emollient, the emollient is used in a proportion selected from the group consisting of from 0.1 to 10% and 0.25 to 5%, by volume.

In another embodiment of the invention, the composition can be in ready-to-use solution form as is described in U.S. Pat. No. 6,395,765, incorporated herein by reference. In addition to the 1-aryl-5-alkyl pyrazole compound, the ready-to-use solution can contain a crystallization inhibitor, an organic solvent and an organic co-solvent.

In one embodiment of the amount of crystallization inhibitor, the crystallization inhibitor can be present in a proportion selected from the group consisting of about 1 to about 20% (w/v) and about 5 to about 15%. In another embodiment of the amount of crystallization inhibitor, the amount corresponds to the test in which 0.3 ml of a solution comprising 10% (w/v) of 1-aryl-5-alkyl pyrazole compound in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystal.

The organic solvent has a dielectric constant of a range selected from the group consisting of between about 10 and 35 and between about 20 and 30, the content of this organic solvent in the overall composition representing the complement to 100% of the composition; and the organic co-solvent having a boiling point selected from the ranges consisting of below 100° C., and below 80° C., and having a dielectric constant of a range selected from the group consisting of between about 10 and 40 and between about 20 and 30; this co-solvent may be present in the composition in a organic co-solvent/organic solvent weight/weight (W/W) ratio of between about 1/15 and 1/2. The solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:

(a) polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+R'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used.

Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinyl pyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied can be of the order of about 0.3 to about 1 ml. In one embodiment for the volume, the volume is on the order of about 0.5 ml, for cats and on the order of about 0.3 to about 3 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference), which in one embodiment of the spot-on formulation comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

The liquid carrier vehicle can optionally contain a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters;

lecithin, sodium carboxymethylcellulose, and acrylic derivatives, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent is present in the formulation at a concentration of about 0.05 to 10% weight/volume. In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

Formulations and Administration for Agrochemical Use

The compounds of the formula (I) or their salts can be employed as such or in the form of their preparations (formulations) alone or as combinations with other pesticidally active substances, such as, for example, insecticides, attractants, sterilants, acaricides, nematicides, herbicides, fungicides, and with safeners, fertilizers and/or growth regulators, for example as a premix/readymix.

The insecticides include, for example, phosphoric esters, carbamates, carboxylic esters, chlorinated hydrocarbons, phenylureas, substances prepared by microorganisms.

Examples of insecticides which may optionally be admixed include but are not limited to:

phosphoric esters, such as azinphos-ethyl, azinphos-methyl, α-1(4-chlorophenyl)-4-(O-ethyl, S-propyl)phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, poxim, pirimiphos-ethyl, pirimiphos-methyl, profenofos, prothiofos, sulfprofos, triazophos and trichlorphon;

carbamates, such as aldicarb, bendiocarb, α-2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds (e.g. dimethyl(phenyl)silyl-methyl 3-phenoxybenzyl ethers, such as dimethyl-(4-ethoxyphenyl)-silylmethyl 3-phenoxybenzyl ether) or (dimethylphenyl)-silyl-methyl 2-phenoxy-6-pyridylmethyl ethers such as, for example, dimethyl-(9-ethoxy-phenyl)-silylmethyl 2-phenoxy-6-pyridylmethyl ether or [(phenyl)-3-(3-phenoxyphenyl)-propyl][(dimethyl)-silanes such as, for example, (4-ethoxyphen-yl)-[3-(4-fluoro-3-phenoxyphenyl-propyl]dimethyl-silane, silafluofen;

pyrethroids (which are also useful for their repellent properties, e.g. against mosquitoes), such as allethrin, alphamethrin, bioresmethrin, byfenthrin, cycloprothrin, cyfluthirin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropane-carboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridinyl)-methyl]-4,5-dihydro-N-nitro-1H-imidazole-2-amine (imidacloprid), N-[(6-chloro-3-pyridyl)-methyl]-$N^2$-cyano-$N^1$-methylacetamide (NI-25);

abamectin, AC 303, 630 (chlorfenapyr), acephate, acrinathrin, alanycarb, aldoxycarb, aldrin, amitraz, azamethiphos, *Bacillus thuringiensis*, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tert-butyl-pyrimidin-5-yl-o-isopropylphosphorothiate, thiocyclam, thiofanox, thiometon, tralomethrin, triflumuron, trimethacarb, vamidothion, *Verticillium Lacanii*, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alphacypermethrin, cyophenothrin, cyromazine, dazomet, DDT, demeton-S-methylsulphone, diafenthiuron, dialifos, dicrotophos, diflubenzuron, dinoseb, deoxabenzofos, diazacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous chloride, metam, metarthizium, anisopliae, methacrifos, methamidophos, methidathion, methiocarb, methoprene, methoxychlor, methyl isothiocyanate, metholcarb, mevinphos, monocrotophos, naled, Neodiprion sertifer NPV, nicotine, omethoate, oxydemeton-methyl, pentachlorophenol, petroleum oils, phenothrin, phenthoate, phorate.

Other insecticides that may optionally be admixed may also be from the class of the compounds described by U.S. Pat. No. 7,001,903.

Fungicides which may optionally be admixed are include but are not limited to:

(1) Triazoles which include but are not limited to:
azaconazole, propiconazole, tebuconazole, cyproconazole, metconazole, amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, paclobutrazol, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

(2) Imidazoles which include but are not limited to:
imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.

(3) "Methyl (E)-2-phenyl-3-methoxyacrylate" compounds which include but are not limited to: methyl (E)-2-[2-[6-(2-cyanophenoxyl)pyrimidin-4-yloxy]phenyl]3-methoxyacrylate, methyl (E)-2-[2-[6-(2-thioamidophenoxyl)pyrimidin-4-yloxy]phenyl]-3-methoxyacrylate, methyl (E)-2-[2-[6-(2-fluorophenoxyl)pyrimidin-4-yloxy]phenyl]-3-methoxyacrylate, methyl (E)-2-[2-[6-(2,6-difluorophenoxyl)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl]-3-methoxyacrylate, methyl (E)-2-[2-[3-(4-nitrophenoxyl)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy)phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxyphenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxyl)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxyl)phenoxy]phenyl]-3-methoxyacrylate, methyl (E)-2-[2-[(3-methylpyridin-2-yloxymethyl)phenyl]-3-methoxyacrylate, methyl (E)-2-[2-[6-(2-methylphenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-di-methylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxyacrylate, methyl (E),(E)-2-{2-(3-methoxyphenyl)methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3-methoxyacrylate, and methyl (E),(E)-2-{2-[(3-nitrophenyl)methyloximinomethyl]phenyl}-3-methoxyacrylate;

(4) Succinate Dehydrogenase Inhibitors which include but are not limited to:
  (a) fenfuram, furcarbanil, cyclafluramid, furmecyclox, seedvax, metsulfovax, pyrocarbolid, oxycarboxin, shirlan, mebenil (mepronil), benodanil, flutolanil (Moncut);
  (b) naphthalene derivatives such as terbinafine, naftifine, butenafine, 3-chloro-7-(2-aza-2,7,7-trimethyl-oct-3-en-5-ine);
  (c) sulphenamides such as dichlofluanid, tolylfluanid, folpet, fluorfolpet; captan, captofol;
  (d) benzimidazoles such as carbendazim, benomyl, furathiocarb, fuberidazole, thiophonatmethyl, thiabendazole or their salts;
  (e) morpholine derivatives such as fenpropimorph, falimorph, dimethomorph, dodemorph, aldimorph, fenpropidine and their arylsulphonates, such as, for example, p-toluenesulphonic acid and p-dodecylphenyl-sulphonic acid;
  (f) dithiocarbamates, cufraneb, ferbam, mancopper, mancozeb, maneb, metam, metiram, thiram zeneb, ziram;
  (g) benzothiazoles, such as 2-mercaptobenzothiazole;
  (h) benzamides, such as 2,6-dichloro-N-(4-trifluoromethylbenzyl)-benzamide;
  (i) boron compounds, such as boric acid, boric esters, borax;
  (j) formaldehyde and formaldehyde-releasing compounds, such as benzyl alcohol mono-(poly)-hemiformal, oxazolidine, hexa-hydro-S-triazines, N-methylolchloroacetamide, paraformaldehyde, nitropyrin, oxolinic acid, tecloftalam;
  (k) tris-N-(cyclohexyldiazeniumdioxy)-aluminium, N-(cyclo-hexyldiazeniumdioxy)-tributyltin or K salts, bis-N-(cyclohexyldiazeniumdioxy)-copper, N-methylisothiazolin-3-one, 5-chloro-N-methylisothiazolin-3-one, 4,5-dichloro-N-octylisothiazolin-3-one, N-octylisothiazolin-3-one, 4,5-trimethylene-isothiazolinone, 4,5-benzoisothiazolinone, N-methylolchloroacetamide;
  (l) aldehydes, such as cinnamaldehyde, formaldehyde, glutaraldehyde, β-bromo-cinnamaldehyde;
  (m) thiocyanates, such as thiocyanatomethylthiobenzothiazole, methylenebisthiocyanate, and the like;
  (n) quaternary ammonium compounds, such as benzyldimethyltetradecylammonium chloride, benzyldimethyldodecylanmuonium chloride, didecyldimethylammonium chloride;
  (o) iodine derivatives, such as diiodomethyl p-tolyl sulphone, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;
  (p) phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts;
  (q) microbicides having an activated halogen group, such as chloroacetamide, bronopol, bronidox, tectamer, such as 2-bromo-2-nitro-1,3-propanediol, 2-bromo-4'-hydroxyacetophenone, 2,2-dibromo-3-nitrile-propionamide, 1,2-dibromo-2,4-dicyanobutane, β-bromo-β-nitrostyrene;
  (r) pyridines, such as 1-hydroxy-2-pyridinethione (and their Na, Fe, Mn, Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridine;
  (s) metal soaps, such as tin naphthenate, copper naphthenate, zinc naphthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;
  (t) metal salts, such as copper hydroxycarbonate, sodium dichromate, potassium dichromate, potassium chromate, copper sulphate, copper chloride, copper borate, zinc fluorosilicate, copper fluorosilicate, and mixtures with fixatives;
- (u) oxides, such as tributyltin oxide, $Cu_2O$, CuO, ZnO;
- (v) dialkyldithiocarbamates, such as Na and Zn salts of dialkyldithiocarbamates, tetramethylthiuram disulphide, potassium N-methyl-dithiocarbamate;
- (w) nitriles, such as 2,4,5,6-tetrachloroisophthalodinitrile, disodium cyano-dithioimido-carbamate;
- (x) quinolines, such as 8-hydroxyquinoline, and their Cu salts;
- (y) mucochloric acid, 5-hydroxy-2(5H)-furanone;
- (z) 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxymethyl-N'-methyl-dithiocarbamate, 2-oxo-2-(4-hydroxy-phenyl)acetohydroximic acid chloride, phenyl-(2-chloro-cyano-vinyl) sulphone, phenyl-(1,2-dichloro-2-cyano-vinyl) sulphone; and
- (aa) Ag-, Zn- or Cu-containing zeolites, alone or enclosed in polymeric active compounds, or
- (bb) mixtures of more than one of the abovementioned fungicides.

Particularly favorable mixing components are, for example, the following compounds:

Fungicides:
Inhibitors of nucleic acid synthesis which include but are not limited to benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid;
Inhibitors of mitosis and cell division which include but are not limited to benomyl, carbendazim, diethofencarb, fuberidazole, pencycuron, thiabendazole, thiophanat-methyl, zoxamide;
Inhibitors of respiratory chain complex I which include but are not limited to diflumetorim;
Inhibitors of respiratory chain complex II which include but are not limited to boscalid, carboxin, fenfuram, flutolanil, furametpyr, mepronil, oxycarboxin, penthiopyrad, thifluzamide;
Inhibitors of respiratory chain complex III which include but are not limited to azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin;
Decouplers which include but are not limited to dinocap, fluazinam;
Inhibitors of ATP production which include but are not limited to fentin acetate, fentin chloride, fentin hydroxide, silthiofam;
Inhibitors of amino acid biosynthesis and protein biosynthesis which include but are not limited to andoprim, blasticidin-S, cyprodinil, kasugamycin, kasugamycin hydrochloride hydrate, mepanipyrim, pyrimethanil;
Inhibitors of signal transduction which include but are not limited to fenpiclonil, fludioxonil, quinoxyfen;
Inhibitors of lipid and membrane synthesis which include but are not limited to chlozolinate, iprodione, procymidone, vinclozolin, ampropylfos, potassium-ampropylfos, edifenphos, iprobenfos (IBP), isoprothiolane, pyrazophos, tolclofos-methyl, biphenyl, iodocarb, propamocarb, propamocarb hydrochloride;
Inhibitors of ergosterol biosynthesis which include but are not limited to fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;
Inhibitors of cell wall synthesis which include but are not limited to benthiavalicarb, bialaphos, dimethomorph, flumorph, iprovalicarb, polyoxins, polyoxorim, validamycin A;
Inhibitors of melanin biosynthesis which include but are not limited to capropamid, diclocymet, fenoxanil, phthalid, pyroquilon, tricyclazole;
Resistance inductors which include but are not limited to acibenzolar-S-methyl, probenazole, tiadinil;
Multisite which include but are not limited to captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram;
Unknown mechanism which include but are not limited to amibromdol, benthiazol, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrol nitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzene-sulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl] pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino] oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy) phenyl]ethyl]benzacetamide, (2S)—N-[2-[4-[[3-(4- chlorophenyl)-2-propynyl]oxy]-3-methoxyphenyl]
ethyl]-3-methyl-2-[(methylsulphonyl)amino]
butanamide, 5-chloro-7-(4-methylpiperidin-1-yl)-6-(2,
4,6-trifluorophenyl)[1,2,4]triazolo[1,5-a]pyrimidine,
5-chloro-6-(2,4,6-trifluorophenyl)-N-[(1R)-1,2,2-trimethylpropyl][1,2,4]triazolo[1,5-a]pyrimidin-7-amine,
5-chloro-N-[(1R)-1,2-dimethylpropyl]-6-(2,4,6-trifluorophenyl)[1,2,4]triazolo[1,5-a]pyrimidin-7-amine,
N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide,
N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide;

Bactericides:
which include but are not limited to bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations;

Insecticides/Acaricides/Nematicides:
Acetylcholine esterase (AChE) inhibitors;
Carbamates which include but are not limited to alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate;

Organophosphates which include but are not limited to acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion;

Sodium channel modulators/voltage-dependent sodium channel blockers;
Pyrethroids which include but are not limited to acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum);

DDT;
Oxadiazines which include but are not limited to indoxacarb;
Semicarbazones which include but are not limited to metaflumizone (BAS3201);
Acetylcholine receptor agonists/antagonists which include but are not limited to chloronicotinyls, for example, acetamiprid, clothianidin, dinotefuran, imidacloprid, nitenpyram, nithiazine, thiacloprid, imidaclothiz, AKD-1022, thiamethoxam, nicotine, bensultap, cartap;
Acetylcholine receptor modulators which include but are not limited to spinosyns, for example, spinosad, spinetoram (XDE-175);
GABA-controlled chloride channel antagonists which include but are not limited to organochlorines, for example, camphechlor, chlordane, endosulphan, gamma-HCH, HCH, heptachlor, lindane, methoxychlor; fiprols, for example, acetoprole, ethiprole, fipronil, pyrafluprole, pyriprole, vaniliprole
Chloride channel activators which include but are not limited to avermectins and milbemycins, for example, abamectin, emamectin, emamectin-benzoate, ivermectin, lepimectin, milbemycin, milbemycin oxime, selamectin, doramectin, dimadectin, moxidectin;
Juvenile hormone mimetics which include but are not limited to example diofenolan, epofenonane, fenoxycarb, hydroprene, kinoprene, methoprene, pyriproxifen, triprene;
Ecdysone agonists/disruptors which include but are not limited to diacylhydrazines, for example, chromafenozide, halofenozide, methoxyfenozide, tebufenozide;
Chitin biosynthesis inhibitors which include but are not limited to benzoylureas, for example, bistrifluron, chlofluazuron, diflubenzuron, fluazuron, flucycloxuron, flufenoxuron, hexaflumuron, lufenuron, novaluron, noviflumuron, penfluron, teflubenzuron, triflumuron; buprofezin, cyromazine;
Oxidative phosphorylation inhibitors, ATP disruptors which include but are not limited to diafenthiuron, organotin compounds, for examples, azocyclotin, cyhexatin, fenbutatin-oxide;
Oxidative phosphorylation decouplers acting by interrupting the H-proton gradient which include but are not limited to pyrroles, for example, chlorfenapyr; dinitrophenols, for example, binapacyrl, dinobuton, dinocap, DNOC Site-I electron transport inhibitors which include but are not limited to METIs, for example, fenazaquin, fenpyroximate, pyrimidifen, pyridaben, tebufenpyrad, tolfenpyrad; hydramethylnon, dicofol;

Site-II electron transport inhibitors which include but are not limited to rotenone;

Site-III electron transport inhibitors which include but are not limited to acequinocyl, fluacrypyrim;

Microbial disruptors of the insect gut membrane

Bacillus thuringiensis strains;

Lipid synthesis inhibitors which include but are not limited to tetronic acids, for example. spirodiclofen, spiromesifen; tetramic acids, for example spirotetramat; carboxamides, for example, flonicamid; octopaminergic agonists, for example, amitraz;

Inhibitors of magnesium-stimulated ATPase which include but are not limited to propargite, nereistoxin analogs, for example, thiocyclam hydrogen oxalate, thiosultap-sodium;

Ryanodin receptor agonists which include but are not limited to benzoic acid dicarboxamides, for example, flubendiamid; anthronilamides, for example, pynaxypyr (3-bromo-N-{4-chloro-2-methyl-6-[(methylamino)carbonyl]phenyl}-1-(3-chloropyridin-2-yl)-1H-pyrazole-5-carboxamide);

Biologicals, hormones or pheromones which include but are not limited to azadirachtin, *Bacillus* spec., *Beauveria* spec., codlemone, *Metarrhizium* spec., *Paecilomyces* spec., *thuringiensin, Verticillium* spec.;

Active compounds with unknown or unspecific mechanisms of action which include but are not limited to fumigants, for example aluminium phosphide, methyl bromide, sulphuryl fluoride, antifeedants, for example cryolite, flonicamid, pymetrozine, mite growth inhibitors, for example clofentezine, etoxazole, hexythiazox; amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin.

Herbicides which are known from the literature and which can be mentioned, which can be combined with the compounds of the formula (I), are, for example, the following active substances (Note: the compounds are either designated by the common name according to the International Organization for Standardization (ISO) or using the chemical name, if appropriate together with a customary code number):

acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; amitrol; AMS, i.e. ammonium sulfamate; anilofos; asulam; atrazine; azafenidin; azimsulfuron (DPX-A8947); aziprotryn; barban; BAS 516 H, i.e. 5-fluoro-2-phenyl-4H-3,1-benzoxazin-4-one; beflubutamid; benazolin(-ethyl); benfluralin; benfuresate; bensulfuron (-methyl); bensulide; bentazone(-sodium); benzobicyclone; benzofenap; benzofluor; benzoylprop(-ethyl); benzthiazuron; bialaphos (bilanafos); bifenox; bispyribac(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole (CH-900); carbetamide; carfentrazone(-ethyl); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorflurenol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon(-methyl or -ethyl), cinmethylin; cinosulfuron; clethodim; clefoxydim, clodinafop and its ester derivatives (for example clodinafop-propargyl); clomazone; clomeprop; cloproxydim; clopyralid; clopyrasulfuron (-methyl); cloransulam(-methyl); cumyluron (JC 940); cyanazine; cycloate; cyclosulfamuron (AC 104); cycloxydim; cycluron; cyhalofop and its ester derivatives (for example butyl-ester, DEH-112); cyperquat; cyprazine; cyprazole; daimuron; 2,4-D; 2,4-DB; dalapon; dazomet, desmedipham; desmetryn; di-allate; dicamba; dichlobenil; dichlorprop(-P); diclofop and its esters such as diclofop-methyl; diclosulam, diethatyl(-ethyl); difenoxuron; difenzoquat; diflufenican; diflufenzopyr; dimefuron; dimepiperate; dimethachlor; dimethametryn; dimethenamid (SAN-582H); dimethenamid(-P); dimethazone, dimethipin; dimexyflam, dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example ethyl ester, HC-252), ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl] ethanesulfonamide; fenoprop; fenoxan, fenoxaprop and fenoxaprop-P and their esters, for example fenoxaprop-P-ethyl and fenoxaprop-ethyl; fenoxydim; fentrazamide; fenuron; flamprop(-methyl or -isopropyl or -isopropyl-L); flazasulfuron; florasulam; fluazifop and fluazifop-P and their esters, for example fluazifop-butyl and fluazifop-P-butyl; fluazolate, flucarbazone(-sodium); fluchloralin; flufenacet (FOE 5043), flufenpyr, flumetsulam; flumeturon; flumiclorac (-pentyl); flumioxazin (S-482); flumipropyn; fluometuron; fluorochloridone, fluorodifen; fluoroglycofen(-ethyl); flupoxam (KNW-739); flupropacil (UBIC-4243); fluproanate, flupyrsulfuron(-methyl, or -sodium); flurenol(-butyl); fluridone; flurochloridone; fluroxypyr(-meptyl); flurprimidol, flurtamone; fluthiacet(-methyl); fluthiamide (also known as flufenacet); fomesafen; foramsulfuron; fosamine; furilazole (MON 13900), furyloxyfen; glufosinate(-ammonium); glyphosate(-isopropylammonium); halosafen; halosulfuron (-methyl) and its esters (for example the methyl ester, NC-319); haloxyfop and its esters; haloxyfop-P (=R-haloxyfop) and its esters; HC-252 (diphenylether), hexazinone; imazamethabenz(-methyl); imazamethapyr; imazamox; imazapic, imazapyr; imazaquin and salts such as the ammonium salts; imazethamethapyr; imazethapyr, imazosulfuron; indanofan; iodosulfuron-(methyl)-(sodium), ioxynil; isocarbamid; isopropalin; isoproturon; isouron; isoxaben; isoxachlortole; isoxaflutole; isoxapyrifop; karbutilate; lactofen; lenacil; linuron; MCPA; MCPB; mecoprop; mefenacet; mefluidid; mesosulfuron(-methyl); mesotrione; metam, metamifop, metamitron; metazachlor; methabenzthiazuron; methazole; methoxyphenone; methyldymron; metobenzuron, metobromuron; (S-)metolachlor; metosulam (XRD 511); metoxuron; metribuzin; metsulfuron-methyl; MK-616; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron; oxaziclomefone; oxyfluorfen; paraquat; pebulate; pelargonic acid; pendimethalin; penoxulam; pentanochlor, pentoxazone; perfluidone; pethoxamid, phenisopham; phenmedipham; picloram; picolinafen; piperophos; piributicarb; pirifenop-butyl; pretilachlor; primisulfuron(-methyl); procarbazone(-sodium); procyazine; prodiamine; profluazole, profluralin; proglinazine(-ethyl); prometon; prometryn; propachlor; propanil; propaquizafop; propazine; propham; propisochlor; propoxycarbazone(-sodium), propyzamide; prosulfalin; prosulfocarb; prosulfuron (CGA-152005); prynachlor; pyraclonil, pyraflufen(-ethyl); pyrazolinate; pyrazon; pyrazosulfuron(-ethyl); pyrazoxyfen; pyribenzoxim; pyributicarb; pyridafol; pyridate; pyriftalid, pyrimidobac(-methyl); pyrithiobac(-sodium) (KIH-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazuron; sulfometuron(-methyl); sulfosate (ICI-A0224); sulfosulfuron; TCA; tebutam (GCP-5544); tebuthiuron; tepraloxydim; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide; thiazafluron; thiazopyr (Mon-13200); thidiazimin (SN-24085); thifensulfuron(-methyl); thiobencarb; tiocarbazil; tralkoxydim; tri-allate; triasulfuron; triaziflam; triazofenamide; tribenuron(-methyl); 2,3,6-trichlorobenzoic acid (2,3,6-TBA), triclopyr; tridiphane; trietazine; trifloxysulfuron(-sodium), trifluralin; triflusulfuron and esters (e.g. methyl ester, DPX-66037); trimeturon; tritosulfuron; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127; KIH-2023 and KIH5996.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Components which may be employed for the active substances according to the invention in mixed formulations, for example, known active compounds which are based on an inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other compounds which can be employed, whose mechanism of action is to a degree unknown or different, are described, for example, in Weed Research 26, 441-445 (1986), or "The Pesticide Manual", 12th Edition 2000 (hereinbelow also abbreviated to "PM"), The British Crop Protection Council and the Royal Soc. of Chemistry (editors) and literature cited therein.

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell, Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophillite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

In general, the agrochemical preparations comprise a range selected from the group consisting of about 0.1 to about 99% by weight and about 0.1 to about 95% by weight, of compounds of formula (I).

The concentration of compounds of formula (I) in wettable powders is, for example, about 10 to about 90% by weight, the remainder to 100% by weight being composed of customary formulation components. In the case of emulsifiable concentrates, the concentration of compounds of formula (I) can amount to ranges selected from the group consisting of about 1% to about 90% and about 5% to about 80% by weight. Formulations in the form of dusts usually comprise in the range selected from the group consisting of about 1% to about 30% by weight of compounds of formula (I) and about 5% to about 20% by weight of compounds of formula (I). For sprayable solutions comprise a range selected from the group consisting of about 0.05% to about 80% by weight of compounds of formula (I) and about 2% to about 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The mixtures according to the invention can be applied via the soil either pre-emergently or post-emergently. The mixtures according to the invention can also be applied via the leaf. The mixtures according to the invention can be employed for seed dressing. It is also possible to apply the mixtures according to the invention via an irrigation system, for example via the water for irrigation.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from about 0.00000001 to about 95% by weight of active compound, preferably between about 0.00001 and about 1% by weight.

The active compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds according to the invention are particularly suitable for treating seed. Here, the active compounds according to the invention mentioned above as preferred or particularly preferred may be mentioned as being preferred. Thus, a large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable active compounds is therefore of particularly great interest.

The control of pests by treating the seeds of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection agents being employed.

The present invention therefore in particular also relates to a method for the protection of seed and germinating plants from attack by pests, by treating the seed with an active compound according to the invention. The invention likewise relates to the use of the active compounds according to the invention for the treatment of seed for protecting the seed and the resultant plant from pests. Furthermore, the invention relates to seed which has been treated with an active compound according to the invention so as to afford protection from pests.

One of the advantages of the present invention is that the particular systemic properties of the active compounds according to the invention mean that treatment of the seed with these active compounds not only protects the seed itself, but also the resulting plants after emergence, from pests. In this manner, the immediate treatment of the crop at the time of sowing or shortly thereafter can be dispensed with.

Furthermore, it must be considered as advantageous that the active compounds according to the invention can also be employed in particular in transgenic seed, the plants arising from this seed being capable of expressing a protein directed against pests. By treating such seed with the active compounds according to the invention, certain pests can be controlled merely by the expression of the, for example, insecticidal protein, and additionally be protected by the active compounds according to the invention against damage.

The active compounds according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The active compounds according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with an active compound according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus*, *Rhizobium*, *Pseudomonas*, *Serratia*, *Trichoderma*, *Clavibacter*, *Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

In the context of the present invention, the active compound according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the active compound according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARDO (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the active compounds of the general formula I according to the invention. The preferred ranges stated above for the active compounds also apply to the treatment of these plants. Particular emphasis is given to the treatment of plants with the active compounds specifically mentioned in the present text.

In the field of household insecticides, the active compounds according to the invention are used alone or in combination with other suitable active compounds, such as phosphoric esters, carbamates, pyrethroids, neonicotinoids, growth regulators or active compounds from other known classes of insecticides.

It has furthermore been found that the active compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicoffis, Lyctus linearis, Lyctus pubescens, Trogoxylon aequale, Minthes rugicoffis, Xyleborus* spec. *Tryptodendron* spec. *Apate monachus, Bostiychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

The active compounds according to the invention are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

Other Active Agents for Pharmaceutical/Veterinary Use

Additional pesticidally or veterinarily active ingredients, which include, but are not limited to, acaricides, anthelmintics, anti-parasitics and insecticides, may also be added to the compositions of the invention. Anti-parasitic agents can include both ectoparasiticisal and endoparasiticidal agents. These agents are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil HCl, allopurinol, alprazolam, altrenogest, amantadine HCl, amikacin sulfate, aminocaproic acid, aminopentamide hydrogen sulfate, aminophylline/theophylline, amiodarone HCl, amitraz, amitriptyline HCl, amlodipine besylate, ammonium chloride, ammonium molybdenate, amoxicillin, amoxicillin, clavulanate potassium, amphotericin B desoxycholate, amphotericin B lipid-based, ampicillin, amprolium HCl, antacids (oral), antivenin, apomorphione HCl, apramycin sulfate, ascorbic acid, asparaginase, aspiring, atenolol, atipamezole HCl, atracurium besylate, atropine sulfate, aurnofin, aurothioglucose, azaperone, azathioprine, azithromycin, baclofen, barbituates, benazepril HCl, betamethasone, bethanechol chloride, bisacodyl, bismuth subsalicylate, bleomycin sulfate, boldenone undecylenate, bromides, bromocriptine mesylate, budenoside, buprenorphine HCl, buspirone HCl, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur HCl, ceftiaxone sodium, cephalexin, cephalosporins, cephapirin, charcoal (activated), chlorambucil, chloramphenicol, chlordiazepoxide, chlordiazepoxide +/− clidinium bromide, chlorothiazide, chlorpheniramine maleate, chlorpromazine HCl, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol HCl, clindamycin, clofazimine, clomipramine HCl, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine HCl, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine HCl, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin HCl, digoxin, dihydrotachysterol (DHT), diltiazem HCl, dimenhydrinate, dimercaprol/BAL, dimethyl sulfoxide, dinoprost tromethamine, diphenylhydramine HCl, disopyramide phosphate, dobutamine HCl, docusate/DSS, dolasetron mesylate, domperidone, dopamine HCl, doramectin, doxapram HCl, doxepin HCl, doxorubicin HCl, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol HCl, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine HCL, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline HCl, hydrochlorothiazide, hydrocodone bitartrate, hydrocortisone, hydromorphone, hydroxyurea, hydroxyzine, ifosfamide, imidacloprid, imidocarb dipropionate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol HCl, isotretinoin, isoxsuprine HCl, itraconazole, ivermectin, kaolin/pectin, ketamine HCl, ketoconazole, ketoprofen, ketorolac tromethamine, lactulose, leuprolide, levamisole, levetiracetam, levothyroxine sodium, lidocaine HCl, lincomycin HCl, liothyronine sodium, lisinopril, lomustine (CCNU), lufenuron, lysine, magnesium, mannitol, marbofloxacin, mechlorethamine HCl, meclizine HCl, meclofenamic acid, medetomidine HCl, medium chain triglycerides, medroxyprogesterone acetate, megestrol acetate, melarsomine, melatonin, meloxican, melphalan, meperidine HCl, mercaptopurine, meropenem, metformin HCl, methadone HCl, methazolamide, methenamine mandelate/hippurate, methimazole, methionine, methocarbamol, methohexital sodium, methotrexate, methoxyflurane, methylene blue, methylphenidate, methylprednisolone, metoclopramide HCl, metoprolol, metronidaxole, mexiletine HCl, mibolerlone, midazolam HCl milbemycin oxime, mineral oil, minocycline HCl, misoprostol, mitotane, mitoxantrone HCl, morantel tartrate, morphine sulfate, moxidectin, naloxone HCl, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone HCl, oxytretracycline, oxytocin, pamidronate disodium, pancreplipase, pancuronium bromide, paromomycin sulfate, parozetine HCl, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine HCl, pheylbutazone, phenylephrine HCL, phenypropanolamine HCl, phenytoin sodium, pheromones, parenteral phosphate, phytonadione/vitamin K-1, pimobendan, piperazine, pirlimycin HCL, piroxicam, polysulfated glycosaminoglycan, ponazuril, potassium chloride, pralidoxime chloride, praziquantel, prazosin HCl, prednisolone/prednisone, primidone, procainamide HCl, procarbazine HCl, prochlorperazine, propantheline bromide, propionibacterium acnes injection, propofol, propranolol HCl, protamine sulfate, pseudoephedrine HCl, psyllium hydrophilic mucilloid, pyrantel pamoate, pyridostigmine bromide, pyrilamine maleate, pyrimethamine, quinacrine HCl, quinidine, ranitidine HCl, rifampin, s-adenosyl-methionine (SAMe), saline/hyperosmotic laxative, selamectin, selegiline HCL/I-deprenyl, sertraline HCl, sevelamer HCl, sevoflurane, silymarin/milk thistle, sodium bicarbonate, sodium polystyrene sulfonate, sodium stibogluconate, sodium sulfate, sodum thiosulfate, somatotropin, sotalol HCl, spectinomycin HCl, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline HCl, terbutaline sulfate, testosterone, tetracycline HCl, thiabendazole, thiacetarsamide sodium, thiamine HCl, thioguanine, thiopental sodium, thiotepa, thyrotropin, tiamulin, ticarcilin disodium, tiletamine HCl/zolazepam HCl, tilmocsin, tiopronin, tobramycin sulfate, tocainide HCl, tolazoline HCl, telfenamic acid, topiramate, tramadol HCl, trimcinolone acetonide, trientine HCl, trilostane, trimepraxine tartrate w/prednisolone, tripelennamine HCl, tylosin, urdosiol, valproic acid, vanadium, vancomycin HCl, vasopressin, vecuronium bromide, verapamil HCl, vinblastine sulfate, vincristine sulfate, vitamin E/selenium, warfarin sodium, xylazine HCl, yohimbine HCl, zafirlukast, zidovudine (AZT), zinc acetate/zinc sulfate, zonisamide and mixtures thereof.

In one embodiment of the invention, other arylpyrazole compounds such as phenylpyrazoles, as described above in the Background (e.g. fipronil), are known in the art and are suitable for combination with the 1-aryl-5-alkyl pyrazole compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131—each assigned to Merial, Ltd., Duluth, Ga.).

In another embodiment of the invention, nodulisporic acid and its derivatives (a class of known acaricidal, anthelminitic, anti-parasitic and insecticidal agents) can be added to the compositions of the invention. These compounds are used to treat or prevent infections in humans and animals and are described, for example, in U.S. Pat. Nos. 5,399,582 and 5,962,499. The composition can include one or more of the known nodulisporic acid derivatives in the art, including all stereoisomers, such as those described in the literature cited above.

In another embodiment of the invention, one or more macrocyclic lactones, which act as an acaricide, anthelmintic agent and insecticide, can be added to the compositions of the invention. The macrolides are well-known in the art (see e.g. *Macrolides—Chemistry, pharmacology and clinical uses*—edited by Bryskier et al., publ. by Arnette Blackwell, (1993)) and include but are not limited to 12-membered ring macrolides (e.g. methymycin, neomethymycin, YC-17, litorin); 14-membered ring macrolides (e.g. erythromycin A-F, oleandomycin, sporeamicin, roxithromycin, dirithromycin, flurithromycin, clarithromycin, davercin); 15-membered ring macrolides (e.g. azithromycin); 16-membered ring macrolides (e.g. josamycin, kitasamycin, spiramycin, midecamycin, rokitamycin, miokamicin) and 17-membered ring macrolides (e.g. lankadicin).

The macrocyclic lactones also include, but are not limited to, avermectins, such as abamectin, dimadectin, doramectin, emamectin, eprinomectin, ivermectin, latidectin, lepimectin, selamectin and milbemycins, such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131—each assigned to Merial, Ltd., Duluth, Ga. The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag, or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof.

The structure of the avermectins and milbemycins are closely related, e.g., by sharing a complex 16-membered macrocyclic lactone ring; milbemycins lack the glycosidic moiety of the avermectins. The natural product avermectins are disclosed in U.S. Pat. No. 4,310,519 to Albers-Schönberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950, 360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859, 657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos 3,748, 356; 3,818,047; 4,225,598; 4,798,837; 4,751,225, EP 0 179 022 or U.K. 2 140 010 as well as U.S. Pat. Nos. 6,096,329 and 6,685,954 (both assigned to Merial Ltd., Duluth, Ga.). Examples of IGRs suitable for use include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An anthelmintic agent that can be combined with the compound of the invention to form a composition can be a benzenedisulfonamide compound, which includes but is not limited to clorsulon; or a cestodal agent, which includes but is not limited to praziquantel, pyrantel or morantel.

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside.

An insecticidal agent that can be combined with the compound of the invention to form a composition can be a spinosyn (e.g. spinosad) or a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular infection of an insect.

An insecticidal agent that can be combined with the compound of the invention to form a composition can be a semicarbazone, such as metaflumizone (BAS3201).

Metaflumizone is a relatively safe compound (oral LD50> 5,000 mg/kg) with known activity on various Lepidoptera crop pest species.

Where appropriate the anthelmintic, antiparasitic and insecticidal agent may also be selected from the group of compounds described above as suitable for agrochemical use.

In general, the additional pesticidal agent is included in a dose of between about 0.1 µg and about 10 mg. In one embodiment of the invention, the additional pesticidal agent is included in a dose of between about 1 µg and about 10 mg. In another embodiment of the invention, the additional pesticidal agent is included in a dose of about 5 to about 200 µg/kg of weight of animal. In yet another embodiment of the invention, the additional pesticidal agent is included in a dose between about 0.1 to about 10 mg/kg of weight of animal. In still another embodiment of the invention, the additional pesticidal agent is included in a dose between about 0.5 to 50 mg/kg.

The proportions, by weight, of the 1-aryl-5-alkyl pyrazole compound and the additional pesticidal agent are for example between about 5/1 and about 10,000/1. However, one of ordinary skill in the art would be able to select the appropriate ratio of 1-aryl-5-alkyl pyrazole compound and the additional pesticidal agent for the intended host and use thereof.

Method of Synthesizing the Compounds of the Invention

The compounds of formula (I) may be prepared by the application or adaptation of known methods (i.e. methods heretofore used or described in the chemical literature): generally pyrazole ring formation followed where necessary by changing substituents; or methods described in one or more of WO 98/28278 (U.S. Pat. No. 6,350,771), WO 87/03781 (U.S. Pat. No. 5,232,940) and EP 780 378 (U.S. Pat. No. 5,817,688). It will be appreciated by persons skilled in the art that, within aspect of the processes described; the order of the synthetic steps employed may be varied and will depend inter alia on factors such as the nature of other functional groups present in a particular substrate, the availability of key intermediates, and the protecting group strategy (if any) to be adopted (see e.g. "Protective Groups in Organic Synthesis (Third Edition)", eds. Greene and Wuts, Wiley-Interscience, (1999)). Clearly, such factors will also influence the choice of reagents for use in the said synthetic steps.

In one embodiment of the invention, compounds of formula (I) wherein $R_3$ is halomethyl are formed by reaction of the corresponding compounds of formula (I) in which $R_3$ is hydroxymethyl with halogenating reagents, more specifically brominating reagents such as a mixture of bromine or N-bromosuccinimide and triphenylphosphine, hydrobromic acid; or fluorinating reagents such as dimethylaminosulfur trifluoride, diethylaminosulfur trifluoride (DAST™) or bis(2-methoxyethyl)aminosulfur trifluoride (Deoxofluor™). The reaction is usually performed in a solvent such as methylene chloride, chloroform and generally at temperatures between $-100°$ C. and 40° C. A summary of such methods is found in Comprehensive Organic Transformations, VCH Publishers, 1989, R. C. Larock, pp. 353-360.

In another embodiment of the invention, compounds of formula (I) wherein $R_3$ is methyl are formed by reaction of the corresponding compounds of formula (I) in which $R_3$ is halomethyl with reducing reagents such as diisobutyl aluminum hydride (DIBAL-H), lithium aluminum hydride, sodium borohydride or lithium tri-sec-butyl borohydride (L-Selectride™). In one embodiment of the process, the reducing agent is L-Selectride™. The reaction is usually performed in a solvent such as dialkyl ether (e.g. diethyl ether), tetrahydrofuran (THF) and generally at temperatures between about $-100°$ C. and about 40° C. A summary of such methods is found in Comprehensive Organic Transformations, VCH Publishers, 1989, R. C. Larock, pp. 18-21.

According to methods referred to in the chemical literature and in EP 780 378, intermediates of formula (I) wherein $R_3$ is hydroxymethyl are formed by reaction of the corresponding compounds of formula (I) in which $R_3$ is formyl with hydride reagents such as diisobutyl aluminum hydride (DIBAL-H), lithium aluminum hydride, sodium borohydride or lithium tri-sec-butyl borohydride (L-Selectride™). In one embodiment of the process, the hydride agent is sodium borohydride. The reaction may be performed in a solvent such as dialkyl ether (e.g. diethyl ether), tetrahydrofuran (THF), or a hydrocarbon (e.g. hexane or toluene) or mixtures thereof. A temperature of from about $-100$ to about the reflux temperature of the solvent system is generally used. In one embodiment of the process, the temperature is between about 0° C. to about room temperature. A summary of such methods is found in Comprehensive Organic Transformations, VCH Publishers, 1989, R. C. Larock, pp. 527-535. Compounds of formula (I) where $R_3$ is hydroxymethyl are novel, specifically when Z in this formula (I) is C—F, and constitute a further embodiment of the invention.

According to methods described in EP 780 378, intermediates of formula (I) wherein $R_3$ is formyl are formed by oxidative cleavage of the alkene moiety of a compound of formula (II)

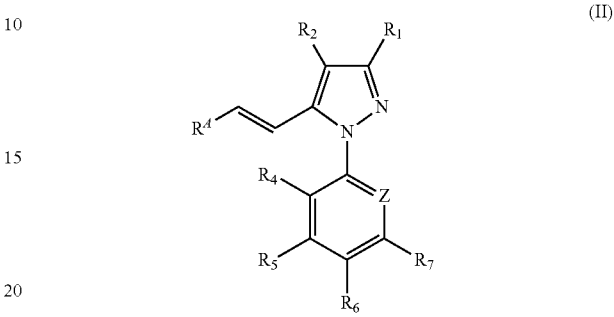

wherein $R^A$ is selected from alkylcarbonyl, alkoxycarbonyl, cyano and nitro to form a compound of formula (IIa):

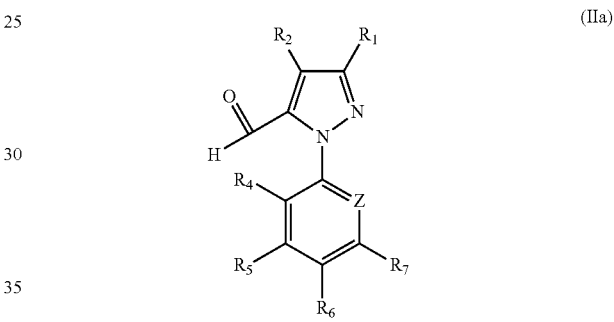

In another embodiment of the process, $R^A$ is selected from $C_1$-$C_4$ alkylcarbonyl, $C_1$-$C_4$ alkoxycarbonyl, cyano and nitro. Such a transformation is well known to those skilled in the art and can be realized for example with ozone, potassium permanganate, sodium metaperiodate. The process may be carried out optionally in a solvent such as methylene chloride, diethylether, chloroform and generally at temperatures between about $-100$ and about 100° C. A summary of such methods is found in Comprehensive Organic Transformations, VCH Publishers, 1989, R. C. Larock, pp. 595-596.

Compound of formula (II) may be prepared by dehydrohalogenation of a compound of formula (III) wherein "halo" represents halogen.

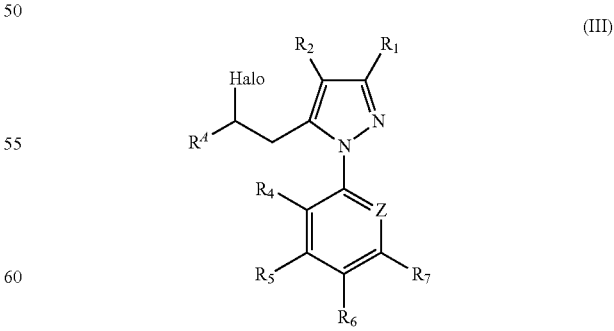

This can be effected by reaction of formula (III) compounds with bases such as triethylamine, sodium hydroxide, potassium hydroxide, lithium diisopropylamide or 1,8-diazabicyclo-[5.4.0]-undec-7-ene (DBU). In one embodiment of the process, the base is DBU. The reaction is carried out optionally with an organic solvent such as dichloromethane, diethylether, tetrahydrofuran, or toluene, and generally between about −100 and about 100° C. depending on the base used. A summary of such methods is found in Comprehensive Organic Transformations, VCH Publishers, 1989, R. C. Larock, pp. 131-132.

Certain compounds of formula (II) and formula (III) are novel, specifically when Z in those formula (II) and (III) is C—F, and as such constitute a further embodiment of the invention. Compounds of formula (III) can be produced from compounds of formula (I), wherein $R_3$ is $NH_2$ (formula (V)):

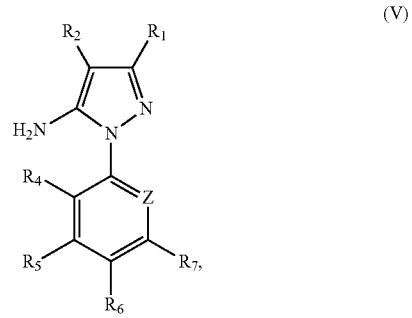

(V)

with an olefin of formula (IV):

(IV)

The process is effected by reaction of a compound of formula (I), wherein $R_3$ is replaced by $NH_2$, in the presence of an alkylnitrite and Copper (II) halide, for example as described in *J. Org. Chem.*, 1977, 42 (14), 2431. Those skilled in the art will recognize this as a Meerwein arylation reaction, as reviewed in *Org. React.*, 1976, 24, 225-259. The process is generally carried out in a mixture of the olefin and a common organic solvent, such as acetonitrile and at a temperature from about −50 and about 100° C. In one embodiment of the process, the temperature is about room temperature.

The compounds of formula (I) in which $R_3$ is replaced by $NH_2$ may be prepared by methods described in one or more of the following: WO 94/21606, WO 93/06089, WO 87/03781; EP 295 117, EP 234 119; U.S. Pat. No. 5,232,940; or by methods known to the skilled in the art. Certain compounds of formula (I) wherein $R_3$ is $NH_2$ are novel, specifically when Z in this formula (I) is C—F, and as such constitute a further embodiment of the invention.

The synthesis of higher oxidation states of compounds of formula (I), i.e. compounds in which m is 1 or 2, can be achieved by oxidation of the corresponding precursor compound of formula (Ibis).

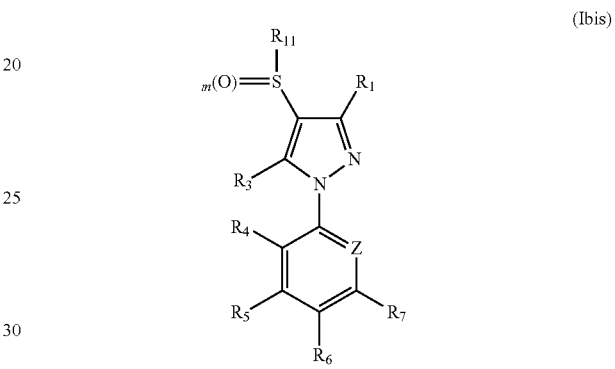

(Ibis)

wherein m is 0 or 1, using conventional oxidizers known in the art.

In one embodiment of the invention, a general reaction scheme for synthesizing the compound of formula (I) can be described as follows:

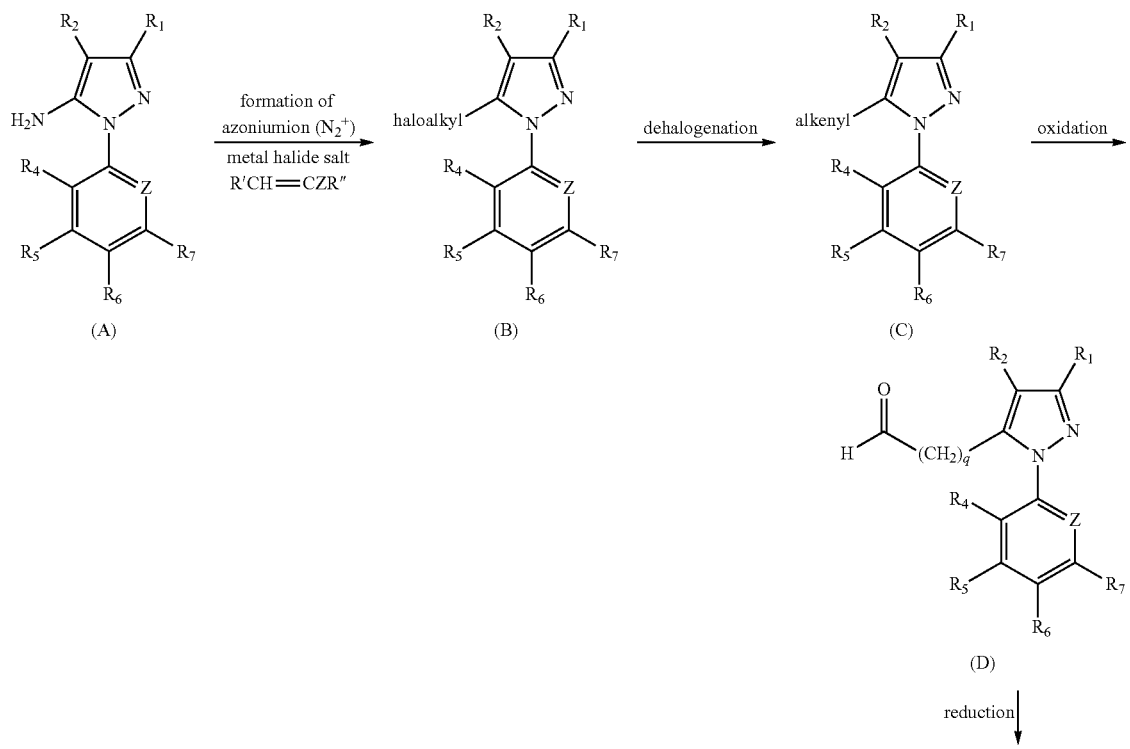

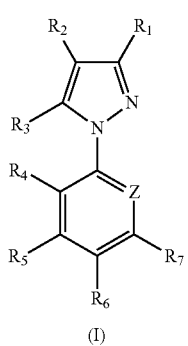
(I)

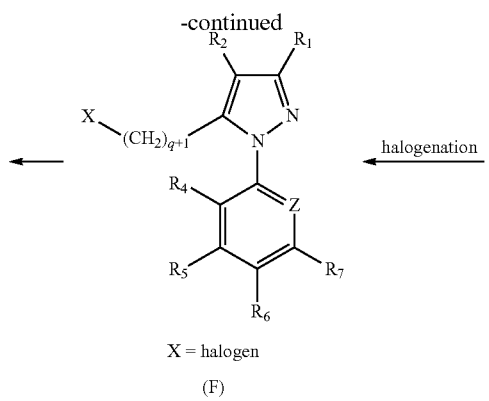
X = halogen
(F)

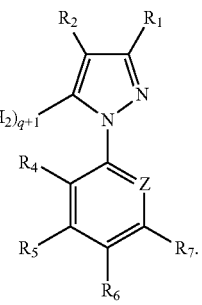
(E)

In one embodiment of the present invention, compounds of formula (I) wherein $R_3$ is ethyl may be prepared by the reaction of the corresponding compounds of formula (I) in which $R_3$ is replaced by vinyl by catalytic hydrogenation, in the presence of a hydrogen source (for example hydrogen gas, sodium hydride, lithium aluminum hydride or sodium borohydride) and one or more catalytic metals (such as cobalt, nickel, palladium, platinum, ruthenium and rhodium). The reaction is generally performed in a solvent such as an alcohol (e.g. ethanol or methanol) and at temperatures between about $-100°$ C. and about $200°$ C. A summary of such methods is found in Comprehensive Organic Transformations, VCH Publishers, 1989, R. C. Larock, pp. 6-8.

Compounds of formula (I) wherein $R_3$ is replaced by vinyl may be prepared by reaction of the corresponding compounds of formula (I) in which $R_3$ is replaced by halogen (e.g. chlorine, iodine or bromine), with vinyltributyltin, in the presence or absence of a base (for example cesium fluoride or cesium carbonate) and with a palladium catalyst such as tetrakis(triphenylphosphine)palladium. The reaction is generally performed in a solvent such an alcohol (e.g. ethanol), a dialkyl ether (e.g. diethyl ether), tetrahydrofuran (THF), or dioxane and at temperatures between about $10°$ C. and about $300°$ C. The reaction may be heated in a sealed tube in a microwave. This transformation is known as a Stille Cross-Coupling reaction and a summary of such methods is found in "Metal-Catalyzed Cross Coupling Reactions", Wiley-VCH publishers, 1998, F. Diedrich and P. J. Stang, chapter 4 by T. N. Mitchell.

Alternative Method of Synthesizing the Compounds of the Invention

Another embodiment of the second aspect of the invention provides a process of making 1-aryl-5-alkyl pyrazole compound of formula (I):

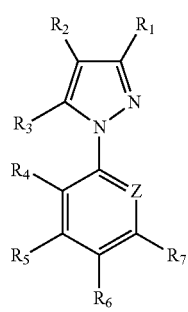
(I)

wherein:
$R_1$ is hydrogen, cyano, halogen, $R_8$, formyl, —C(O)$R_8$, —C(O)O$R_8$, —C(O)NR$_9$R$_{10}$, or —C(S)NH$_2$;

$R_2$ is $R_8$ or —S(O)$_m$R$_{11}$;
$R_3$ is methyl, ethyl or $C_1$-$C_4$ haloalkyl;
$R_4$, $R_5$ and $R_7$ are independently hydrogen, halogen, alkyl, haloalkyl, cyano or nitro;
$R_6$ is halogen, alkyl, haloalkyl, alkoxy, haloalkyloxy, cyano, nitro, —C(O)$R_{12}$, —S(O)$_n$R$_{12}$ or SF$_5$;
Z is a nitrogen atom or C—$R_{13}$;
$R_8$ is alkyl, haloalkyl, cycloalkyl or halocycloalkyl;
$R_9$ is hydrogen, alkyl, haloalkyl or alkoxy;
$R_{10}$ is hydrogen, alkyl, haloalkyl or alkoxy;
$R_{11}$ is alkyl, haloalkyl, alkenyl, haloalkenyl, alkynyl, haloalkynyl or cycloalkyl;
$R_{12}$ is alkyl or haloalkyl;
$R_{13}$ is hydrogen, halogen, cyano, nitro, alkyl, haloalkyl, alkoxy or haloalkoxy;
m is 0, 1 or 2; and
n is 0, 1 or 2; or
a salt thereof
which comprises:
(i) reacting a compound of formula (II):

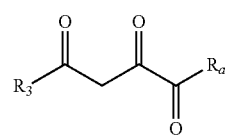
(II)

with a compound of formula $R_2$—Y to produce a compound of formula (III):

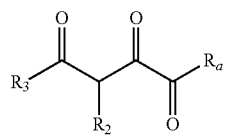
(III)

wherein
$R_a$ is $R_8$, —O—$R_8$ or NR$_9$R$_{10}$
$R_2$, $R_3$ $R_8$, $R_9$ and $R_{10}$ are as defined above and
Y is a leaving group such as halogen
(the di-keto compounds of formula (II) and formula (III) may also exist in their enol form);

(ii) reacting the compound of formula (III) with a compound of formula (Va) or salt thereof:

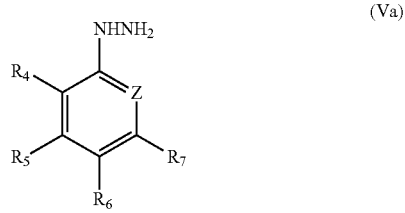

to produce a compound of formula (VI):

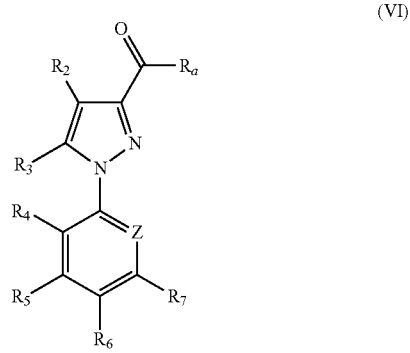

wherein Ra, $R_2$, $R_3$, $R_4$, $R_5$, $R_6$, $R_7$ and Z are as defined below; and (iii) deesterification of the ester moiety of formula (VI), wherein $R_a$ is equal to O—$R_8$ and $R_8$ is defined above, by base catalyzed hydrolysis and subsequent acidification to form the compound corresponding to formula (VIa):

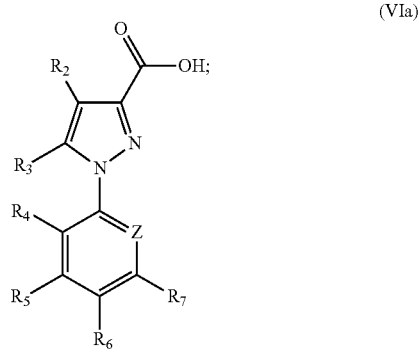

and (iv) derivatizing the compound of formula (VIa) to produce the compound of formula (I).

In a first embodiment of the second aspect of the invention, step (iv) is selected from the group consisting of:
(a) a decarboxylation step;
(b) reacting the compound of formula (VIa) or formula (VI), wherein Ra is equal to halogen such as chloride, with $HNR_9R_{10}$ wherein $R_9$ and $R_{10}$ are as defined above;
(c) (i) reduction of the —$CO_2H$ moiety to —$CH_2OH$;
  (ii) an oxidation step to form —CHO;
  (iii) reaction with a Grignard reagent ($R_8$—Mg-halogen);
  (iv) an additional oxidation step; or
  (ia) reacting the —$CO_2H$ moiety of (VIa) with an agent to form the corresponding N-methoxy-N-methyl amide (Weinreb amide); and
  (iia) reaction with a Grignard reagent ($R_8$—Mg-halogen) or an organolithium reagent ($R_8$—Li).

General ketone formation from Weinreb amides is described in *March's Advanced Organic Chemistry*—Reactions, Mechanisms and Structure (6th Edition), ed. Michael B. Smith and Jerry March, Wiley Interscience (John Wiley & Sons, Inc.), page 1448, (2007).

In a second embodiment of the second aspect of the invention, step (iv) is a decarboxylation of the compound of formula (IIa) to form the compound of formula (I) wherein $R_1$ is hydrogen.

In a third embodiment of the second aspect of the invention, step (iv) is a decarboxylation step followed by a halogenation step to produce the compound of formula (I) wherein $R_1$ is halogen. An example of a general process for decarboxylation followed by halogenations is Morimoto et al, "Synthesis of Halosulfuron-methyl via Selective Chlorination at 3- and/or 5-position of Pyrazole-4-carboxylates", *J. Het. Chem.*, 34: 537-540 (1997).

In a fourth embodiment of the second aspect of the invention, step (iv) comprises reacting the compound of formula (VIa) with $HNR_9R_{10}$, in presence of coupling agents such as dicyclohexylcarbodiimide and the like, wherein $R_9$ and $R_{10}$ are as defined above, to form a compound of formula (I) where $R_1$ is $CONR_9R_{10}$ A general description of this transformation is described in *March's Advanced Organic Chemistry*—Reactions, Mechanisms and Structure (6th Edition), ed. Michael B. Smith and Jerry March, Wiley Interscience (John Wiley & Sons, Inc.), page 1430-1434 (16-74—Acylation of Amines by Carboxylic Acids—Amino-de-hydroxylation), (2007).

In a fifth embodiment of the second aspect of the invention, step (iv) comprises reacting the compound of formula (VI), wherein Ra is equal to halogen such as chloride, with $HNR_9R_{10}$, wherein $R_9$ and $R_{10}$ are as defined above, to form a compound of formula (I) where $R_1$ is $CONR_9R_{10}$ A general description of this transformation is described in *March's Advanced Organic Chemistry*—Reactions, Mechanisms and Structure (6th Edition), ed. Michael B. Smith and Jerry March, Wiley Interscience (John Wiley & Sons, Inc.), page 1427-1429 (16-72—Acylation of Amines by Acyl Halides—Amino-de-halogenation), (2007).

In a sixth embodiment of the second aspect of the invention, step (iv) comprises reacting the compound of formula (VIa) or formula (VI), wherein $R_a$ is equal to halogen such as chloride, with $HNR_9R_{10}$, wherein $R_9$ and $R_{10}$ are both hydrogen, to form a compound of formula (I), where $R_1$ is $CONR_9R_{10}$, and is further reacted with a dehydrating agent such as thionyl chloride, oxalyl chloride and the like, to form the compound of formula (I) wherein $R_1$ is cyano A general description of this transformation is described in *March's Advanced Organic Chemistry*—Reactions, Mechanisms and Structure (6th Edition), ed. Michael B. Smith and Jerry March, Wiley Interscience (John Wiley & Sons, Inc.), page 1549-1550 (17-30—Dehydration of Unsubstituted Amides—N,N-dihydro-C-oxo-bielimination), (2007).

In a seventh embodiment of the second aspect of the invention, step (iv) comprises reacting the amide of formula (VI) wherein $R_a$ is equal to $HNR_9R_{10}$ and $R_9$ and $R_{10}$ are both hydrogen above with 2,4-bis(4-methoxyphenyl)-1,3,2,4-dithiadiphosphetane-2,4-disulfide (known as Lawesson's reagent) and related reagents to form the thioamide of formula (I) wherein $R_1$ is $C(S)NH_2$ A general description of this transformation is described in *March's Advanced Organic Chemistry*—Reactions, Mechanisms and Structure (6th Edition), ed. Michael B. Smith and Jerry March, Wiley Interscience (John Wiley & Sons, Inc.), page 1277-1278 (16-11— The Addition of $H_2S$ and Thiols to Carbonyl Compounds— O-Hydro-C-mercapto-addition), (2007).

In an eighth embodiment of the second aspect of the invention, step (iv) comprises: (i) reduction of the —CO$_2$H moiety in the compound of formula (VIa) to —CH$_2$OH; (ii) oxidation of the —CH$_2$OH moiety to form a —CHO moiety in the compound of formula (IIa); (iii) reaction of the —CHO moiety with a Grignard reagent (R$_8$—Mg-halogen) or an organolithium reagent; and (iv) an additional oxidation step.

In a ninth embodiment of the second aspect of the invention, step (iv) comprises: (i) reduction of the —CO$_2$H moiety in the compound of formula (VIa) to —CH$_2$OH; (ii) oxidation of the —CH$_2$OH moiety to form a —CHO moiety in the compound of formula (IIa); (iii) reaction of the —CHO moiety with a Grignard reagent (R$_8$—Mg-halogen) or an organolithium reagent; and (iv) additional reduction steps of the hydroxyl moiety to yield the compound of formula (I) wherein R$_1$ is R$_8$ is formed The alternative process of making 1-aryl-5-alkyl pyrazole compound of formula (I) differs with the process described above in that the latter process derivatives an aryl pyrazole compound to form the alkyl moieties at R$_3$. However, the alternative process is directed toward the formation of a pyrazole ring which already has the alkyl moieties of R$_3$ attached. The subsequent process steps involve the derivatization of the moiety at the R$_1$ position. The described invention is a more elegant process that uses fewer process steps which require handling the larger aryl pyrazole structure, i.e. derivatization is mostly achieved by working with smaller sized compounds which are then later combined to form the larger aryl pyrazole structure.

Alternatively, a tenth embodiment of the second aspect of the invention provides a process of making 1-aryl-3,4,5-trisubstituted pyrazole compound of formula (I):

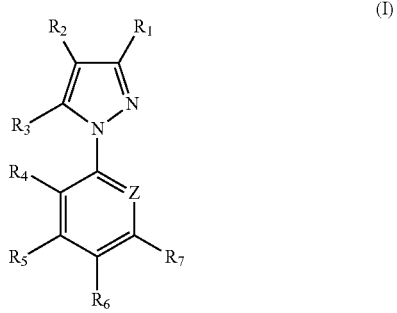

(i) reacting the compound of formula (III) with hydrazine or salt thereof to form the compound of formula (IV):

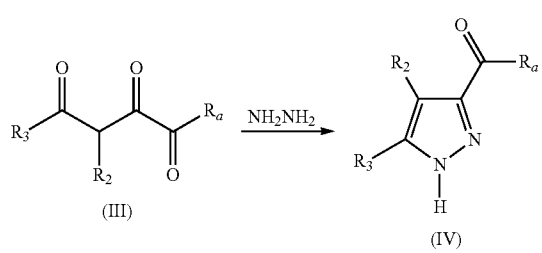

wherein R$_a$, R$_2$ and R$_3$ have the above meanings; and (iii) reacting the compound of formula (IV) with the compound of formula (Vb) wherein L is a leaving group to form the compound of formula (VI):

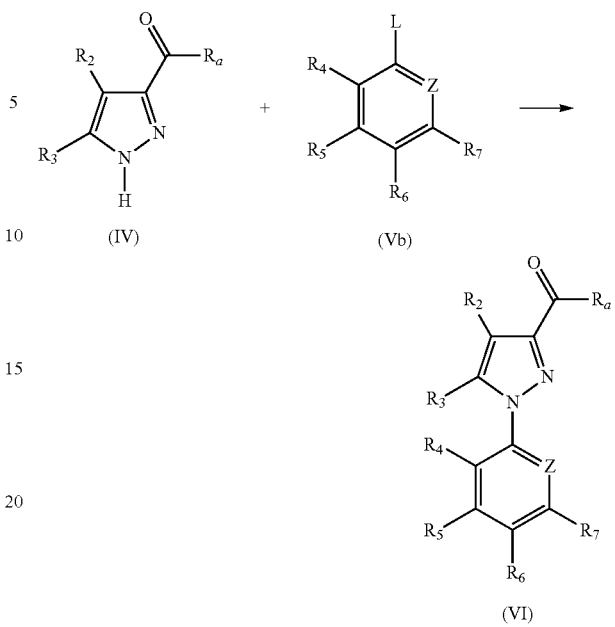

wherein R$_a$, R$_2$, R$_3$, R$_4$, R$_5$, R$_6$, R$_7$ and Z have the above meanings and L is a leaving group (suitable leaving groups include but are not limited to halogen, trifluoromethane sulfonyl, methanesulfonyl, toluenesulfonyl and the like);

(iv) optionally, subjecting the compound of formula (VI) to functional group modification with the —C(=O)R$_a$ moiety.

An eleventh embodiment of the second aspect of the invention is that the process for preparing the 1-aryl-3,4,5-trisubstituted pyrazoles of formula (I) produces high yield. In one embodiment of the third aspect of the invention, the yield is from about 55% to about 95% (for both alternative processes of the invention)

A twelfth embodiment of the second aspect of the invention of the invention is to provide a process for preparing 1-aryl-3,4,5-trisubstituted pyrazoles from 1,3-diketones with excellent regioselectivity. In one embodiment of the fourth aspect of the invention, the regioselectivity of the formation of the compound of formula (VI) from the compound of formula (III) is from about 70% to about +99%

A thirteenth embodiment of the second aspect of the invention is to further derivatize the compounds of formula (I) by functional group transformation.

A fourteenth embodiment of the second aspect of the invention, the functional group transformation correspond to step (iv) of the first aspect of the invention.

A fifteenth embodiment of the second aspect of the invention, where R$_1$ is a —C(O)OR$_8$ is further derivatized to form R$_1$ as CN via a four step process wherein step one comprises reacting a compound of formula (VIb) with a base and subsequent acidification to form a compound of formula (VIa), step two comprises reacting a compound of formula (VIa) and a halogenating agent to form a compound of formula (VIc), step three comprises reacting a compound of formula (VIc) with an amino base to form the compound of formula (VId) and step three comprises reacting a compound of formula (VId) with a dehydrating agent such as SOCl$_2$ to form the compound of formula (I). One example of this transformation is depicted in the reaction scheme below:

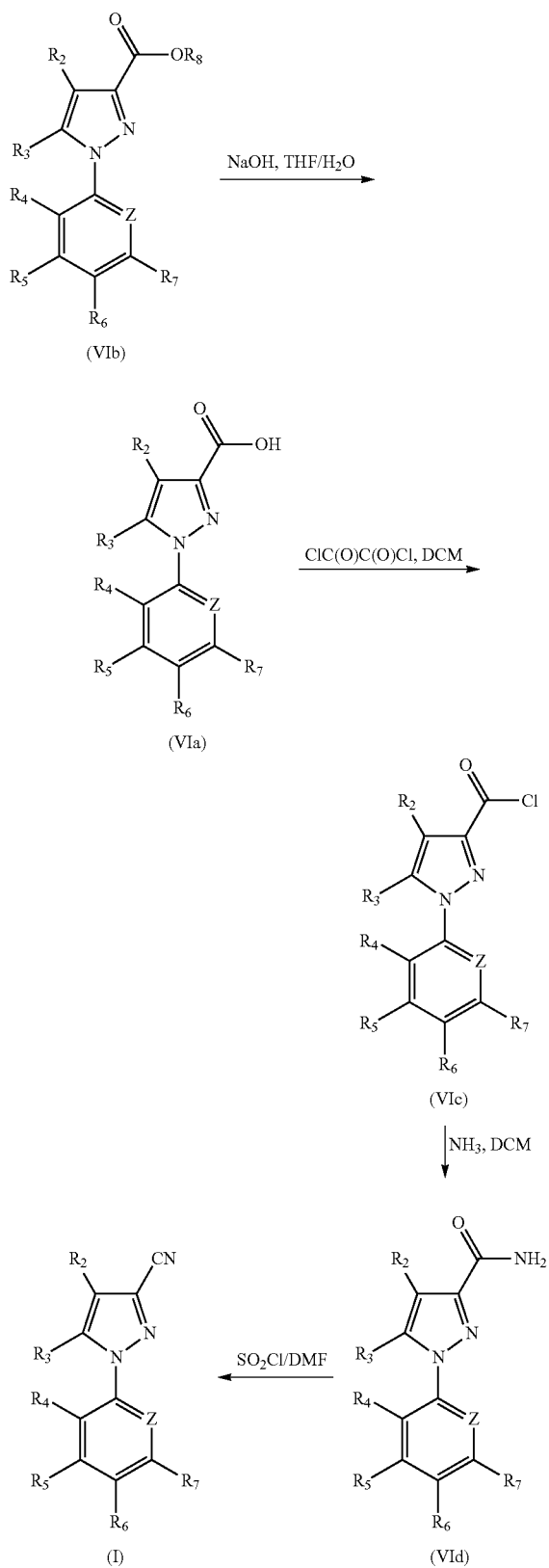

(VIb)

(VIa)

(VIc)

(I)

(VId)

A sixteenth embodiment of the second aspect of the invention, where $R_2$ is —$S(O)_mR_{11}$ and m is 0 or 1, the sulfur is oxidized to form —$S(O)_mR_7$ where m is 1 and 2 respectively.

A seventeenth aspect of the invention is to prepare 1,3-dicarbonyl compounds by reacting a compound of formula (II) with a compound $R_2$—Y to form a compound of formula (III)—see equation below:

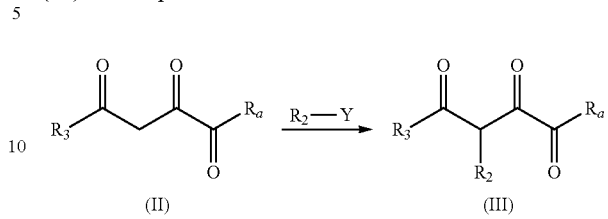

wherein $R_a$, $R_2$, $R_3$ and Z have the above meanings. (The di-keto compounds of formula (II) and formula (III) may also exist in their enol form). Advantageously, $R_2$ is —$S(O)_mR_{11}$.

An eighth aspect of the invention is to prepare compounds of formula (IV) by reacting a compound of formula (III) with a hydrazine to form the compounds of formula (IV)—see equation below:

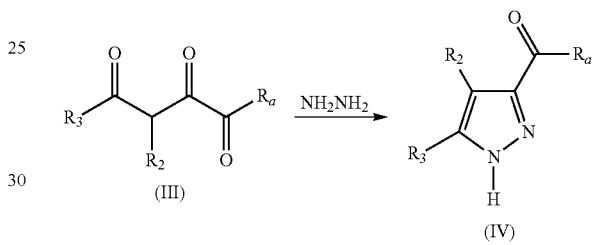

wherein $R_a$, $R_2$, and $R_3$ have the above meanings.

The acids, bases and solvents and the individual process steps such as alkylation, Grignard reaction/reagents, halogenation and oxidation used in the invention will be apparent to those of ordinary skill in the art (e.g. *Vogel's Textbook of Practical Organic Chemistry* (Fifth Edition), Furniss et al., Longman Scientific & Technical (1989); *Protective Groups in Organic Synthesis* (Third Edition), Greene & Wuts, Wiley Interscience (1999); *March's Advanced Organic Chemistry: Reactions, Mechanisms, and Structure* (6$^{th}$ Edition), March & Smith, Wiley, (2007); *Advanced Organic Chemistry (Part A—Structure and Mechanisms—4$^{th}$ Edition)*, Carey & Sundberg, Springer Science (2000); *Advanced Organic Chemistry (Part B—Reaction and Synthesis—4$^{th}$ Edition)*, Carey & Sundberg, Springer Science (2001); *Strategic Applications of Named Reactions in Organic Synthesis*, Kurti and Czako, Academic Press (2005).

Appropriate solvents for the process of reacting the compound of formula (II) with the compound of formula $R_2$—Z to form the compound of formula (III) include but are not limited to tetrahydrofuran, dimethylformamide, halogenated hydrocarbons or mixtures thereof.

Appropriate bases for the process of reacting the compound of formula (II) with the compound of formula $R_2$—Z to form the compound of formula (III) include but are not limited to metal hydride, metal bis(trimethylsilyl)amide, alkylamines such as trialkylamine, hydroxides such as metal hydroxides and alkoxides such as metal alkoxides.

Appropriate temperatures for the process of reacting the compound of formula (II) with the compound of formula $R_2$—Z to form the compound of formula (III) range from about −50 to about 50° C.

Appropriate solvents for the process of reacting the compound of formula (IV) with the compound of formula (V), or a salt thereof, to form the compound of formula (I) include but are not limited to alcohols such as methanol, ethanol, propanol, isopropanol, butanol; water; tetrahydrofuran; dimethylamino formate; halogenated hydrocarbons or mixtures thereof.

Appropriate additives for the process of reacting the compound of formula (IV) with the compound of formula (V), or a salt thereof, to form the compound of formula (I) include but are not limited to acidic compounds such as hydrogen halide, sulfuric acid, nitric acid and carboxylic acid.

Appropriate temperatures for the process of reacting the compound of formula (IV) with the compound of formula (V), or a salt thereof, to form the compound of formula (I) range from about −20 to about 100° C.

Method of Treatment, Dosage Ranges and Routes of Administration

The invention is also directed toward a method of treating an animal (e.g. a mammal or bird), against ectoparasitic infection by administering an ectoparasiticidally effective amount of the composition of the invention. Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

In another embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola.*

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites mosquitoes, flies, lice, blowfly and combinations thereof. Specific examples include but are not limited to cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dematobia* sp., *Cochliomyia* sp., and the like). In yet another embodiment for the treatment against ectoparasites, the ectoparasite is a flea and/or tick.

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabici* and *Psoroptes ovis*. The above list is not exhaustive and other ectoparasites are well known in the art to be harmful to animals and humans. These include, for example migrating dipterous larvae.

When an anthelmintic agent is added to the composition of the invention, the composition can also be used to treat against endoparasites such as those helminths selected from the group consisting of *Anaplocephala, Ancylostoma, Anecator, Ascaris, Capillaria, Cooperia, Dirofilaria, Echinococcus, Enterobius, Fasciola, Haemonchus, Oesophagostumum, Ostertagia, Toxocara, Strongyloides, Toxascaris, Trichinella, Trichuris,* and *Trichostrongylus.*

In addition with or without the addition of other pesticidal agents added to the composition, the invention can also be used to treat other pests which include but are not limited to pests:

(1) from the order Isopoda, for example *Oniscus asellus, Armadillidium vulgare* and *Porcellio scaber;*

(2) from the order Diplopoda, for example *Blaniulus guttulatus;*

(3) from the order Chilopoda, for example *Geophilus carpophagus* and *Scutigera* spp.;

(4) from the order Symphyla, for example *Scutigerella immaculata;*

(5) from the order Thysanura, for example *Lepisma saccharina;*

(6) from the order Collembola, for example *Onychiurus armatus;*

(7) from the order Orthoptera, for example *Acheta domesticus, Gryllotalpa* spp., *Locusta migratoria migratorioides, Melanoplus* spp. and *Schistocerca gregaria;*

(8) from the order Blattaria, for example *Blatta orientalis, Periplaneta americana, Leucophaea maderae* and *Blattella germanica;*

(9) from the order Dermaptera, for example *Forficula auricularia;*

(10) from the order Isoptera, for example *Reticulitermes* spp.;

(11) from the order Phthiraptera, for example *Pediculus humanus corporis, Haematopinus* spp., *Linognathus* spp., *Trichodectes* spp. and *Damalinia* spp.;

(12) from the order Thysanoptera, for example *Hercinothrips femoralis, Thrips tabaci, Thrips palmi* and *Frankliniella accidentalis;*

(13) from the order Heteroptera, for example *Eurygaster* spp., *Dysdercus intermedius, Piesma quadrata, Cimex lectularius, Rhodnius prolixus* and *Triatoma* spp.;

(14) from the order Homoptera, for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

(15) from the order Lepidoptera, for example *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Helicoverpa* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea peffionella, Hofmannophila pseudospretella, Cacoecia podana, Capua reticulana, Choristoneura fumiferana, Clysia ambiguella, Homona magnanima, Tortrix viridana* and *Cnaphalocerus* spp.;

(16) from the order Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,*

*Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;*

(17) from the order Hymenoptera, for example *Diprion* spp., *Hoplocampa* spp., *Lasius* spp., *Monomorium pharaonis* and *Vespa* spp.;

(18) from the order Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.;

(19) from the order Siphonaptera, for example *Xenopsylla cheopis* and *Ceratophyllus* spp.;

(20) from the class of arachnids, for example *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.; and

(21) the plant-parasitic nematodes, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti.*

It is furthermore possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Dicono-*

*coris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Caffigypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcathella* spp., *Metopolophium dirhodum, Moneffia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifoffi.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porceffio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*mycoplasma*-like organisms) and RLO (*rickettsia*-like organisms). If appropriate, they can also be employed as intermediates or precursors for the synthesis of other active compounds.

In another embodiment this aspect of the invention, the compounds and compositions of the invention are suitable for controlling pests such as insects selected from the group consisting of *Blattella germanica, Heliothis virescens, Leptinotarsa decemlineata, Tetramorium caespitum* and combinations thereof.

In each aspect of the invention, the compounds and compositions of the invention can be applied against a single pest or combinations thereof.

The composition containing the 1-aryl-5-alkyl pyrazole of the invention may be administered continuously, for treatment or prophylaxis, by known methods. Generally, a dose of from about 0.001 to about 50 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In one treatment embodiment, the treatment is carried out so as to administer to the animal, on a single occasion, a dose containing between about 0.001 and about 100 mg/kg of a 1-aryl-5-alkyl pyrazole compound or between about 0.1 and about 200 µg/kg or about 100 µg/kg of compound. In another treatment embodiment, the treatment is via a direct topical administration such as a paste, pour-on, ready-to-use, spot-on, etc. type formulation. Higher amounts may be provided for very prolonged release in or on the body of the animal. In another treatment embodiment, the amount of 1-aryl-5-alkyl pyrazole compound for birds and animals which are small in size is greater than about 0.01 mg, and in another embodiment for the treatment of small sized birds and animals, the amount of 1-aryl-5-alkyl pyrazole compound is between about 1 and about 100 mg/kg of weight of animal.

The solutions according to the invention may be applied using any means known per se, e.g. using an applicator gun or a metering flask.

This method serves to cleanse the skin and the hairs of the animals by eliminating the parasites which are present thereon, as well as their residues and dejections. The result of this is that the animals are no longer stressed by the parasites and their bites, this having positive consequences, for example on their growth and on the use of their food ration.

In one embodiment, a direct pour-on skin formulation according to the present invention can provide long-lasting and broad-spectrum efficacy when the solution is applied to the animal's back, e.g. along the line of the back at one or more points.

According to a first embodiment for administering direct pour-on formulations, the process comprises applying the solution to the animals, the application being repeated every month or every two months.

According to a second embodiment for administering direct pour-on formulation, the process comprises applying the solution to livestock animals before they arrive in the Feed Lot, it being possible for this application to be the final one before the animals are slaughtered.

Obviously, the process may also consist in combining these two embodiments, namely the first followed by the second.

In another embodiment, the compounds of the invention are administered in spot-on formulations. While not wishing to be bound by theory, it is believed that these formulations work by dissolution of the dose in the natural oils of the host's skin, fur or feathers. From there, the active agent(s) distribute around the host's body through the sebaceous glands of the skin. The therapeutic agent also remains in the sebaceous glands. Thus, the glands provide a natural reservoir for the active agent that allows for the agent to be drained back out to the follicles to reapply itself to the skin and hair. This, in turn, provides for longer time periods between application as well as eliminating the need to re-administer the dose after the host becomes wet because of rain, bathes, etc. The inventive formulation has the further advantage of not being directly deposited on the skin or fur, where self-grooming animals could orally ingest the therapeutic agent, thereby becoming sick or possibly interacting with other therapeutic agent being orally administered.

In one embodiment of the location of administration, a single formulation containing the active agent in a substantially liquid carrier and in a form which makes possible a single application, or an application repeated a small number of times, will be administered to the animal over a localized region of the animal, e.g. between the two shoulders. In one embodiment of the invention, the localized region has a surface area of about 10 cm² or larger. In another embodiment of the invention, the localized region has a surface are of between about 5 and about 10 cm² area.

The invention is further described by the following non-limiting examples which further illustrate the invention, and are not intended, nor should they be interpreted to, limit the scope of the invention.

EXAMPLES

Preparation Examples

All temperatures are given in degrees Centigrade; room temperature means 20 to 25° C. Reagents were purchased from commercial sources or prepared following literature procedures.

Unless otherwise noted, purification by reverse phase column chromatography was performed by dissolving the crude residue in a small volume of DMSO and filtering through a 0.45 micron (nylon disc) syringe filter. The solution was then purified on an HPLC purification system managed by the Chromeleon™ software using a 50 mm Varian Dynamax HPLC 21.4 mm Microsorb Guard-8 C8 column. The initial MeOH:H$_2$O solvent mixture was selected as appropriate for the target compound. This initial mixture was maintained for 0.5 minutes then changed by a linear gradient to a final concentration of 100% MeOH over 5 minutes. 100% MeOH was maintained for 2 more minutes. Total run time was 8 minutes. The resulting fractions were analyzed, combined as appropriate, and then evaporated to provide purified material.

Proton and fluorine magnetic resonance (respectively 1H NMR and 19F NMR) spectra were recorded on a Varian INOVA NMR spectrometer [400 MHz (1H) and 377 MHz (19F)]. All spectra were determined in the solvents indicated. Chemical shifts are reported in ppm downfield of tetramethylsilane (TMS), referenced to the residual proton peak of the respective solvent peak for 1H NMR. Interproton coupling constants are reported in Hertz (Hz). LC-MS spectra were obtained using a Thermofinnigan AQA MS ESI instrument, using a Phenomenex Aqua 5 micron C18 125 A 50×4.60 mm column and a linear gradient from 55% MeOH: 1% CH3CN in H2O to 100% MeOH over 3 minutes. 100% MeOH was maintained for 2 minutes. Melting points were determined using a Thomas Hoover capillary melting point apparatus and are uncorrected.

Example 1

3-Cyano-1-(2,6-dichloro-4-trifluoromethylphenyl)-5-methyl-4-trifluoromethylthiopyrazole (compound No 1)

A solution of L-selectride (14.2 mL, 1M in THF) was added to a solution of 5-bromomethyl-3-cyano-1-(2,6-dichloro-4-trifluoromethylphenyl)-4-trifluoromethylthiopyrazole (6.75 g) in THF at −78° C. The reaction mixture was allowed to warm to room temperature with stirring over one hour, and then hydrogen peroxide (2.6 mL, 30% w/v) was added followed by water and ethyl acetate. The organic layer was separated, dried over anhydrous magnesium sulfate, filtered and concentrated under reduced pressure. The crude product was purified by chromatography (SiO$_2$, heptane/EA) to afford the title compound as a white solid (3.67 g, 65%). MS (ES): M/Z [M+NH$_4$]=437. 1H NMR: (400 MHz, DMSO-d$_6$): 2.30 (s, 3H) and 8.39 (s, 2H). 19F NMR (376 MHz, DMSO-d$_6$): −44.03 (s, 3F) and −61.98 (s, 3F).

The starting material, 5-bromomethyl-3-cyano-1-(2,6-dichloro-4-trifluoromethylphenyl)-4-trifluoromethylthiopyrazole, was prepared as follows:

a. A solution of 5-amino-3-cyano-1-(2,6-dichloro-4-trifluoromethylphenyl)-4-trifluoro-methylthiopyrazole (87.5 g), prepared as described in EP-A-0 295 117, was added dropwise to a suspension of tert-butylnitrite (32 mL), methyl acrylate (149 mL) and copper bromide (55.6 g) in acetonitrile. The reaction mixture was stirred overnight. The resulting mixture was diluted with diethylether and washed with water. The organic layer was dried over anhydrous magnesium sulfate, filtered and concentrated under reduced pressure. Trituration of the residue from ethyl acetate and heptane gave 5-(2'-bromo-2'-carbomethoxy)ethyl-3-cyano-1-(2,6-dichloro-4-trifluoromethyl-phenyl)-4-trifluoromethylthiopyrazole as a tanned solid (73.7 g, 78%).

b. 1,8-diazabicyclo-[5.4.0]-undec-7-ene (4.4 mL) was added to a solution of 5-(2'-bromo-2'-carbomethoxy)ethyl-3-cyano-1-(2,6-dichloro-4-trifluoromethylphenyl)-4-trifluoromethylthiopyrazole (15.1 g) dissolved in toluene. After stirring for 40 minutes, the mixture was diluted with ethyl acetate, washed with water, 10% aqueous hydrochloric acid solution and water. The organic phase was dried over anhydrous magnesium sulfate, filtered and concentrated under reduced pressure to give 3-cyano-1-(2,6-dichloro-4-trifluoromethylphenyl)-5-(E-2-methoxycarbonylethenyl)-4-trifluoromethylthiopyrazole as a white solid (11.0 g 85%).

c. Ozone was bubbled through a solution of the 3-cyano-1-(2,6-dichloro-4-trifluoromethylphenyl)-5-(E-2-methoxycarbonyl-ethenyl)-4-trifluoromethylthiopyrazole (4.8 g) in dichloromethane and methanol for 3 h at −78° C. After 3 hours the intensely blue solution was decolorized with oxygen gas, and then treated with dimethylsulfide at −78° C. This reaction mixture was allowed to warm to room temperature whereupon the mixture was washed with a 10% aqueous solution of sodium bisulfate. The resulting mixture was extracted with ethyl acetate. The organic layer was dried over anhydrous magnesium sulfate, filtered and concentrated under reduced pressure to give 3-cyano-1-(2,6-dichloro-4-trifluoromethylphenyl)-5-formyl-4-trifluoromethylthiopyrazole as a white solid (4.2 g).

d. 3-Cyano-1-(2,6-dichloro-4-trifluoromethylphenyl)-5-formyl-4-trifluoromethylthiopyrazole (4.2 g) was dissolved in absolute ethanol and sodium borohydride (0.61 g) added portion wise at 0° C. This reaction mixture was stirred and allowed to warm to room temperature over 2 h whereupon water was added. The resulting mixture was extracted with ethyl acetate. The organic layer was dried over anhydrous magnesium sulfate, filtered and concentrated under reduced pressure to give a residue that was purified by chromatography (SiO$_2$, heptane/EA) to afford 3-cyano-1-(2,6-dichloro-4-trifluoromethylphenyl)-5-hydroxymethyl-4-trifluoromethylthiopyrazole as a white solid (4.03 g, 94%).

e. Bromine (2.8 mL) was slowly added to a solution of triphenylphosphine (12 g) in dichloromethane. After stirring for 30 minutes, it was transferred via syringe to a solution of 3-cyano-1-(2,6-dichloro-4-trifluoromethylphenyl)-5-hydroxymethyl-4-trifluoromethylthiopyrazole (9 g) in dichloromethane. After stirring for 2 hours, solvent was evaporated under reduced pressure. The residue was purified by chromatography (SiO$_2$, heptane/EA) to afford 5-bromomethyl-3-cyano-1-(2,6-dichloro-4-trifluoromethylphenyl)-4-trifluoromethylthiopyrazole as a pale yellow solid (9.9 g, 96%).

Example 2

1-(2-Chloro-6-fluoro-4-trifluoromethylphenyl)-3-cyano-5-methyl-4-trifluoromethylthiopyrazole (compound No 7)

Using a procedure similar to that described in Example 1, except starting from 5-amino-3-cyano-1-(2-chloro-6-fluoro-4-trifluoromethylphenyl)-4-trifluoro-methylthiopyrazole, the title compound was isolated as a white solid. 1H NMR: (400 MHz, DMSO-d$_6$): 2.34 (s, 3H) and 8.27 (m, 2H). 19F NMR (376 MHz, DMSO-d$_6$): −43.96 (s, 3F), −62.08 (s, 3F) and −115.04 (s, 1F).

The 5-amino-3-cyano-1-(2-chloro-6-fluoro-4-trifluoromethylphenyl)-4-trifluoro-methylthiopyrazole was prepared as follows:

a. N-Chlorosuccinimide (4.1 g) was added to a solution of 2-fluoro-4-trifluoromethylaniline in acetonitrile under nitrogen and the mixture heated to 75° C. over night. The mixture was concentrated, diluted with ether, washed with water, saturated sodium bicarbonate solution and brine. The organic layers were dried over anhydrous magnesium sulfate, filtered and concentrated under reduced pressure to give 2-chloro-6-fluoro-4-trifluoromethylaniline as a liquid (5.9 g). Rf=0.6 (2:8 EA/heptane); 1H NMR: (400 MHz, CDCl$_3$) 4.41 (bs, 2H); 7.20 (dd, 1H, J=10.5, 1.5 Hz) and 7.36 (s, 1H). 19F NMR (376 MHz, CDCl$_3$): −130.78 (s, 1F) and −61.98 (s, 3F).

b. A solution of 2-chloro-6-fluoro-4-trifluoromethylaniline (5 g) in acetic acid was added dropwise to a suspension of nitrosyl sulphuric acid (11.2 g) in acetic acid at 15° C. After stirring for 1 hour, this reaction mixture was added dropwise to a suspension of 1,2-dicyano-3-hydroxyprop-2-ene potassium salt (10 g) and sodium acetate trihydrate (32 g) in a mixture of sodium acetic and water at 7° C. After stirring for 1 hour, this reaction mixture was diluted with water and extracted with dichloromethane. The organic layers were stirred vigorously with a 30% ammonium hydroxide solution for 10 minutes, separated, dried over anhydrous magnesium sulfate, filtered and concentrated under reduced pressure to give a residue that was purified by chromatography (SiO$_2$, heptane/EA) to afford 5-amino-1-(2-chloro-6-fluoro-4-trifluoromethylphenyl)-3-cyanopyrazole as a yellow-orange solid (5.1 g, 71%). R$_f$=0.25 (3:7 EA/heptane); 1H NMR (400 MHz, DMSO-d$_6$): 5.94 (s, 1H), 6.14 (s, 2H) and 8.06-8.10 (m, 2H). 19F NMR (376, DMSO-d$_6$): −61.98 (s, 3F) and −114.38 (s, 1F).

The 1,2-dicyano-3-hydroxyprop-2-ene potassium salt was prepared as follows:

A solution of potassium tert-butoxide (29 g) in tert-butanol was added dropwise to a solution of succinonitrile (20 g) and ethyl formate (22.7 g) in a 5:1 mixture of toluene and tert-butanol at 5° C. After stirring for 6 hours, the solid was filtered off, washed once with ethanol and three times with methyl tert-butyl ether and then dried over night in a vacuum oven at 55° C. to give 1,2-dicyano-3-hydroxyprop-2-ene potassium salt as a tan solid (35 g, 96%).

c. A solution of 5-amino-1-(2-chloro-6-fluoro-4-trifluoromethylphenyl)-3-cyanopyrazole (3 g) in dichloromethane was stirred at 0° C. and treated dropwise with a solution of trifluoromethylsulphenyl chloride (2 g) in dichloromethane during 1 hour. After stirring overnight at room temperature, nitrogen was bubbled trough the solution for 5 minutes. Then the mixture was washed with water, saturated sodium bicarbonate solution and brine. The organic layers were dried over anhydrous magnesium sulfate, filtered and concentrated under reduced pressure to give a residue that was purified by chromatography (SiO$_2$, heptane/EA) to afford 5-amino-1-(2-chloro-6-fluoro-4-trifluoromethylphenyl)-3-cyano-4-trifluoromethylthiopyrazole as a white solid (3.5 g, 86%). R$_f$=0.4 (3:7 EA/heptane); 1H NMR (400 MHz, DMSO-d$_6$) 7.21 (bs, 2H) and 8.10-8.14 (m, 2H). 19F NMR (376 MHz, DMSO-d$_6$): −45.33 (s, 3F), −62.08 (s, 3F) and −114.62 (s, 1F).

Example 3

3-Cyano-1-(2-fluoro-4-trifluoromethylphenyl)-5-methyl-4-trifluoromethylthiopyrazole (compound No 13)

Using a procedure similar to that described in Example 1, except starting from 5-amino-3-cyano-1-(2-fluoro-4-trifluoromethylphenyl)-4-trifluoromethylthiopyrazole, the title compound was isolated as a white solid. 1H NMR: (400 MHz, DMSO-$d_6$): 2.38 (s, 3H), 7.89 (d, 1H), 8.05 (t, 1H) and 8.16-8.19 (m, 1H). 19F NMR (376 MHz, DMSO-$d_6$): −43.68 (s, 3F), −61.86 (s, 3F) and −119.69 (m, 1F).

The starting material, 5-amino-3-cyano-1-(2-fluoro-4-trifluoromethylphenyl)-4-trifluoro-methylthiopyrazole, was prepared from 2-fluoro-4-trifluoromethylaniline following a similar procedure to that described in Example 2, steps b,c.

Example 4A 1-(2-Chloro-6-fluoro-4-trifluoromethylphenyl)-3-cyano-4-dichlorofluoromethylthio-5-methylpyrazole (compound No 26)

Using a procedure similar to that described in Example 1, except starting from 5-amino-1-(2-chloro-6-fluoro-4-trifluoromethylphenyl)-3-cyano-4-dichlorofluoromethylthiopyrazole, the title compound was isolated as a white solid. MS (ES): M/Z [M+H+CH$_3$OH]=468. 1H NMR: (400 MHz, CDCl$_3$): 2.34 (s, 3H), 7.57 (dd, J=8.3, 1.4 Hz 1H) and 7.74 (bs, 1H). 19F NMR (376 MHz, CDCl$_3$): −21.10 (s, 1F), −63.78 (s, 3F) and −113.47 (d, J=8.3 Hz, 1F).

The starting material, 5-amino-1-(2-chloro-6-fluoro-4-trifluoromethylphenyl)-3-cyano-4-dichlorofluoromethylthiopyrazole, was prepared by the following procedure:

a. Sulfur monochloride (0.78 g) was added at 10° C. to a dichloromethane solution of 5-amino-1-(2-chloro-6-fluoro-4-trifluoromethylphenyl)-3-cyanopyrazole (3.54 g), described in Example 2 step b. After stirring overnight at room temperature, nitrogen was bubbled trough the solution for 5 minutes. The solid precipitate was filtered, washed with dichloromethane, heptane and dried under reduced pressure to give 5-amino-1-(2-chloro-6-fluoro-4-trifluoromethylphenyl)-3-cyanopyrazol-4-yl disulfide as a pale yellow solid (2.8 g, 72%). $R_f$=0.3 (4:6 EA/heptane)

b. Sodium dithionite (6.2 g), disodium hydrogen phosphate (4.3 g) and fluorotrichloromethane (5.2 g) were added with stirring to a solution of 5-amino-1-(2-chloro-6-fluoro-4-trifluoromethylphenyl)-3-cyanopyrazol-4-yl disulfide (5.15 g) in a 2:1 mixture of N,N-dimethylformamide and water at 15° C. After stirring for one hour, the mixture was poured into ice and stirred for 30 minutes. The solid was filtered off, washed with water and dried to give 5-amino-1-(2-chloro-6-fluoro-4-trifluoromethylphenyl)-3-cyano-4-dichlorofluoromethylthiopyrazole as a white solid (4.1 g, 64%). $R_f$=0.4 (3:7 EA/heptane).

Example 4B 1-(2-Chloro-6-fluoro-4-trifluoromethylphenyl)-3-cyano-4-dichlorofluoromethylthio-5-methylpyrazole (compound No 26—alternative method)

a. Sodium hydroxide (1.65 M, 250 mL)) was added to a solution of 1-(2-chloro-6-fluoro-4-trifluoromethylphenyl)-3-ethoxycarbonyl-5-methyl-4-fluorodichloromethylthiopyrazole (66.0 g) in ethanol (750 mL) and THF (100 mL). After stirring 60 minutes, a six normal aqueous hydrochloric acid solution (70 mL) was slowly added. The mixture was concentrated and the residue dissolved up into 500 mL ethyl acetate and washed with saturated sodium bicarbonate solution, water and then brine. The organic phase was dried over anhydrous sodium sulfate, filtered and concentrated under reduced pressure to give a light yellow solid residue that was used in the next step without further purification. MS (ES): M/Z [M+H]=455. 1H NMR (400 MHz, CDCl$_3$): 7.79 (s, 2H), 6.66 (s, 1H) and 2.18 (s, 3H). 19F NMR (376 MHz, CDCl$_3$): −20.35 (s, 1F), −63.74 (s, 3F) and −113.34 (d, J=7.9 Hz, 1F).

b. Oxalyl chloride (35 mL) was added dropwise to a mixture of the above residue in dichloromethane (350 mL) cooled in an ice bath. Three drops of N,N-dimethylformamide was added and the mixture removed from the ice bath. After two hours stirring, solvent was evaporated under reduced pressure to give a solid residue that was dissolved in dichloromethane and cooled to 0° C. Dry ammonia gas was bubbled through the reaction mixture for 5 minutes before allowing the reaction mixture to warm to room temperature. After stirring for one hour, the mixture was concentrated to a crude solid which was washed with water and dried to give an off white solid residue that was used in the next step without further purification. Rf=0.25 (3:7 EA/heptane). 1H NMR (400 MHz, CDCl$_3$): 7.72 (s, 1H), 7.54 (d, J=8.0 Hz, 1H) and 2.36 (s, 3H). 19F NMR (376 MHz, CDCl$_3$): −20.35 (s, 1F), −63.74 (s, 3F) and −113.32 (d, J=7.9 Hz, 1F).

c. Oxalyl chloride (42 mL) was added dropwise to a stirred solution of N,N-dimethylformamide (36 mL) in acetonitrile (500 mL) at 0° C. After stirring for 10 minutes, a solution of the above residue in acetonitrile (400 mL) and N,N-dimethylformamide (20 mL) was added dropwise and the reaction mixture was stirred 1 h. allowing it to warm to room temperature. The reaction mixture was poured rapidly into stirring ice water and the resulting solid filtered, washed with water and dried to give the title compound as a white solid (57.0 g, 96%). Rf=0.75 (3:7 EA/heptane). MS (ES): M/Z [M+H]=436. Elemental analysis: Calculated: C, 35.76, H, 1.15, N, 9.62, S, 7.34, Cl, 24.36 and F, 21.76. Found: C, 35.88, H, 1.15, N, 9.53, S, 7.39, Cl, 24.29 and F, 21.80. 1H NMR (500 MHz, CD$_2$Cl$_2$): 7.77 (s, 1H), 7.60 (d, J=8.3 Hz, 1H) and 2.34 (s, 3H). 19F NMR (470 MHz, CD$_2$Cl$_2$): −21.43 (s, 1F), −64.17 (s, 3F) and −114.35 (d, J=8.4 Hz, 1F). 13C NMR (126 MHz, CD$_2$Cl$_2$): 159.04 (d, J=259.9 Hz, 1C), 151.10 (s, 1C), 135.90 (s, 1C), 135.51 (qd, J=34.9, 8.8 Hz, 1C), 134.21 (s, 1C), 128.00 (d, J=15.2 Hz, 1C), 124.18 (q, J=3.3 Hz, 1C), 122.60 (qd, J=273.5, 3.0 Hz, 1C), 121.58 (d, J=334.1 Hz, 1C), 114.09 (dq, J=23.0, 3.6 Hz, 1C), 112.14 (s, 1C), 110.75 (s, 1C), 10.81 (s, 1C), The starting material, 1-(2-chloro-6-fluoro-4-trifluoromethylphenyl)-3-ethoxycarbonyl-4-dichlorofluoromethylthio-5-methylpyrazole, was prepared as follows:

A 1.1 normal ethanolic solution of hydrochloric acid (115 mL) was added to a solution of 2-chloro-6-fluoro-4-trifluoromethylphenylhydrazine (24 g) in 200 mL ethanol cooled in an ice bath. Ethyl 3-dichlorofluoromethylthio-2,4-dioxovalerate (38.4 g) was added and the resulting mixture stirred overnight allowing it to warm to room temperature. The mixture was concentrated by removing 150 mL ethanol, cooled to approximately 0° C. in an ice bath and the solid precipitate filtered and washed with cold ethanol to afford 1-(2-chloro-6-fluoro-4-trifluoromethylphenyl)-3-ethoxycarbonyl-5-methyl-pyrazole as a white solid (34.5 g, 68%). Rf=0.65 (3:7

EA/heptane). MS (ES): M/Z [M+H]=483. 1H NMR (400 MHz, CDCl$_3$): 7.70 (s, 1H), 7.52 (dd, J=8.3, 1.7 Hz, 1H), 4.47 (m, 2H), 2.33 (s, 3H) and 1.42 (t, J=7.1 Hz, 3H). 19F NMR (376 MHz, CDCl$_3$): −20.36 (s, 1F), −63.74 (s, 3F) and 113.24 (d, J=8.6 Hz, 1F).

Ethyl 3-dichlorofluoromethylthio-2,4-dioxovalerate used above was prepared as follows:

Triethylamine (5.5 mL, 4.0 g) was added at 0° C. to a solution of ethyl-2,4-dioxovalerate (5 mL, 5.6 g) in 125 mL dichloromethane. After stirring for 10 minutes, a solution of dichlorofluoromethyl sulfenyl chloride (4 mL, 6.8 g from Marshallton, King, N.C.—USA) in 30 mL dichloromethane was added dropwise at 0° C. After stirring 30 minutes at approximately 0° C. the mixture was let stirred at room temperature overnight and then was concentrated under reduce pressure, dissolved in ethyl acetate, filtered and concentrated to give an oily residue that was purified by chromatography (SiO$_2$, heptane/EA) to afford ethyl 3-dichlorofluoromethylthio-2,4-dioxovalerate as a pale yellow liquid (7.5 g, 81%). 1H NMR (400 MHz, CD$_2$Cl$_2$): 4.35 (q, J=7.2 Hz, 2H), 2.51 (s, 3H) and 1.34 (t, J=7.1 Hz, 3H). 19F NMR (376 MHz, CD$_2$Cl$_2$): −21.67 (s, 1F).

Another alternative procedure was used to prepare 1-(2-chloro-6-fluoro-4-trifluoromethylphenyl)-3-ethoxycarbonyl-4-dichlorofluoromethylthio-5-methylpyrazole:

Potassium carbonate (100 mg) was added as a solid to a solution of 4-dichlorofluoromethylthio-3-ethoxycarbonyl-5-methyl-1-H-pyrazole (100 mg) and 3-chloro-4,5-difluorobenzotrifluoride (110) in N-methylpyrrolidinone (2 mL). The mixture in sealed tube was heated to 100° C. for 10 min with a microwave synthesis system (CEM, Matthews, N.C.—USA) then cooled to room temperature and filtered over a pad of celite. The filtrate was concentrated under reduced pressure to give a residue that was purified by chromatography (SiO$_2$, heptane/EA) to afford 1-(2-chloro-6-fluoro-4-trifluoromethylphenyl)-3-ethoxycarbonyl-5-methyl-pyrazole as a white solid (51 mg, 30%).

Preparation of 4-dichlorofluoromethylthio-3-ethoxycarbonyl-5-methyl-1-H-pyrazole used above is described below.

A 1.1 normal ethanolic solution of hydrochloric acid (32 mL) was added to a solution of hydrazine (1.25 g, 1.23 mL) in 100 mL ethanol cooled in an ice bath. Ethyl 3-dichlorofluoromethylthio-2,4-dioxovalerate (9.3 g) was added and the resulting mixture stirred overnight allowing it to warm to room temperature. The mixture was concentrated and the residue dissolved up into ethyl acetate, washed with saturated sodium bicarbonate solution and then brine. The organic layer was dried over anhydrous sodium sulfate, filtered and concentrated under reduced pressure to give a residue that was purified by chromatography (SiO$_2$, heptane/EA) to afford 4-dichlorofluoromethylthio-3-ethoxycarbonyl-5-methyl-1-H-pyrazole as a white solid (8.0 g, 87%). Rf=0.5 (1:1 EA/heptane). 1H NMR (400 MHz, CDCl$_3$): 12.64 (br s, 1H), 4.43 (q, 2H), 2.50 (s, 3H) and 1.39 (t, 3H, CH$_3$). 1H NMR (400 MHz, DMSO-d6): 13.92 (br s, 1H), 4.28 (q, 2H), 2.53 (s, 3H) and 1.28 (t, 3H). 19F NMR (376 MHz, DMSO-d6): −153.31 (s, 1F).

Example 5

3-Cyano-4-dichlorofluoromethylthio-1-(2,6-dichloro-4-trifluoromethylphenyl)-5-methylpyrazole (compound No 15)

Using a procedure similar to that described in Example 1, except starting from 5-amino-3-cyano-1-(2,6-dichloro-4-trifluoromethylphenyl)-4-dichlorofluoromethylthiopyrazole, the title compound was isolated as a white solid. MS (ES): M/Z [M+H+CH$_3$OH]=485. 1H NMR: (400 MHz, DMSO-d$_6$): 2.31 (s, 3H) and 8.39 (s, 2H). 19F NMR (376 MHz, DMSO-d$_6$): −20.88 (s, 1F) and −61.97 (s, 3F).

The starting material, 5-amino-3-cyano-1-(2,6-dichloro-4-trifluoromethylphenyl)-4-dichlorofluoromethylthiopyrazole, was prepared following a similar procedure to that described in Example 4, steps a,b, from 5-amino-3-cyano-1-(2,6-dichloro-4-trifluoromethylphenyl)pyrazole that itself, was prepared using a similar procedure to that described in Example 2, steps b,c from 2,6-dichloro-4-trifluoromethylyaniline.

Example 6

3-Cyano-1-(2,6-dichloro-4-trifluoromethoxyphenyl)-5-methyl-4-trifluoromethylthiopyrazole (compound No 17)

Using a procedure similar to that described in Example 1, except starting from 5-amino-3-cyano-1-(2,6-dichloro-4-trifluoromethoxyphenyl)-4-trifluoromethylthiopyrazole, described in EP-A-0 295 117, the title compound was isolated as a white solid. MS (ES): M/Z [M+H]=436. 1H NMR: (400 MHz, DMSO-d$_6$): 2.29 (s, 3H) and 8.08 (s, 2H). 19F NMR (376 MHz, DMSO-d$_6$): −44.09 (s, 3F) and −57.41 (s, 3F).

Example 7

3-Cyano-4-dichlorofluoromethylthio-1-(2,6-dichloro-4-trifluoromethoxyphenyl)-5-methylpyrazole (compound No 23)

Using a procedure similar to that described in Example 1, except starting from 5-amino-3-cyano-4-dichlorofluoromethylthio-1-(2,6-dichloro-4-trifluoromethoxyphenyl)pyrazole, the title compound was isolated as a white solid. MS (ES): M/Z [M+NH$_4$]=485. 1H NMR: (400 MHz, CDCl$_3$): 2.30 (s, 3H) and 7.44 (s, 2H). 19F NMR (376 MHz, CDCl$_3$): −20.99 (s, 1F) and −58.28 (s, 3F).

The starting material, 5-amino-3-cyano-4-dichlorofluoromethylthio-1-(2,6-dichloro-4-trifluoromethoxyphenyl) pyrazole, was prepared following a similar procedure to that described in Example 4, steps a,b, from 5-amino-3-cyano-1-(2,6-dichloro-4-trifluoromethoxyphenyl)pyrazole that itself, was prepared from 2,6-dichloro-4-trifluoromethoxyaniline using a similar procedure to that described in Example 2, steps b,c.

Example 8

1-(2-Chloro-4-trifluoromethylphenyl)-3-cyano-4-dichlorofluoromethylthio-5-methylpyrazole (compound No 27)

Using a procedure similar to that described in Example 1, except starting from 5-amino-1-(2-chloro-4-trifluoromethylphenyl)-3-cyano-4-dichlorofluoromethylthiopyrazole, the title compound was isolated as a white solid. 1H NMR: (400 MHz, CDCl$_3$): 2.35 (s, 3H), 7.63 (d, J=8.2 Hz, 1H), 7.78 (dd, J=8.2, 1.4 Hz, 1H) and 7.91 (d, J=1.5 Hz, 1H). 19F NMR (376 MHz, CDCl$_3$): −21.10 (s, 1F), −63.78 (s, 3F) and −113.47 (d, J=8.3 Hz, 1F).

The starting material, 5-amino-1-(2-chloro-4-trifluoromethylphenyl)-3-cyano-4-dichlorofluoromethylthiopyrazole, was prepared following a similar procedure to that described in Example 4, steps a,b from 5-amino-1-(2-chloro-4-trifluoromethylphenyl)-3-cyanopyrazole that, itself, was prepared from 2-chloro-4-trifluoromethylaniline using a similar procedure to that described in Example 2, steps b,c.

Example 9

3-Cyano-1-(2,6-dichloro-4-pentafluorothiophenyl)-5-methyl-4-trifluoromethylthiopyrazole (compound No 34)

Using a procedure similar to that described in Example 1, except starting from 5-amino-3-cyano-1-(2,6-dichloro-4-pentafluorothiophenyl)-4-trifluoromethylthiopyrazole, the title compound was isolated as a white solid. 1H NMR: (400 MHz, CDCl$_3$): 2.31 (s, 3H) and 7.96 (s, 2H). 19F NMR (376 MHz, CDCl$_3$): −44.10 (s, 3F), 62.68 (d, J=152 Hz, 4F) and 78.16-79.77 (quintet, J=154 Hz, 1F).

5-amino-3-cyano-1-(2,6-dichloro-4-pentafluorothiophenyl)-4-trifluoromethylthiopyrazole, was prepared from 4-pentafluorothioaniline following a similar procedure to that described in Example 2, steps a, b, c, except that 2.2 equivalents of N-chlorosuccinimide were used in step a.

Example 10

4-Chlorodifluoromethylthio-1-(2-chloro-6-fluoro-4-trifluoromethylphenyl)-3-cyano-5-methylpyrazole (compound No 36)

Using a procedure similar to that described in Example 1, except starting from 5-amino-1-(2-chloro-6-fluoro-4-trifluoromethylphenyl)-4-chlorodifluoromethylthio-3-cyanopyrazole, the title compound was isolated as a white solid. MS (ES): M/Z [M+NH$_4$] 437. 1H NMR: (400 MHz, CDCl$_3$): 2.33 (s, 3H), 7.56 (dd, J=8.3, 1.4 Hz 1H) and 7.74 (bs, 1H). 19F NMR (376 MHz, CDCl$_3$): −63.79 (s, 3F), −113.48 (d, J=8.4 Hz, 1F) and −161.99 (s, 2F).

The starting material, 5-amino-1-(2-chloro-6-fluoro-4-trifluoromethylphenyl)-4-chlorodifluoromethylthio-3-cyanopyrazole, was prepared following the same procedure to that described in Example 4, steps a,b, except that bromochlorodifluoromethane was used in step b instead of fluorotrichloromethane.

Example 11

3-Cyano-4-dichlorofluoromethylthio-1-(2,6-dichloro-4-pentafluorothiophenyl)-5-methylpyrazole (compound No 42)

Using a procedure similar to that described in Example 1, except starting from 5-amino-3-cyano-4-dichlorofluoromethylthio-1-(2,6-dichloro-4-pentafluorothiophenyl)pyrazole, the title compound was isolated as a white solid. 1H NMR: (400 MHz, CDCl$_3$): 2.31 (s, 3H) and 7.96 (s, 2H). 19F NMR (376 MHz, CDCl$_3$): −21.03 (s, 1F), 62.70 (d, J=152 Hz, 4F) and 78.19-79.81 (quintet, J=154 Hz, 1F).

The starting material, 5-amino-3-cyano-4-dichlorofluoromethylthio-1-(2,6-dichloro-4-pentafluorothiophenyl) pyrazole, was prepared following a similar procedure to that described in Example 4, steps a,b from 5-amino-3-cyano-1-(2,6-dichloro-4-pentafluorothiophenyl)pyrazole that, itself, was prepared using a similar procedure to that described in Example 2, steps a,b from 4-pentafluorothioaniline, except that 2.2 equivalents of N-chlorosuccinimide were used in step a.

Example 12

3-cyano-1-(2,6-difluoro-4-trifluoromethylphenyl)-5-methyl-4-trifluoromethylthiopyrazole (compound No 6)

Cesium fluoride (2.7 g) was added to a solution of 3-cyano-1-(2,6-dichloro-4-trifluoromethylphenyl)-5-methyl-4-trifluoromethylthiopyrazole (0.7 g) in N-methylpyrolidinone. The reaction mixture was heated at 100° C. overnight. The reaction mixture was then cooled to room temperature and water was added. The resulting mixture was extracted with ethyl acetate. The organic layer was dried over anhydrous magnesium sulfate, filtered and concentrated under reduced pressure to give a residue that was purified by chromatography (SiO$_2$, heptane/EA) to afford the title compound as a white solid (0.38 g, 59%). 1H NMR: (400 MHz, CDCl$_3$): 2.38 (s, 3H) and 7.49 (d, J=8 Hz, 2H). 19F NMR (376 MHz, CDCl$_3$): −43.83 (s, 3F), −63.91 (s, 3F) and −113.98 (d, J=7 Hz, 2F).

Preparation of 3-cyano-1-(2,6-dichloro-4-trifluoromethylphenyl)-5-methyl-4-trifluoromethylthiopyrazole is described in Example 1.

Example 13

1-(2-chloro-6-methyl-4-trifluoromethylphenyl)-3-cyano-5-methyl-4-trifluoromethylthiopyrazole (compound No 43)

A solution of trimethylboroxine (83 mg), tris(dibenzylideneacetone)dipalladium (10 mg), Xantphos (18 mg), potassium carbonate (165 mg) and 3-cyano-1-(2,6-dichloro-4-trifluoromethylphenyl)-5-methyl-4-trifluoromethylthiopyrazole (250 mg) in dioxane was heated in a microwave for 20 minutes at 130° C. in a 10 ml sealed Pyrex glass tube. The reaction mixture was cooled to room temperature then diluted with ethyl acetate and filtered over Celite. The organic filtrate was washed with water, dried over anhydrous magnesium sulfate, filtered and concentrated under reduced pressure to give a residue that was purified by chromatography (SiO$_2$, heptane/EA) to afford the title compound as a white solid. MS (ES): M/Z [M+NH$_4$]=417. 1H NMR: (400 MHz, CDCl$_3$): 2.13 (s, 3H), 2.26 (s, 3H), 7.60 (bs, 1H) and 7.73 (bs, 1H). 19F NMR (376 MHz, CDCl$_3$): −44.25 (s, 3F) and −63.63 (s, 3F).

Preparation of 3-cyano-1-(2,6-dichloro-4-trifluoromethylphenyl)-5-methyl-4-trifluoromethylthiopyrazole is described in Example 1.

Example 14

3-cyano-1-(2,6-dichloro-4-trifluoromethylphenyl)-5-methyl-4-trifluoromethylsulfinylpyrazole (compound No 5)

A 30 wt % aqueous solution of hydrogen peroxide (29 μL) was added to a trifluoroacetic acid solution of 3-cyano-1-(2,6-dichloro-4-trifluoromethylphenyl)-5-methyl-4-trifluoromethylthiopyrazole (116 mg) described in Example 1. The reaction mixture was stirred overnight whereupon solvent was evaporated under reduced pressure to give a residue that was purified by chromatography (SiO$_2$, heptane/EA) to afford the title compound as a white solid (100 mg, 83%). MS (ES): M/Z [M+NH$_4$]=453. 1H NMR: (400 MHz, DMSO-d$_6$):

2.35 (s, 3H) and 8.41 (s, 2H). 19F NMR (376 MHz, DMSO-$d_6$): −62.01 (s, 3F) and −74.18 (s, 3F).

Example 15

1-(2-Chloro-6-fluoro-4-trifluoromethylphenyl)-3-cyano-5-methyl-4-trifluoromethylsulfinylpyrazole (compound No 9)

Using a procedure similar to that described in Example 14, except starting from 1-(2-chloro-6-fluoro-4-trifluoromethylphenyl)-3-cyano-5-methyl-4-trifluoromethylthiopyrazole described in Example 2, the title compound was isolated as a white solid. 1H NMR: (400 MHz, CDCl$_3$): 2.45 (bs, 3H), 7.59 (d, J=8.3 Hz, 1H) and 7.76 (s, 1H). 19F NMR (376 MHz, CDCl$_3$): −63.84 (s, 3F), −73.85 (d, 3F) and −113.29 (dd, 1F).

Example 16

3-Cyano-1-(2,6-difluoro-4-trifluoromethylphenyl)-5-methyl-4-trifluoromethylsulfinylpyrazole (compound No 12)

Using a procedure similar to that described in Example 14, except starting from 3-cyano-1-(2,6-difluoro-4-trifluoromethylphenyl)-5-methyl-4-trifluoromethylthiopyrazole described in Example 12, the title compound was isolated as a white solid. 1H NMR: (400 MHz, CDCl$_3$): 2.50 (s, 3H) and 7.51 (d, 2H). 19F NMR (376 MHz, CDCl$_3$): −63.96 (s, 3F), −73.63 (s, 3F) and −114.52 to −114.76 (d, 2F).

Example 17

3-Cyano-1-(2-fluoro-4-trifluoromethylphenyl)-5-methyl-4-trifluoromethylsulfinylpyrazole (compound No 14)

Using a procedure similar to that described in Example 14, except starting from 3-cyano-1-(2-fluoro-4-trifluoromethylphenyl)-5-methyl-4-trifluoromethylthiopyrazole described in Example 3, the title compound was isolated as a white solid.

Example 18

3-Cyano-1-(2,6-dichloro-4-trifluoromethoxyphenyl)-5-methyl-4-trifluoromethylsulfinylpyrazole (compound No 19)

Using a procedure similar to that described in Example 14, except starting from 3-cyano-1-(2,6-dichloro-4-trifluoromethoxyphenyl)-5-methyl-4-trifluoromethylthiopyrazole described in Example 6, the title compound was isolated as a white solid. MS (ES): M/Z [M+H] 452. 1H NMR: (400 MHz, DMSO-$d_6$): 2.34 (s, 3H) and 8.10 (m, 2H). 19F NMR (376 MHz, DMSO-$d_6$): −57.40 (s, 3F) and −74.24 (s, 3F).

Example 19

3-Cyano-4-dichlorofluoromethylsulfinyl-1-(2,6-dichloro-4-trifluoromethylphenyl)-5-methylpyrazole (compound No 20)

Using a procedure similar to that described in Example 14, except starting from 3-cyano-4-dichlorofluoromethylthio-1-(2,6-dichloro-4-trifluoromethylphenyl)-5-methylpyrazole described in Example 5, the title compound was isolated as a white solid. MS (ES): M/Z [M+NH$_4$] 485. 1H NMR: (400 MHz, DMSO-$d_6$): 2.39 (s, 3H) and 8.40 (s, 2H). 19F NMR (376 MHz, DMSO-$d_6$): −61.99 (s, 3F) and −64.05 (s, 1F).

Example 20

3-Cyano-4-dichlorofluoromethylsulfinyl-1-(2,6-dichloro-4-trifluoromethoxyphenyl)-5-methylpyrazole (compound No 24)

Using a procedure similar to that described in Example 14, except starting from 3-cyano-4-dichlorofluoromethylthio-1-(2,6-dichloro-4-trifluoromethoxyphenyl)-5-methylpyrazole described in Example 7, the title compound was isolated as a white solid. MS (ES): M/Z [M+NH$_4$] 501. 1H NMR: (400 MHz, CDCl$_3$): 2.43 (s, 3H) and 7.45 (s, 2H). 19F NMR (376 MHz, CDCl$_3$): −58.25 (s, 3F) and −63.02 (s, 1F).

Example 21

1-(2-Chloro-6-fluoro-4-trifluoromethylphenyl)-3-cyano-4-dichlorofluoromethylsulfinyl-5-methylpyrazole (compound No 29)

Using a procedure similar to that described in Example 14, except starting from 1-(2-chloro-6-fluoro-4-trifluoromethylphenyl)-3-cyano-4-dichlorofluoromethylthio-5-methylpyrazole described in Example 4, the title compound was isolated as a white solid. MS (ES): M/Z [M+NH$_4$] 469. 1H NMR: (400 MHz, CDCl$_3$): 2.39 (s, 3H), 7.51 (d, 1H) and 7.68 (s, 1H). 19F NMR (376 MHz, CDCl$_3$): −63.00 to −63.06 (d, 1F), −63.82 (s, 3F) and −113.01 to −113.30 (m, 1F).

Example 22

1-(2-Chloro-4-trifluoromethylphenyl)-3-cyano-4-dichlorofluoromethylsulfinyl-5-methylpyrazole (compound No 30)

Using a procedure similar to that described in Example 14, except starting from 4-chlorodifluoromethylthio-1-(2-chloro-6-fluoro-4-trifluoromethylphenyl)-3-cyano-5-fluoromethylpyrazole described in Example 8, the title compound was isolated as a white solid. 1H NMR: (400 MHz, CDCl$_3$): 2.47 (s, 3H), 7.63 (d, 1H), 7.80 (d, 1H) and 7.93 (s, 1H). 19F NMR (376 MHz, CDCl$_3$): −62.97 (bs, 1F), −63.54 (s, 3F).

Example 23

4-Chlorodifluoromethylsulfinyl-1-(2-chloro-6-fluoro-4-trifluoromethylphenyl)-3-cyano-5-methylpyrazole (compound No 37)

Using a procedure similar to that described in Example 14, except starting from 4-chlorodifluoromethylthio-1-(2-chloro-6-fluoro-4-trifluoromethylphenyl)-3-cyano-5-methylpyrazole described in Example 10, the title compound was isolated as a white solid. MS (ES): M/Z [M+NH$_4$] 453. 1H NMR: (400 MHz, CDCl$_3$): 2.46 (s, 3H), 7.59 (dd, J=8.3, 1.5 Hz 1H) and 7.76 (bs, 1H). 19F NMR (376 MHz, CDCl$_3$): −60.68 to −62.28 (m, 2F), −63.83 (s, 3F) and −112.99 to 113.31 (m, 1F).

Example 24

1-(2-Chloro-6-methyl-4-trifluoromethylphenyl)-3-cyano-5-methyl-4-trifluoromethylsulfinylpyrazole (compound No 44)

Using a procedure similar to that described in Example 14, except starting from 1-(2-chloro-6-methyl-4-trifluoromethylphenyl)-3-cyano-5-methyl-4-trifluoromethylthiopyrazole described in Example 13, the title compound was isolated as a white solid. MS (ES): M/Z [M+NH$_4$] 433. 1H NMR: (400 MHz, CDCl$_3$): 2.15 (s, 3H), 2.38 (s, 3H), 7.63 (bs, 1H) and 7.74 (bs, 1H). 19F NMR (376 MHz, CDCl$_3$): −63.67 (s, 3F) and −73.96 (s, 3F).

Example 25

3-cyano-1-(2,6-dichloro-4-trifluoromethylphenyl)-5-methyl-4-trifluoromethylsulfonylpyrazole (compound No 4)

Sodium periodate (20 mg) and ruthenium chloride (3 mg) were added to a solution of 3-cyano-1-(2,6-dichloro-4-trifluoromethylphenyl)-5-methyl-4-trifluoromethylthiopyrazole (100 mg), that is described in Example 1, in a mixture of acetonitrile-water (4:1). The reaction mixture was stirred overnight whereupon the mixture was diluted with ethyl acetate and filtered over silica gel. The organic filtrate was washed with water, dried over anhydrous magnesium sulfate, filtered over Celite and concentrated under reduced pressure to give the title compound as a white solid (73 mg, 68%). MS (ES): M/Z [M+H]=452. 1H NMR: (400 MHz, DMSO-d$_6$): 2.46 (s, 3H) and 7.87 (s, 2H). 19F NMR (376 MHz, DMSO-d$_6$): −63.77 (s, 3F) and −79.83 (s, 3F).

Example 26

1-(2-Chloro-6-fluoro-4-trifluoromethylphenyl)-3-cyano-4-dichlorofluoromethylsulfonyl-5-methylpyrazole (compound No 31)

Using a procedure similar to that described in Example 25, except starting from 1-(2-chloro-6-fluoro-4-trifluoromethylphenyl)-3-cyano-4-dichlorofluoromethylthio-5-methylpyrazole described in Example 4, the title compound was isolated as a white solid. 1H NMR: (400 MHz, CDCl$_3$): 2.50 (bs, 3H), 7.61 (d, J=8.3 Hz, 1H) and 7.78 (bs, 1H). 19F NMR (376 MHz, CDCl$_3$): −63.77 (bs, 1F), −63.84 (s, 3F) and −112.96 (bs, 1F).

Example 27

4-Chlorodifluoromethylsulfonyl-1-(2-chloro-6-fluoro-4-trifluoromethylphenyl)-3-cyano-5-methylpyrazole (compound No 39)

Using a procedure similar to that described in Example 25, except starting from 4-chlorodifluoromethylthio-1-(2-chloro-6-fluoro-4-trifluoromethylphenyl)-3-cyano-5-methylpyrazole described in Example 10, the title compound was isolated as a white solid. MS (ES): M/Z [M+NH$_4$] 469. 1H NMR: (400 MHz, CDCl$_3$): 2.49 (s, 3H), 7.60-7.63 (m, 1H) and 7.78 (bs, 1H). 19F NMR (376 MHz, CDCl$_3$): −63.86 (s, 3F), −64.87 (s, 2F) and −112.92 (m, 1F).

Example 28

3-Cyano-4-dichlorofluoromethylsulfonyl-1-(2,6-dichloro-4-trifluoromethylphenyl)-5-methylpyrazole (compound No 41)

Using a procedure similar to that described in Example 25, except starting from 3-cyano-4-dichlorofluoromethylthio-1-(2,6-dichloro-4-trifluoromethylphenyl)-5-methylpyrazole described in Example 5, the title compound was isolated as a white solid. MS (ES): M/Z [M+NH$_4$] 501. 1H NMR: (400 MHz, DMSO-d$_6$): 2.50 (s, 3H) and 8.44 (s, 2H). 19F NMR (376 MHz, DMSO-d$_6$): −62.04 (s, 3F) and −65.19 (s, 1F). The reaction scheme below depicts application of the general reaction scheme to synthesize compounds of Examples 1, 14 and 25.

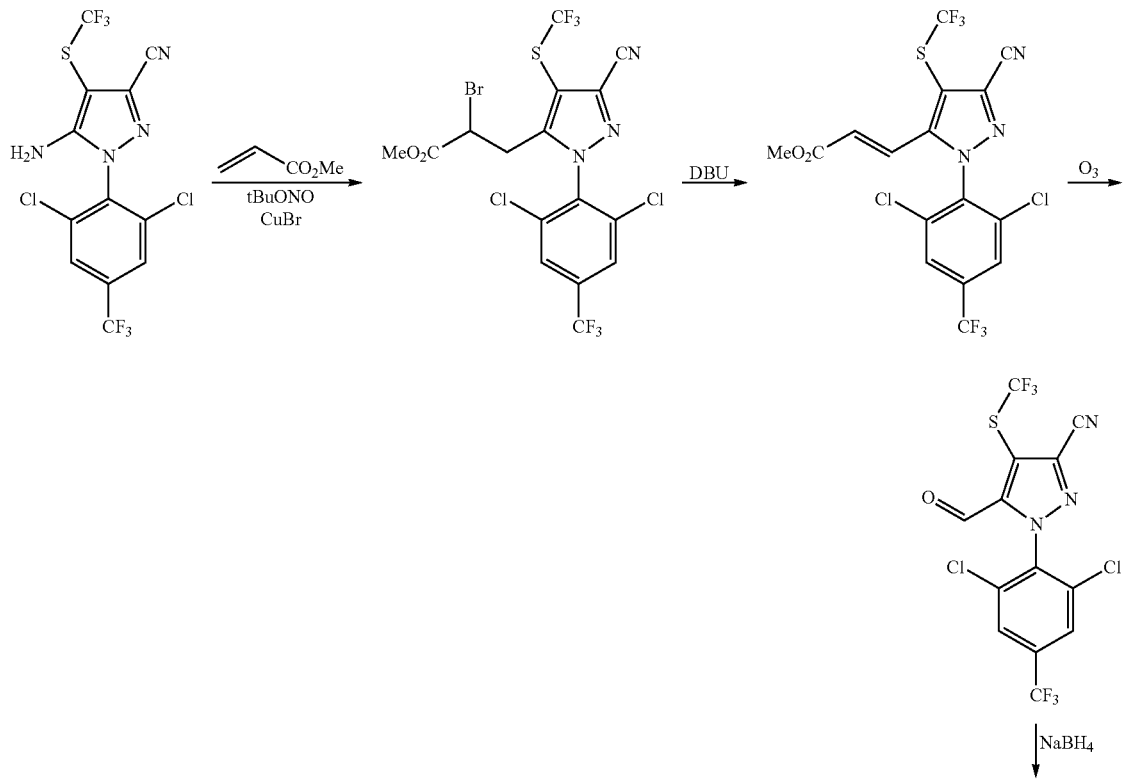

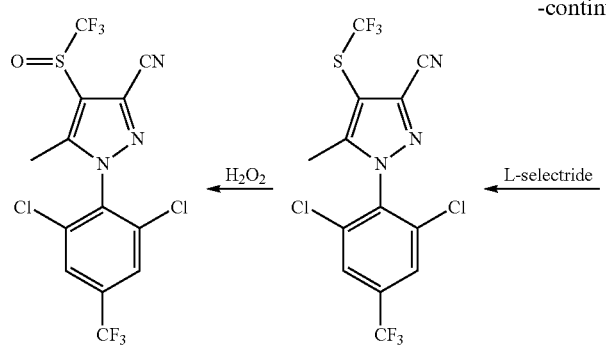
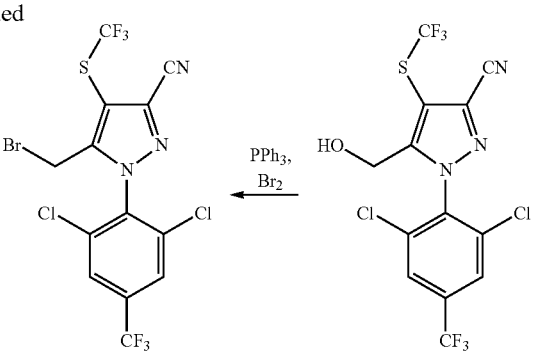

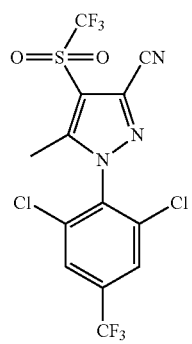

Example 25

Example 29

3-Cyano-1-(2,6-dichloro-4-trifluoromethylphenyl)-5-ethyl-4-trifluoromethylthiopyrazole (compound No 2)

A solution of 3-cyano-1-(2,6-dichloro-4-trifluoromethylphenyl)-5-(2-ethenyl)-4-trifluoromethylthiopyrazole (120 mg) in ethanol with catalytic amount of palladium on charcoal was charged in a steel pressure vessel under a 50 psi hydrogen pressure and heated to 80° C. overnight. After cooling to room temperature the mixture was filtered over Celite, and concentrated under reduced pressure to give a residue that was purified on reverse phase column chromatography to give title compound as a white solid (39 mg, 32%). MS (ES): M/Z [M+H+CH$_3$OH]=466. 1H NMR: (400 MHz, CDCl$_3$): 1.11 (t, 3H), 2.71 (quartet, 2H) and 7.82 (s, 2H). 19F NMR (376 MHz, CDCl$_3$): −43.92 (s, 3F) and −63.68 (s, 3F).

The starting material, 3-cyano-1-(2,6-dichloro-4-trifluoromethylphenyl)-5-(2-ethenyl)-4-trifluoromethylthiopyrazole, was prepared as follows:

a. A dioxane solution of 5-bromo-3-cyano-1-(2,6-dichloro-4-trifluoromethylphenyl)-4-trifluoromethylthiopyrazole (100 mg), prepared as described in EP-A-0 295 117, was transferred via a syringe into a 10 ml sealed Pyrex glass tube previously charged with cesium fluoride (30 mg), tetrakis(triphenylphosphine)palladium (11 mg) and vinyltributyltin (0.07 mL). The glass tube was heated in a microwave for 10 minutes at 180° C. After cooling to room temperature, the mixture was filtered over Celite, diluted with ethyl acetate, washed with water and brine. The organic phase was dried over anhydrous magnesium sulfate, filtered and concentrated under reduced pressure to give a residue that was purified on reverse phase column chromatography to give 3-cyano-1-(2,6-dichloro-4-trifluoromethylphenyl)-5-(2-ethenyl)-4-trifluoromethylthiopyrazole as a white solid (24 mg, 28%). 1H NMR: (400 MHz, DMSO-d$_6$): 5.80-6.02 (m, 2H), 6.54-6.61 (mt, 1H) and 8.39 (s, 2H). 19F NMR (376 MHz, DMSO-d$_6$): −43.65 (s, 3F) and −61.99 (s, 3F).

The reaction scheme below depicts application of this method to prepare the compound described in Example 29:

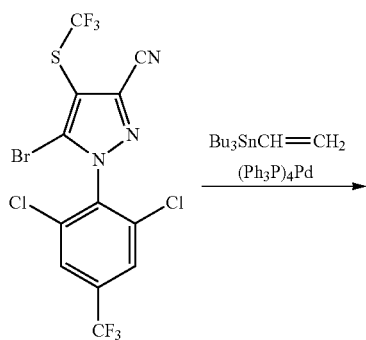

-continued

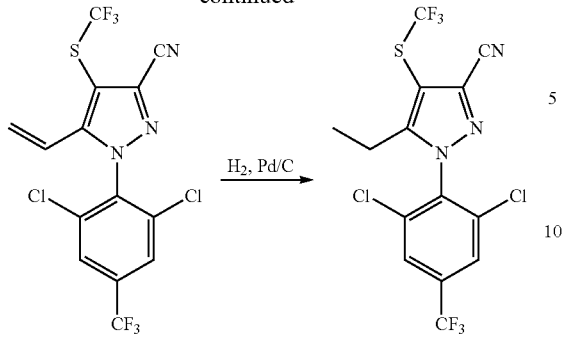

Example 29

Example 30

3-cyano-1-(2,6-dichloro-4-trifluoromethylphenyl)-5-fluoromethyl-4-trifluoromethylthiopyrazole (compound No 3)

Dimethylaminosulfur trifluoride (2.27 mL) was added to a solution of 3-cyano-1-(2,6-dichloro-4-trifluoromethylphenyl)-5-hydroxymethyl-4-trifluoromethylthiopyrazole (2.9 g) in dichloromethane. After stirring for 3 hours, water was added followed by dichloromethane. The organic phase was washed with an aqueous solution of saturated sodium bicarbonate, dried over anhydrous magnesium sulfate, filtered and concentrated under reduced pressure to give a residue that was purified by chromatography ($SiO_2$, heptane/EA) to afford the title compound as a white solid (2.45 g, 84%). 1H NMR: (400 MHz, $CDCl_3$): 5.38 (d, J=47.5 Hz, 2H) and 7.83 (s, 2H). 19F NMR (376 MHz, $CDCl_3$): −43.83 (s, 3F), −63.76 (s, 3F) and −84.12 (t, J=47.5 Hz, 1F).

The starting material, 3-cyano-1-(2,6-dichloro-4-trifluoromethylphenyl)-5-hydroxymethyl-4-trifluoromethylthiopyrazole, was prepared as described below:
   a. A solution of 5-amino-3-cyano-1-(2,6-dichloro-4-trifluoromethylphenyl)-4-trifluoro-methylthiopyrazole (87.5 g), prepared as described in EP-A-0 295 117, was added dropwise to a suspension of tert-butylnitrite (32 mL), methyl acrylate (149 mL) and copper bromide (55.6 g) in acetonitrile. The reaction mixture was stirred overnight. The resulting mixture was diluted with diethylether and washed with water. The organic layer was dried over anhydrous magnesium sulfate, filtered and concentrated under reduced pressure. Trituration of the residue from ethyl acetate and heptane gave 5-(2'-bromo-2'-carbomethoxy)ethyl-3-cyano-1-(2,6-dichloro-4-trifluoromethyl-phenyl)-4-trifluoromethylthiopyrazole as a tanned solid (73.7 g, 78%).
   b. 1,8-diazabicyclo-[5.4.0]-undec-7-ene (4.4 mL) was added to a solution of 5-(2'-bromo-2'-carbomethoxy)ethyl-3-cyano-1-(2,6-dichloro-4-trifluoromethylphenyl)-4-trifluoromethylthiopyrazole (15.1 g) dissolved in toluene. After stirring for 40 minutes, the mixture was diluted with ethyl acetate, washed with water, 10% aqueous hydrochloric acid solution and water. The organic phase was dried over anhydrous magnesium sulfate, filtered and concentrated under reduced pressure to give 3-cyano-1-(2,6-dichloro-4-trifluoromethylphenyl)-5-(E-2-methoxycarbonylethenyl)-4-trifluoromethylthiopyrazole as a white solid (11.0 g 85%).
   c. Ozone was bubbled through a solution of the 3-cyano-1-(2,6-dichloro-4-trifluoromethylphenyl)-5-(E-2-methoxycarbonyl-ethenyl)-4-trifluoromethylthiopyrazole (4.8 g) in dichloromethane and methanol for 3 h at −78° C. After 3 hours the intensely blue solution was decolorized with oxygen gas, and then treated with dimethylsulfide at −78° C. This reaction mixture was allowed to warm to room temperature whereupon the mixture was washed with a 10% aqueous solution of sodium bisulfate. The resulting mixture was extracted with ethyl acetate. The organic layer was dried over anhydrous magnesium sulfate, filtered and concentrated under reduced pressure to give 3-cyano-1-(2,6-dichloro-4-trifluoromethylphenyl)-5-formyl-4-trifluoromethylthiopyrazole as a white solid (4.2 g).
   d. 3-Cyano-1-(2,6-dichloro-4-trifluoromethylphenyl)-5-formyl-4-trifluoromethylthiopyrazole (4.2 g) was dissolved in absolute ethanol and sodium borohydride (0.61 g) added portion wise at 0° C. This reaction mixture was stirred and allowed to warm to room temperature over 2 h whereupon water was added. The resulting mixture was extracted with ethyl acetate. The organic layer was dried over anhydrous magnesium sulfate, filtered and concentrated under reduced pressure to give a residue that was purified by chromatography ($SiO_2$, heptane/EA) to afford 3-cyano-1-(2,6-dichloro-4-trifluoromethylphenyl)-5-hydroxymethyl-4-trifluoromethylthiopyrazole as a white solid (4.03 g, 94%).

Example 31

1-(2-Chloro-6-fluoro-4-trifluoromethylphenyl)-3-cyano-5-fluoromethyl-4-trifluoromethylthiopyrazole (compound No 8)

Using a procedure similar to that described in Example 30, except starting from 1-(2-chloro-6-fluoro-4-trifluoromethylphenyl)-3-cyano-5-hydroxymethyl-4-trifluoromethylthiopyrazole, the title compound was isolated as a white solid. 1H NMR: (400 MHz, DMSO-$d_6$): 5.46-5.67 (m, 2H) and 8.41 (m, 2H). 19F NMR (376 MHz, DMSO-$d_6$): −43.57 (s, 3F), −62.14 (s, 3F), −82.55 (t, J=47 Hz, 1F) and −114.79 (m, 1F).

The starting material, 1-(2-chloro-6-fluoro-4-trifluoromethylphenyl)-3-cyano-5-hydroxymethyl-4-trifluoromethylthiopyrazole, was prepared following a similar procedure to that described in Example 30, steps a, b, c, d from 5-amino-1-(2-chloro-6-fluoro-4-trifluoromethylphenyl)-3-cyano-4-trifluoromethylthiopyrazole, prepared as follows:
   a. N-Chlorosuccinimide (4.1 g) was added to a solution of 2-fluoro-4-trifluoromethylaniline in acetonitrile under nitrogen and the mixture heated to 75° C. over night. The mixture was concentrated, diluted with ether, washed with water, saturated sodium bicarbonate solution and brine. The organic layers were dried over anhydrous magnesium sulfate, filtered and concentrated under reduced pressure to give 2-chloro-6-fluoro-4-trifluoromethylaniline as a liquid (5.9 g). $R_f$=0.6 (2:8 EA/heptane); 1H NMR: (400 MHz, $CDCl_3$) 4.41 (bs, 2H); 7.20 (dd, 1H, J=10.5, 1.5 Hz) and 7.36 (s, 1H). 19F NMR (376 MHz, $CDCl_3$): −130.78 (s, 1F) and −61.98 (s, 3F).
   b. A solution of 2-chloro-6-fluoro-4-trifluoromethylaniline (5 g) in acetic acid was added dropwise to a suspension of nitrosyl sulphuric acid (11.2 g) in acetic acid at 15° C. After stirring for 1 hour, this reaction mixture was added dropwise to a suspension of 1,2-dicyano-3-hydroxyprop-2-ene potassium salt (10 g) and sodium acetate trihydrate (32 g) in a mixture of sodium acetic and water at 7° C. After stirring for 1 hour, this reaction mixture was diluted with water and extracted with dichloromethane. The organic layers were stirred vigorously with a 30% ammonium hydroxide solution for 10 minutes, separated, dried over anhydrous magnesium sulfate, filtered and concentrated under reduced pressure to give a residue that was purified by chromatography ($SiO_2$, heptane/EA) to afford 5-amino-1-(2-chloro-6-fluoro-4-trifluoromethylphenyl)-3-cyanopyrazole as a yellow-orange solid (5.1 g, 71%). $R_f$=0.25 (3:7 EA/heptane); 1H NMR (400 MHz, DMSO-$d_6$): 5.94 (s, 1H), 6.14 (s, 2H) and 8.06-8.10 (m, 2H). 19F NMR (376, DMSO-d$_6$): −61.98 (s, 3F) and −114.38 (s, 1F).

The 1,2-dicyano-3-hydroxyprop-2-ene potassium salt was prepared as follows:

A solution of potassium tert-butoxide (29 g) in tert-butanol was added dropwise to a solution of succinonitrile (20 g) and ethyl formate (22.7 g) in a 5:1 mixture of toluene and tert-butanol at 5° C. After stirring for 6 hours, the solid was filtered off, washed once with ethanol and three times with methyl tert-butyl ether and then dried over night in a vacuum oven at 55° C. to give 1,2-dicyano-3-hydroxyprop-2-ene potassium salt as a tan solid (35 g, 96%).

c. A solution of 5-amino-1-(2-chloro-6-fluoro-4-trifluoromethylphenyl)-3-cyanopyrazole (3 g) in dichloromethane was stirred at 0° C. and treated dropwise with a solution of trifluoromethylsulphenyl chloride (2 g) in dichloromethane during 1 hour. After stirring overnight at room temperature, nitrogen was bubbled trough the solution for 5 minutes. Then the mixture was washed with water, saturated sodium bicarbonate solution and brine. The organic layers were dried over anhydrous magnesium sulfate, filtered and concentrated under reduced pressure to give a residue that was purified by chromatography (SiO$_2$, heptane/EA) to afford 5-amino-1-(2-chloro-6-fluoro-4-trifluoromethylphenyl)-3-cyano-4-trifluoromethylthiopyrazole as a white solid (3.5 g, 86%). R$_f$=0.4 (3:7 EA/heptane); 1H NMR (400 MHz, DMSO-d$_6$) 7.21 (bs, 2H) and 8.10-8.14 (m, 2H). 19F NMR (376 MHz, DMSO-d$_6$): −45.33 (s, 3F), −62.08 (s, 3F) and −114.62 (s, 1F).

Example 32

3-Cyano-1-(2,6-dichloro-4-trifluoromethoxyphenyl)-5-fluoromethyl-4-trifluoromethylthiopyrazole (compound No 16)

Using a procedure similar to that described in Example 30, except starting from 3-cyano-1-(2,6-dichloro-4-trifluoromethoxyphenyl)-5-hydroxymethyl-4-trifluoromethylthiopyrazole, the title compound was isolated as a white solid. MS (ES): M/Z [M+H] 454. 1H NMR: (400 MHz, DMSO-d$_6$): 5.47 (d, J=46 Hz, 2H) and 8.09 (s, 2H). 19F NMR (376 MHz, DMSO-d$_6$): −43.67 (s, 3F), −57.37 (s, 3F) and −82.82 (t, J=45 Hz, 1F).

The starting material, 3-cyano-1-(2,6-dichloro-4-trifluoromethoxyphenyl)-5-hydroxymethyl-4-trifluoromethylthiopyrazole, was prepared following a similar procedure to that described in Example 30, steps a, b, c, d, from 5-amino-3-cyano-1-(2,6-dichloro-4-trifluoromethoxyphenyl)-4-trifluoromethylthiopyrazole that is described in EP-A-0 295 117.

Example 33

1-(2-Chloro-6-fluoro-4-trifluoromethylphenyl)-3-cyano-4-dichlorofluoromethylthio-5-fluoromethylpyrazole (compound No 25)

Using a procedure similar to that described in Example 30, except starting from 1-(2-chloro-6-fluoro-4-trifluoromethylphenyl)-3-cyano-4-dichlorofluoromethylthio-5-hydroxymethylpyrazole, the title compound was isolated as a white solid. 1H NMR: (400 MHz, CDCl$_3$): 5.29-5.54 (m, 2H), 7.57 (dd, J=8, 1.5 Hz, 1H) and 7.74 (bs, 1H). 19F NMR (376 MHz, CDCl$_3$): −21.99 (s, 1F), −37.00 (t, J=47 Hz, 1F), −63.81 (s, 3F) and −113.28 (bs, 1F).

The starting material, 1-(2-chloro-6-fluoro-4-trifluoromethylphenyl)-3-cyano-4-dichlorofluoromethylthio-5-hydroxymethylpyrazole, was prepared following a similar procedure to that described in Example 30, steps a, b, c, d, from 5-amino-1-(2-chloro-6-fluoro-4-trifluoromethylphenyl)-3-cyano-4-dichlorofluoromethylthiopyrazole, prepared as follows:

a. Sulfur monochloride (0.78 g) was added at 10° C. to a dichloromethane solution of 5-amino-1-(2-chloro-6-fluoro-4-trifluoromethylphenyl)-3-cyanopyrazole (3.54 g), described in Example 31 step b. After stirring overnight at room temperature, nitrogen was bubbled trough the solution for 5 minutes. The solid precipitate was filtered, washed with dichloromethane, heptane and dried under reduced pressure to give 5-amino-1-(2-chloro-6-fluoro-4-trifluoromethylphenyl)-3-cyanopyrazol-4-yl disulfide as a pale yellow solid (2.8 g, 72%). R$_f$=0.3 (4:6 EA/heptane)

b. Sodium dithionite (6.2 g), disodium hydrogen phosphate (4.3 g) and fluorotrichloromethane (5.2 g) were added with stirring to a solution of 5-amino-1-(2-chloro-6-fluoro-4-trifluoromethylphenyl)-3-cyanopyrazol-4-yl disulfide (5.15 g) in a 2:1 mixture of N,N-dimethylformamide and water at 15° C. After stirring for one hour, the mixture was poured into ice and stirred for 30 minutes. The solid was filtered off, washed with water and dried to give 5-amino-1-(2-chloro-6-fluoro-4-trifluoromethylphenyl)-3-cyano-4-dichlorofluoromethylthiopyrazole as a white solid (4.1 g, 64%). R$_f$=0.4 (3:7 EA/heptane).

Example 34

3-Cyano-4-dichlorofluoromethylthio-1-(2,6-dichloro-4-trifluoromethoxyphenyl)-5-fluoromethylpyrazole (compound No 21)

Using a procedure similar to that described in Example 30, except starting from 3-cyano-4-dichlorofluoromethylthio-1-(2,6-dichloro-4-trifluoromethoxyphenyl)-5-hydroxymethylpyrazole, the title compound was isolated as a white solid. 1H NMR: (400 MHz, DMSO-d$_6$): 5.59 (d, J=46 Hz, 2H) and 8.10 (s, 2H). 19F NMR (376 MHz, DMSO-d$_6$): −21.31 (s, 1F), −57.36 (s, 3F) and −83.08 (t, J=45 Hz, 1F).

The starting material, 3-cyano-4-dichlorofluoromethylthio-1-(2,6-dichloro-4-trifluoromethoxyphenyl)-5-hydroxymethylpyrazole, was prepared following a similar procedure to that described in Example 30, steps a, b, c, d, from 5-amino-3-cyano-4-dichlorofluoromethylthio-1-(2,6-dichloro-4-trifluoromethoxyphenyl)pyrazole, which was prepared following a similar procedure to that described in Example 33, steps a,b, from 5-amino-3-cyano-1-(2,6-dichloro-4-trifluoromethoxyphenyl)pyrazole that itself was prepared from 2,6-dichloro-4-trifluoromethoxyaniline using a similar procedure to that described in Example 31, steps b,c.

Example 35

3-Cyano-1-(2,6-dichloro-4-pentafluorothiophenyl)-5-fluoromethyl-4-trifluoromethylthiopyrazole (compound No 33)

Using a procedure similar to that described in Example 30, except starting from 3-cyano-1-(2,6-dichloro-4-pentafluorothiophenyl)-5-hydroxymethyl-4-trifluoromethylthiopyrazole, the title compound was isolated as a white solid. 1H NMR: (400 MHz, CDCl$_3$): 5.39 (d, J=47 Hz, 2H) and 7.96 (s, 2H). 19F NMR (376 MHz, CDCl$_3$): −43.76 (s, 3F), 62.68 (d, J=151 Hz, 4F) and 78.84 (quintet, J=150 Hz, 1F).

The starting material, 3-cyano-1-(2,6-dichloro-4-pentafluorothiophenyl)-5-hydroxymethyl-4-trifluoromethylthiopyrazole, was prepared following a similar procedure to that described in Example 30, steps a, b, c, d, from 5-amino-3-cyano-1-(2,6-dichloro-4-pentafluorothiophenyl)-4-trifluoromethylthiopyrazole, prepared from 4-pentafluorothioaniline following a similar procedure to that described in Example 31, steps a, b, c, except that 2.2 equivalents of N-chlorosuccinimide were used in step a.

Example 36

4-Chlorodifluoromethylthio-1-(2-chloro-6-fluoro-4-trifluoromethylphenyl)-3-cyano-5-fluoromethylpyrazole (compound No 35)

Using a procedure similar to that described in Example 30, except starting from 4-chlorodifluoromethylthio-1-(2-chloro-6-fluoro-4-trifluoromethylphenyl)-3-cyano-5-hydroxymethylpyrazole, the title compound was isolated as a white solid. MS (ES): M/Z [M−H] 436. 1H NMR: (400 MHz, CDCl$_3$): 5.29-5.54 (m, 2H), 7.57 (dd, J=8, 3, 1.5 Hz, 1H) and 7.74 (bs, 1H). 19F NMR (376 MHz, CDCl$_3$): −63.83 (s, 3F), −84.17 (t, J=47 Hz, 1F), −113.31 (s, 1F) and −162.04 (s, 2F).

The starting material, 4-chlorodifluoromethylthio-1-(2-chloro-6-fluoro-4-trifluoromethylphenyl)-3-cyano-5-hydroxymethylpyrazole, was prepared following a similar procedure to that described in Example 30, steps a, b, c, d, from 5-amino-4-chlorodifluoromethylthio-1-(2-chloro-6-fluoro-4-trifluoromethylphenyl)-3-cyanopyrazole, prepared following the same procedure to that described in Example 33, steps a,b, except that bromochlorodifluoromethane was used in step b instead of fluorotrichloromethane.

Example 37

3-Cyano-1-(2,6-dichloro-4-trifluoromethylphenyl)-5-fluoromethyl-4-trifluoromethylsulfinylpyrazole (compound No 10)

A 30 wt % aqueous solution of hydrogen peroxide (50 μL) was added to a trifluoroacetic acid solution of 3-cyano-1-(2,6-dichloro-4-trifluoromethylphenyl)-5-fluoromethyl-4-trifluoromethylthiopyrazole (205 mg) prepared as described in Example 30. The reaction mixture was stirred for 6 h whereupon solvent was evaporated under reduced pressure to give a residue that was purified by chromatography (SiO$_2$, heptane/DCM) to afford the title compound as a white solid (66.5 mg, 32%). MS (ES): M/Z [M−H] 452. 1H NMR: (400 MHz, DMSO-d$_6$): 5.48-5.75 (m, 2H) and 8.41 (s, 2H). 19F NMR (376 MHz, DMSO-d$_6$): −62.05 (s, 3F), −73.68 (d, 3F) and −82.41 (m, 1F).

Example 38

1-(2-Chloro-6-fluoro-4-trifluoromethylphenyl)-3-cyano-5-fluoromethyl-4-trifluoromethylsulfinylpyrazole (compound No 11)

Using a procedure similar to that described in Example 37, except starting from 1-(2-chloro-6-fluoro-4-trifluoromethylphenyl)-3-cyano-5-fluoromethyl-4-trifluoromethylthiopyrazole described in Example 31, the title compound was isolated as a white solid. MS (ES): M/Z [M+H] 438. 1H NMR: (400 MHz, DMSO-d$_6$): 5.48-5.77 (m, 2H) and 8.26 (m, 2H). 19F NMR (376 MHz, DMSO-d$_6$): −62.17 (s, 3F), −73.63 (bs, 3F), −82.18 (m, 1F) and −114.50 to −114.84 (m, 1F).

Example 39

3-Cyano-1-(2,6-dichloro-4-trifluoromethoxyphenyl)-5-fluoromethyl-4-trifluoromethylsulfinylpyrazole (compound No 18)

Using a procedure similar to that described in Example 37, except starting from 3-cyano-1-(2,6-dichloro-4-trifluoromethoxyphenyl)-5-fluoromethyl-4-trifluoromethylthiopyrazole described in Example 32, the title compound was isolated as a white solid. MS (ES): M/Z [M+H] 470. 1H NMR: (400 MHz, DMSO-d$_6$): 5.46-5.74 (m, 2H) and 8.10 (m, 2H). 19F NMR (376 MHz, DMSO-d$_6$): −57.37 (s, 3F), −73.72 (s, 3F) and −82.46 (t, J=46 Hz, 1F).

Example 40

3-Cyano-4-dichlorofluoromethylsulfinyl-1-(2,6-dichloro-4-trifluoromethoxyphenyl)-5-fluoromethylpyrazole (compound No 22)

Using a procedure similar to that described in Example 37, except starting from 3-cyano-4-dichlorofluoromethylthio-1-(2,6-dichloro-4-trifluoromethoxyphenyl)-5-fluoromethylpyrazole described in Example 33, the title compound was isolated as a white solid. MS (ES): M/Z [M+NH$_4$] 519. 1H NMR: (400 MHz, CDCl$_3$): 5.50-5.72 (m, 2H) and 7.44 (s, 2H). 19F NMR (376 MHz, CDCl$_3$): −58.25 (s, 3F), −63.63 (s, 1F) and −85.23 (t, 1F).

Example 41

1-(2-Chloro-6-fluoro-4-trifluoromethylphenyl)-3-cyano-4-dichlorofluoromethylsulfinyl-5-fluoromethylpyrazole (compound No 28)

Using a procedure similar to that described in Example 37, except starting from 1-(2-chloro-6-fluoro-4-trifluoromethylphenyl)-3-cyano-4-dichlorofluoromethylthio-5-fluoromethylpyrazole described in Example 34, the title compound was isolated as a white solid. MS (ES): M/Z [M+NH$_4$] 487. 1H NMR: (400 MHz, CDCl$_3$): 5.20-5.87 (m, 2H), 7.58 (d, 1H) and 7.74 (s, 1H). 19F NMR (376 MHz, CDCl$_3$): −63.59 to −63.69 (d, 1F), −63.83 (s, 3F) and −112.95 to −113.38 (m, 1F).

Example 42

4-Chlorodifluoromethylsulfinyl-1-(2-chloro-6-fluoro-4-trifluoromethylphenyl)-3-cyano-5-fluoromethylpyrazole (compound No 38)

Using a procedure similar to that described in Example 37, except starting from 4-chlorodifluoromethylthio-1-(2-chloro-6-fluoro-4-trifluoromethylphenyl)-3-cyano-5-fluoromethylpyrazole described in Example 35, the title compound was isolated as a white solid. MS (ES): M/Z [M+NH$_4$] 471. 1H NMR: (400 MHz, CDCl$_3$): 5.45-5.82 (m, 2H), 7.57 (d, J=8, 2 Hz, 1H) and 7.74 (s, 1H). 19F NMR (376 MHz, CDCl$_3$): −8.59 to −8.91 (m, 1F), −60.81 to −62.41 (m, 2F), −63.84 (s, 3F) and −112.99 to −113.35 (m, 1F).

Example 43

1-(2-chloro-6-fluoro-4-trifluoromethylphenyl)-3-cyano-4-dichlorofluoromethylsulfonyl-5-fluoromethylpyrazole (compound No 32)

Sodium periodate (100 mg) and ruthenium chloride (3 mg) were added to a solution of 1-(2-chloro-6-fluoro-4-trifluoromethylphenyl)-3-cyano-4-dichlorofluoromethylthio-5-fluoromethylpyrazole (100 mg), prepared as described in Example 33, in a mixture of acetonitrile-water (2:1). The reaction mixture was stirred overnight whereupon the mixture was diluted with ethyl acetate and saturated aqueous sodium bicarbonate. The organic extract was separated, filtered over Celite and concentrated under reduced pressure to give the title compound as a white solid. MS (ES): M/Z [M+NH$_4$] 503. 1H NMR: (400 MHz, CDCl$_3$): 5.48-5.77 (m, 2H), 7.60 (dd, J=8.3, 1.4 Hz, 1H) and 7.77 (bs, 1H). 19F NMR (376 MHz, CDCl$_3$): −63.77 (bs, 1F), −63.86 (s, 3F), −87.74 to −87.99 (m, 1F) and −113.09 (m, 1F).

Example 44

4-Chlorodifluoromethylsulfonyl-1-(2-chloro-6-fluoro-4-trifluoromethylphenyl)-3-cyano-5-fluoromethylpyrazole (compound No 40)

Using a procedure similar to that described in Example 43, except starting from 4-chlorodifluoromethylthio-1-(2-chloro-6-fluoro-4-trifluoromethylphenyl)-3-cyano-5-fluoromethylpyrazole described in Example 36, the title compound was isolated as a white solid. MS (ES): M/Z [M+NH$_4$] 487. 1H NMR: (400 MHz, CDCl$_3$): 5.46-5.74 (m, 2H), 7.61 (dd, J=8.3, 1.6 Hz, 1H) and 7.77 (bs, 1H). 19F NMR (376 MHz, CDCl$_3$): −10.69 (t, J=47 Hz, 1F), −63.87 (bs, 3F), −64.56 (s, 2F) and −113.04 (m, 1F).

The reaction scheme below depicts application of the general reaction scheme to synthesize compounds of Examples 30, 37 and 43.

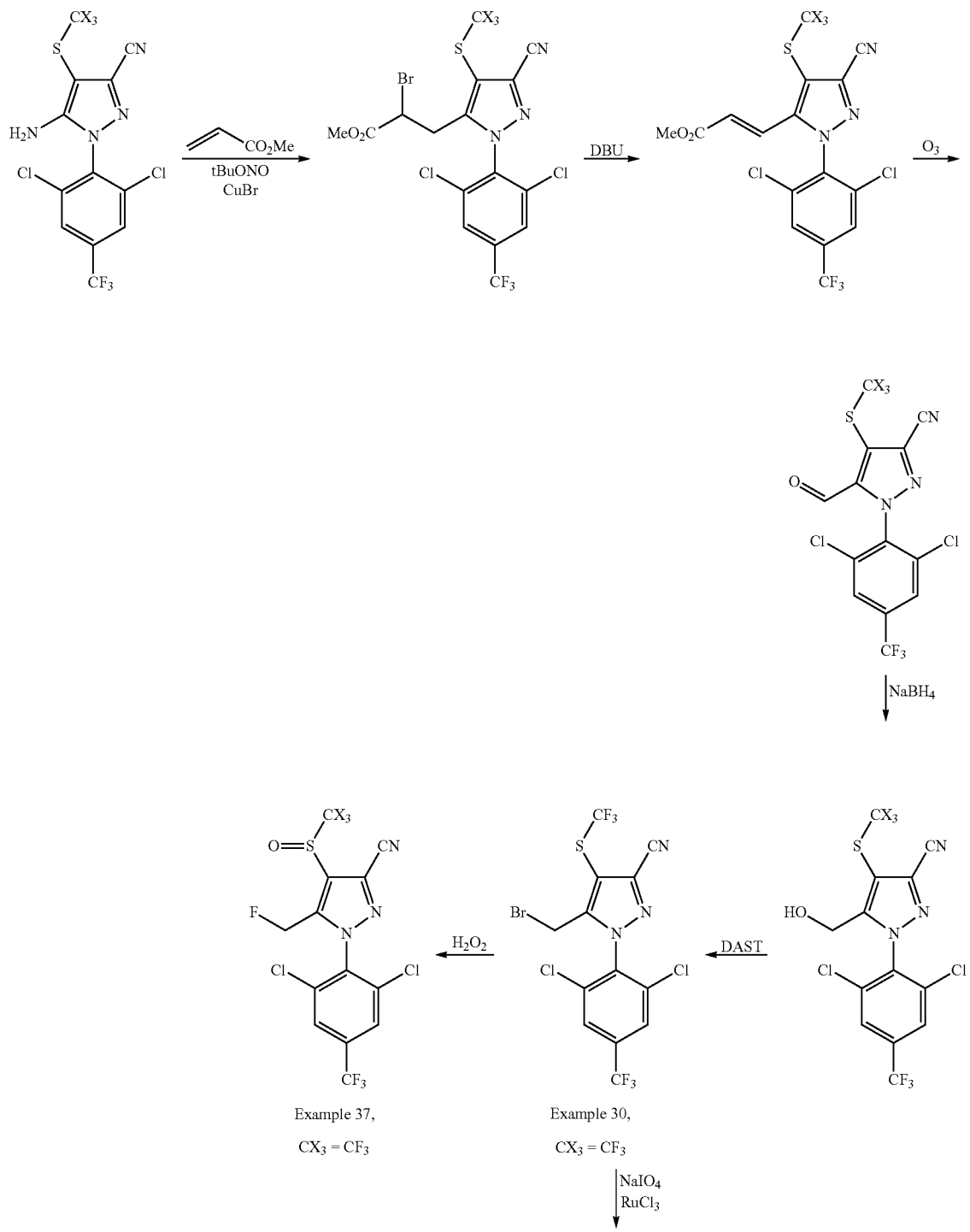

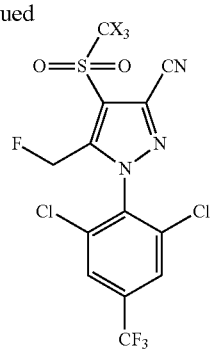

Example 43,

CX₃ = CFCl₂

Example 45

1-(2-Chloro-6-fluoro-4-trifluoromethylphenyl)-3-cyano-4-dichlorofluoromethylthio-5-difluoromethylpyrazole (Compound No 45)

A mixture of 1-(2-chloro-6-fluoro-4-trifluoromethylphenyl)-3-cyano-4-dichlorofluoromethylthio-5-formylpyrazole (450 mg) and [bis(2-methoxyethyl)amino]sulfur trifluoride (660 mg) in dichloromethane was heated to reflux for 6 h, then was cooled to room temperature and evaporated. The residue was purified by chromatography (SiO₂, heptane/DCM) to afford the title compound as a white solid (210 mg, 44%). 1H NMR: (400 MHz, CDCl₃): 6.88 (t, J=51.5 Hz, 1H), 7.55 (dd, J=8.3, 1.6 Hz, 1H), 7.72 (s, 1H). 19F NMR: (376 MHz, CDCl₃): −20.6 (s, 1F), −63.8 (s, 3F), −112.8 (s, 1H), −115.9 to −118.0 (m, 2F).

The starting material, 1-(2-chloro-6-fluoro-4-trifluoromethylphenyl)-3-cyano-4-dichlorofluoromethylthio-5-formylpyrazole, was prepared using a procedure similar to that described in Example 30, parts a, b and c from 5-amino-1-(2-chloro-6-fluoro-4-trifluoromethyl phenyl)-3-cyano-4-trifluoromethylthiopyrazole, prepared as described in Example 31, parts a, b and c.

Example 46

1-(2-Chloro-6-fluoro-4-trifluoromethylphenyl)-3-cyano-4-dichlorofluoromethylsulfinyl-5-difluoromethylpyrazole (Compound No 46)

Using a procedure similar to that described in Example 37, except starting from 1-(2-chloro-6-fluoro-4-trifluoromethylphenyl)-3-cyano-4-dichlorofluoromethylthio-5-difluoromethylpyrazole described in Example 45, the title compound was isolated as a white solid. 1H NMR: (400 MHz, CDCl₃): 7.40 (dd, J=51.9, 8.0 Hz, 1H), 7.56 (dd, J=8, 1.5 Hz, 1H), 7.73 (d, J=1.5 Hz, 1H). 19F NMR: (376 MHz, CDCl₃): −63.3 (d, J=39 Hz, 1F), −63.9 (s, 3F), −112.1 to −112.8 (m, 1F), −116.2 to −116.7 (m, 2F).

The reaction scheme below depicts application of this method to synthesize compounds of Examples 45 and 46:

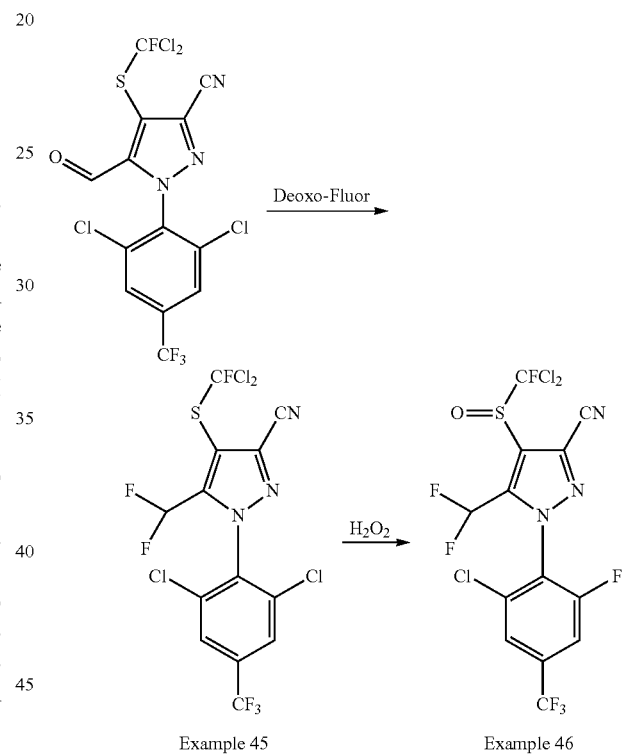

Example 47

1-[3-Chloro-5-(trifluoromethyl)-2-pyridinyl]-3-cyano-4-dichlorofluoromethylthio-5-methylpyrazole (compound 47)

A 30 wt % aqueous ammonium hydroxide solution (50 mL) was added to an ethanol solution (150 mL) of 1-[3-chloro-5-(trifluoromethyl)-2-pyridinyl]-4-dichlorofluoromethylthio-3-ethoxycarbonyl-5-methylpyrazole (9.0 g). After one week stirring at room temperature, solvent was evaporated under reduced pressure to give a solid residue that was dissolved in methanol (40 mL) and treated with more ammonium hydroxide solution (30% aqueous, 12 mL). After 3 days, solvent was partially removed under reduced pressure to give a mixture containing solids that were filtered off. The collected solids were washed with water and dried to give a white solid that was used in the next step without further purification (6.25 g, 74%). Rf=0.2 (3:7 EA/heptane). 1H NMR (400 MHz, CDCl₃): 8.82 (d, J=1.3 Hz, 1H), 8.26 (d, J=2.0 Hz, 1H), 6.80 (br s, 1H), 5.77 (br s, 1H) and 2.46 (s, 3H). 19F NMR (376 MHz, CDCl₃): −62.69 (s, 3F) and −153.47 (s, 1F).

Oxalyl chloride (4.3 mL) was added dropwise to a stirred solution of N,N-dimethylformamide (3.7 mL) in acetonitrile (150 mL) at 0° C. After stirring for 10 minutes, a solution of the above white solid in acetonitrile (60 mL) was added dropwise and the reaction mixture was stirred 1 h. allowing it to warm to room temperature. The reaction mixture was poured rapidly into stirring ice water, stirred 30 minutes and the resulting solid filtered, washed with water and dried to give the title compound as a white solid (5.35 g, 93%). Rf=0.6 (3:7 EA/heptane). MS (ES): M/Z [M+H]=419. 1H NMR (400 MHz, CDCl₃): 8.82 (d, J=1.3 Hz, 1H), 8.28 (d, J=2.0 Hz, 1H) and 2.47 (s, 3H). 19F NMR (376 MHz, CDCl₃): −21.25 (s, 1F) and −62.69 (s, 3F).

The starting material, 1-[3-chloro-5-(trifluoromethyl)-2-pyridinyl]-4-dichlorofluoromethylthio-3-ethoxycarbonyl-5-methyl pyrazole, was prepared as follows:

Potassium carbonate (7.0 g) was added as a solid to a solution of 4-dichlorofluoromethylthio-3-ethoxycarbonyl-5-methyl-1-H-pyrazole (7.25 g) and 2,3-dichloro-5-(trifluoromethyl)pyridine (5.9 g) in dimethoxyethane (100 mL). The mixture was heated to reflux overnight, cooled to room temperature and filtered over a pad of celite. The filtrate was concentrated under reduced pressure to give a residue that was purified by chromatography (SiO₂, heptane/EA) to afford 1-[3-chloro-5-(trifluoromethyl)-2-pyridinyl]-4-dichlorofluoromethylthio-3-ethoxycarbonyl-5-methylpyrazole as a white solid (9.0 g, 76%). Rf=0.8 (1:1 EA/heptane). 1H NMR (400 MHz, CDCl₃): 8.82 (d, 1H), 8.23 (d, J=1.7 Hz, 1H), 4.47 (q, J=7.1 Hz, 2H), 2.45 (s, 3H) and 1.42 (t, J=7.1 Hz, 3H). 19F NMR (376 MHz, CDCl₃): −20.43 (s, 1F) and −62.70 (s, 3F).

Example 48

1-(6-Chloro-4-trifluoromethylpyrid-2-yl)-3-cyano-4-dichlorofluoromethylsulfinyl-5-methylpyrazole (compound No. 48)

A 30 wt % aqueous hydrogen peroxide solution (550 µL) was added to solution of 1-(6-chloro-4-trifluoromethyl-pyrid-2-yl)-3-cyano-5-methyl-4-fluorodichloromethylthiopyrazole (9.0 g) in a trifluoroacetic (15 mL) and dichloromethane (30 mL) and stirred at room temperature overnight. Water was added (50 mL), followed by sodium carbonate till neutral pH was reached. Mixture was extracted with dichloromethane (100 mL). The organic layer was washed with saturated sodium thiosulfate solution and then water, dried over anhydrous sodium sulfate, filtered and concentrated under reduced pressure to give a residue that was purified by chromatography (SiO₂, heptane/EA) to afford 1-(6-chloro-4-trifluoromethylpyrid-2-yl)-3-cyano-4-dichlorofluoromethylsulfinyl-5-methylpyrazole as a white solid (1.15 g, 55%). MS (ES): M/Z [M+NH₄]=452. 1H NMR (400 MHz, CDCl₃): 8.84 (s, 1H), 8.30 (1, 1H) and 2.57 (s, 3H). 19F NMR (376 MHz, CDCl₃): −62.74 (s, 3F) and −62.85 (s, 1F).

Additional 1-aryl-5-alkyl pyrazole and 1-aryl-3,4,5 pyrazole compounds may be prepared by the process of the invention. Example embodiments of the compounds are described in Table 1 below.

TABLE 1

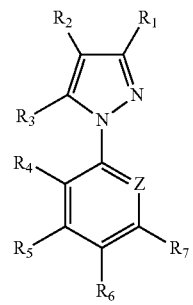

(I)

($R_5 = R_7 = H$; $Z = C—R_{13}$)

| Compound # | $R_1$ | $R_2$ | $R_3$ | $R_4$ | $R_6$ | Z |
|---|---|---|---|---|---|---|
| 1 | CN | SCF₃ | CH₃ | Cl | CF₃ | C—Cl |
| 2 | CN | SCF₃ | CH₂CH₃ | Cl | CF₃ | C—Cl |
| 3 | CN | SCF₃ | CH₂F | Cl | CF₃ | C—Cl |
| 4 | CN | S(O)₂CF₃ | CH₃ | Cl | CF₃ | C—Cl |
| 5 | CN | S(O)CF₃ | CH₃ | Cl | CF₃ | C—Cl |
| 6 | CN | SCF₃ | CH₃ | F | CF₃ | C—F |
| 7 | CN | SCF₃ | CH₃ | Cl | CF₃ | C—F |
| 8 | CN | SCF₃ | CH₂F | Cl | CF₃ | C—F |
| 9 | CN | S(O)CF₃ | CH₃ | Cl | CF₃ | C—F |
| 10 | CN | S(O)CF₃ | CH₂F | Cl | CF₃ | C—Cl |
| 11 | CN | S(O)CF₃ | CH₂F | Cl | CF₃ | C—F |
| 12 | CN | S(O)CF₃ | CH₃ | F | CF₃ | C—F |
| 13 | CN | SCF₃ | CH₃ | H | CF₃ | C—F |
| 14 | CN | S(O)CF₃ | CH₃ | H | CF₃ | C—F |
| 15 | CN | SCCl₂F | CH₃ | Cl | CF₃ | C—Cl |
| 16 | CN | SCF₃ | CH₂F | Cl | OCF₃ | C—Cl |
| 17 | CN | SCF₃ | CH₃ | Cl | OCF₃ | C—Cl |
| 18 | CN | S(O)CF₃ | CH₂F | Cl | OCF₃ | C—Cl |
| 19 | CN | S(O)CF₃ | CH₃ | Cl | OCF₃ | C—Cl |
| 20 | CN | S(O)CCl₂F | CH₃ | Cl | CF₃ | C—Cl |
| 21 | CN | SCCl₂F | CH₂F | Cl | OCF₃ | C—Cl |
| 22 | CN | S(O)CCl₂F | CH₂F | Cl | OCF₃ | C—Cl |
| 23 | CN | SCCl₂F | CH₃ | Cl | OCF₃ | C—Cl |
| 24 | CN | S(O)CCl₂F | CH₃ | Cl | OCF₃ | C—Cl |
| 25 | CN | SCCl₂F | CH₂F | Cl | CF₃ | C—F |
| 26 | CN | SCCl₂F | CH₃ | Cl | CF₃ | C—F |
| 27 | CN | SCCl₂F | CH₃ | H | CF₃ | C—Cl |
| 28 | CN | S(O)CCl₂F | CH₂F | Cl | CF₃ | C—F |
| 29 | CN | S(O)CCl₂F | CH₃ | Cl | CF₃ | C—F |
| 30 | CN | S(O)CCl₂F | CH₃ | H | CF₃ | C—Cl |
| 31 | CN | S(O)₂CCl₂F | CH₃ | Cl | CF₃ | C—F |
| 32 | CN | S(O)₂CCl₂F | CH₂F | Cl | CF₃ | C—F |
| 33 | CN | SCF₃ | CH₂F | Cl | SF₅ | C—Cl |
| 34 | CN | SCF₃ | CH₃ | Cl | SF₅ | C—Cl |
| 35 | CN | SCClF₂ | CH₂F | Cl | CF₃ | C—F |
| 36 | CN | SCClF₂ | CH₃ | Cl | CF₃ | C—F |
| 37 | CN | S(O)CClF₂ | CH₃ | Cl | CF₃ | C—F |
| 38 | CN | S(O)CClF₂ | CH₂F | Cl | CF₃ | C—F |
| 39 | CN | S(O)₂CClF₂ | CH₃ | Cl | CF₃ | C—F |
| 40 | CN | S(O)₂CClF₂ | CH₂F | Cl | CF₃ | C—F |
| 41 | CN | S(O)₂CCl₂F | CH₃ | Cl | CF₃ | C—Cl |
| 42 | CN | SCCl₂F | CH₃ | Cl | SF₅ | C—Cl |
| 43 | CN | SCF₃ | CH₃ | Cl | CF₃ | C—CH₃ |
| 44 | CN | S(O)CF₃ | CH₃ | Cl | CF₃ | C—CH₃ |
| 45 | CN | SCCl₂F | CHF₂ | Cl | CF₃ | C—F |
| 46 | CN | S(O)CCl₂F | CHF₂ | Cl | CF₃ | C—F |
| 47 | CN | SCCl₂F | CH₃ | Cl | CF₃ | N |
| 48 | CN | S(O)CCl₂F | CH₃ | Cl | CF₃ | N |

Method of Use Examples

Method A: Screening Method to Test Contact Activity of Compounds Against Ticks

A solution of the test compound was used to coat the inner wall of glass vials and to treat two filter papers. Once dried, one filter paper was placed in the cap of the vial and the other in the bottom of the vial. Each treated vial was infested with 10 adult *Rhipicephalus sanguineus* (Brown Dog Tick). Contact of the ticks with residues was induced by holding the vials in a controlled environment (24° C., 90-95% relative humidity) and assessment was performed at 24, 48 hours after application in comparison with untreated controls. Compounds numbers 1, 3, 4, 5, 6, 7, 8, 9, 10, 11, 12, 14, 15, 16, 17, 18, 19, 20, 22, 24, 25, 26, 28, 29, 31, 32, 33, 34, 35, 36, 37, 38, 39, 40, 43 and 44 gave at least 80% control of *Rhipicephalus sanguineus* at the 48 hour assessment, at a test concentration of 25 ppm or less; and had $LD_{50}$ values below 6 ppm at the 48 hour assessment.

Method B: Screening Method to Test Contact Activity of Compounds Against Fleas

A solution of the test compound was dispensed, using a pipette, onto filter paper placed into a glass vial. The filter paper was allowed to dry before infesting each vial with 10 adult *Ctenocephalides felis*. The treated *Ctenocephalides felis* were held in a controlled environment (24° C., 90-95% relative humidity) and assessment was performed at 24, 48 and 72 hours after application in comparison with untreated controls. Compounds numbers 1, 6, 7, 15, 20, 21, 23, 25, 26, 28, 29, 31, 32, 33, 34, 35, 36, 37, 39, 40 and 42 gave at least 80% control at 72 hours assessment at a test concentration of 25 ppm or less; and had $LD_{50}$ values below 12 ppm at 72 hours assessment. By way of comparison fipronil (the active ingredient in Frontline®, a known product used to combat fleas), used as a positive control, had an $LD_{50}$ value around 20 ppm at the 72 hour assessment.

Method C: Screening Method to Test Activity of Compounds Against Fleas Following Ingestion.

A cylindrical test container was filled with 10 adult *Ctenocephalides felis*. A cylindrical well was closed on one end with a self-sealing flexible film and placed on top of the test container in such a position that the fleas could pierce the film and feed on the contents of the cylinder. The test compound solution was then pipetted into bovine blood and added to the well. The container part with the *Ctenocephalides felis* was held at 20-22° C. and 40-60% relative humidity while the well part containing the treated blood was held at 37° C. and 40-60% relative humidity. Assessment was performed at 72 hours after application in comparison with untreated controls. Compounds numbers 1, 5, 6, 7, 9, 15, 20, 25, 26, 28, 29, 31, 32, 33, 34, 41 and 42 gave at least 80% control at a test concentration of 2.5 ppm or less; and had an $LD_{50}$ values below 1.5 ppm at the 72 hour assessment.

Method D: Screening Method to Test Activity of Compounds Against *Heliothis virescens*.

Experimental compounds were diluted in acetone. Using a syringe, 1 μl of the test solution was applied to the thorax of susceptible, third instar *Heliothis virescens* larvae. Larvae were then placed on artificial diet and held at 27° C. and 50-70% relative humidity. Mortality was assessed over a five day period. Larvae treated with acetone only served as controls. At the 5 days assessment, compounds numbers 26 and 29 gave at least 50% control of *Heliothis virescens* at a test concentration of 260 μgram active ingredient per gram of insect.

Method E: Screening Method to Test Activity of Compounds Against *Leptinotarsa decemlineata*.

Experimental compounds were diluted in an aqueous formulation containing 5% DMSO and 0.1% Triton X100. Leaf discs with a 3 cm diameter were cut from leaves of *Solanum tuberosum* and dipped in the formulations. After drying, two treated leaf discs were placed into a test plate containing 2% water agar. Discs treated with 5% DMSO, 0.1% Triton X100 served as controls. Ten susceptible adult *Leptinotarsa decemlineata* were then added to each test plate. The test plates were then held at 27° C. for 24 hours during which time the *L. decemlineata* were assessed for knockdown, mortality and leaf consumption. Compounds numbers 26 and 29 gave at least 50% control of *Leptinotarsa decemlineata* at a test concentration of 0.03% active ingredient (w/v).

Method F: Screening Method to Test Activity of Compounds Against *Blattella germanica*.

Experimental compounds were diluted in an aqueous formulation containing 5% DMSO and 0.1% Triton X100 and spread evenly on the inside surface of test plates. After the plates dried, 10 adult male *Blattella germanica* were added to each test plate. After 30 minutes, insects were removed from the treated surface and transferred to a clean plate containing a cotton dental wick saturated with water. Plates were then held at 27° C. for 24 hours during which time the *B. germanica* were observed for knockdown and mortality. Plates treated with 5% DMSO and 0.1% Triton X100 served as controls. Compounds numbers 26 and 29 gave at least 50% control of *Blattella germanica* at a test concentration of 3 μgram active ingredient per $cm^2$.

Method G: Screening Method to Test Activity of Compounds Against *Reticulitermes flavipes* and *Tetramorium caespitum*.

Experimental compounds were diluted in an aqueous formulation containing 5% DMSO and 0.1% Triton X100 and spread evenly on the inside surface of test plates. After the plates dried, 12-15 workers of *Reticulitermes flavipes* or *Tetramorium caespitum* were added to each test plate. After 30 minutes, insects were removed from the treated surface and transferred to a clean plate containing a cotton dental wick saturated with water. Plates were then held at 27° C. for 24 hours during which time the insects were observed for knockdown and mortality. Plates treated with 5% DMSO and 0.1% Triton X100 served as controls. Compounds numbers 26 and 29 gave at least 50% control of *Reticulitermes flavipes* at a test concentration of 3 μgram active ingredient per $cm^2$ and gave at least 50% control of *Tetramorium caespitum* at a test concentration of 0.3 μgram active ingredient per $cm^2$.

Method H: *Phaedon cochleariae* Test (Spray Application)

| Solvent: | 78 parts by weight of acetone |
| --- | --- |
| | 1.5 parts by weight of dimethylformamide |
| Emulsifier: | 0.5 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Chinese cabbage (*Brassica pekinesis*) leaf-disks are sprayed with a preparation of the active ingredient of the desired concentration. Once dry, the leaf disks are infested with mustard beetle larvae (*Phaedon cochleariae*).

After the specified period of time, mortality in % is determined. 100% means that all beetle larvae have been killed and 0% means that none of the beetle larvae have been killed. In this test, for example, compounds 1-32 and 34-46 from the preparation examples showed 80% activity at the concentration of 500 g/ha.

Method I: *Spodoptera frugiperda* Test (Spray Application)

| Solvent: | 78 parts by weight acetone |
| --- | --- |
| | 1.5 parts by weight dimethylformamide |
| Wetting agent | 0.5 parts by weight alkylarylpolyglcolether |

To produce a suitable preparation of the active compound, 1 part by weight of active compound is mixed with the stated amount of solvent and emulsifier, and the concentrate is dilutes with emulsifier-containing water to the desired concentration.

Maize (*Zea mais*) leaf sections are sprayed with a preparation of the active ingredient of the desired concentration. Once dry, the leaf sections are infested with fall armyworm larvae (*Spodoptera frugiperda*).

After the specified period of time, mortality in % is determined. 100% means that all caterpillars have been killed and 0% means that none of the caterpillars have been killed.

In this test, for example, the following compounds from the preparation examples showed ≥80% activity at the concentration of 500 g/ha 5, 10, 15, 20, 22, 23, 24, 27, 28, 30, 34, 42, 46.

Method J: *Myzus persicae* Test (Spray Application)

| Solvent: | 78 parts by weight acetone |
| | 1.5 parts by weight dimethylformamide |
| Wetting agent: | 0.5 parts by weight alkylarylpolyglcolether |

To produce a suitable preparation of active compound, 1 part by weight of active compound is mixed with the stated amount of solvent and emulsifier, and the concentrate is diluted with emulsifier-containing water to the desired concentration.

Chinese cabbage (*Brassica pekinesis*) leaf-disks infected with all instars of the green peach aphid (*Myzus persicae*), are sprayed with a preparation of the active ingredient at the desired concentration.

After the specified period of time, mortality in % is determined. 100% means that all aphids have been killed; 0% means that none of the aphids have been killed.

In this test, for example, the following compounds from the preparation examples showed ≥80% activity at the concentration of 500 g/ha: 1-12, 14, 15-32, 34-40 and 42-46.

Method K: *Tetranychus urticae* Test; OP-Resistant (Spray Application)

| Solvent: | 78 parts by weight acetone |
| | 1.5 parts by weight dimethylformamide |
| Wetting agent: | 0.5 parts by weight alkylarylpolyglcolether |

To produce a suitable preparation of active compound, 1 part by weight of active compound is mixed with the stated amount of solvent and emulsifier, and the concentrate is diluted with emulsifier-containing water to the desired concentration.

French beans (*Phaseolus vulgaris*) which are heavily infested with all stages of the two spotted spidermite (*Tetranychus urticae*), are sprayed with a preparation of the active ingredient at the desired concentration.

After the specified period of time, mortality in % is determined. 100% means that all spider mites have been killed and 0% means that none of the spider mites have been killed.

In this test, for example, the following compounds from the preparation examples showed ≥80% activity at the concentration of 100 g/ha: 14, 20, 24, 25, 26, 27, 28, 29, 30, 31, 32, 34, 37, 38, 39, 40, 42, 46

Method L: *Frankliniella occidentalis* Test (Spray Application)

| Solvent: | 78 parts by weight of acetone |
| | 1.5 parts by weight of dimethylformamide |
| Emulsifier: | 0.5 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

French bean (*Phaseolus vulgaris*) leaf-disks are sprayed with a test solution containing the desired concentration of the active ingredient. Once dry, the leaf disks are infested with western flower thrips (*Frankliniella occidentalis*).

After the specified period of time, mortality in % is determined. 100% means that all the *thrips* have been killed; 0% means that none of the *thrips* have been killed.

In this test, for example, the following compounds from the preparation examples showed ≥80% activity at the concentration of 500 g/ha: 1-10, 12, 16, 19-22, 25, 26, 28, 29, 31, 32, 34-36, 38-40, 42, 44-46.

Method M: *Liriomyza trifolii* Test (Spray Application)

| Solvent: | 78 parts by weight of acetone |
| | 1.5 parts by weight of dimethylformamide |
| Emulsifier: | 0.5 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

French bean (*Phaseolus vulgaris*) leaf-disks infested with larvaes of the am. serpentine leaf miner (*Liriomyza trifolii*) are sprayed with a test solution containing the desired concentration of the active ingredient.

After the specified period of time, mortality in % is determined. 100% means that all the leaf miners have been killed; 0% means that none of the leaf miners have been killed.

In this test, for example, the following compounds from the preparation examples showed ≥80% activity at the concentration of 500 g/ha: 10, 15, 34.

* * *

Having thus described in detail various embodiments of the present invention, it is to be understood that the invention defined by the above paragraphs is not to be limited to particular details set forth in the above description as many apparent variations thereof are possible without departing from the spirit or scope of the present invention.

We claim:

1. A method of controlling ectoparasites in cattle or sheep comprising applying to the back of the cattle or sheep a pour-on skin solution comprising an effective insecticidal amount of a compound of formula (I), wherein $R_5$ and $R_7$ are each hydrogen; and $R_1$, $R_2$, $R_3$, $R_4$, $R_6$ and Z are as defined below for Compound 1 to Compound 48:

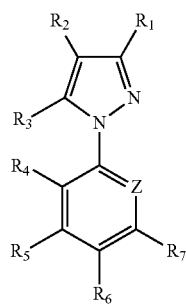

(I)

| Compound # | R₁ | R₂ | R₃ | R₄ | R₆ | Z |
|---|---|---|---|---|---|---|
| 1 | CN | SCF₃ | CH₃ | Cl | CF₃ | C—Cl |
| 2 | CN | SCF₃ | CH₂CH₃ | Cl | CF₃ | C—Cl |
| 3 | CN | SCF₃ | CH₂F | Cl | CF₃ | C—Cl |
| 4 | CN | S(O)₂CF₃ | CH₃ | Cl | CF₃ | C—Cl |
| 5 | CN | S(O)CF₃ | CH₃ | Cl | CF₃ | C—Cl |
| 6 | CN | SCF₃ | CH₃ | F | CF₃ | C—F |
| 7 | CN | SCF₃ | CH₃ | Cl | CF₃ | C—F |
| 8 | CN | SCF₃ | CH₂F | Cl | CF₃ | C—F |
| 9 | CN | S(O)CF₃ | CH₃ | Cl | CF₃ | C—F |
| 10 | CN | S(O)CF₃ | CH₂F | Cl | CF₃ | C—Cl |
| 11 | CN | S(O)CF₃ | CH₂F | Cl | CF₃ | C—F |
| 12 | CN | S(O)CF₃ | CH₃ | F | CF₃ | C—F |
| 13 | CN | SCF₃ | CH₃ | H | CF₃ | C—F |
| 14 | CN | S(O)CF₃ | CH₃ | H | CF₃ | C—F |
| 15 | CN | SCCl₂F | CH₃ | Cl | CF₃ | C—Cl |
| 16 | CN | SCF₃ | CH₂F | Cl | OCF₃ | C—Cl |
| 17 | CN | SCF₃ | CH₃ | Cl | OCF₃ | C—Cl |
| 18 | CN | S(O)CF₃ | CH₂F | Cl | OCF₃ | C—Cl |
| 19 | CN | S(O)CF₃ | CH₃ | Cl | OCF₃ | C—Cl |
| 20 | CN | S(O)CCl₂F | CH₃ | Cl | CF₃ | C—Cl |
| 21 | CN | SCCl₂F | CH₂F | Cl | OCF₃ | C—Cl |
| 22 | CN | S(O)CCl₂F | CH₂F | Cl | OCF₃ | C—Cl |
| 23 | CN | SCCl₂F | CH₃ | Cl | OCF₃ | C—Cl |
| 24 | CN | S(O)CCl₂F | CH₃ | Cl | OCF₃ | C—Cl |
| 25 | CN | SCCl₂F | CH₂F | Cl | CF₃ | C—F |
| 26 | CN | SCCl₂F | CH₃ | Cl | CF₃ | C—F |
| 27 | CN | SCCl₂F | CH₃ | H | CF₃ | C—Cl |
| 28 | CN | S(O)CCl₂F | CH₂F | Cl | CF₃ | C—F |
| 29 | CN | S(O)CCl₂F | CH₃ | Cl | CF₃ | C—F |
| 30 | CN | S(O)CCl₂F | CH₃ | H | CF₃ | C—Cl |
| 31 | CN | S(O)₂CCl₂F | CH₃ | Cl | CF₃ | C—F |
| 32 | CN | S(O)₂CCl₂F | CH₂F | Cl | CF₃ | C—F |
| 33 | CN | SCF₃ | CH₂F | Cl | SF₅ | C—Cl |
| 34 | CN | SCF₃ | CH₃ | Cl | SF₅ | C—Cl |
| 35 | CN | SCClF₂ | CH₂F | Cl | CF₃ | C—F |
| 36 | CN | SCClF₂ | CH₃ | Cl | CF₃ | C—F |
| 37 | CN | S(O)CClF₂ | CH₃ | Cl | CF₃ | C—F |
| 38 | CN | S(O)CClF₂ | CH₂F | Cl | CF₃ | C—F |
| 39 | CN | S(O)₂CClF₂ | CH₃ | Cl | CF₃ | C—F |
| 40 | CN | S(O)₂CClF₂ | CH₂F | Cl | CF₃ | C—F |
| 41 | CN | S(O)₂CCl₂F | CH₃ | Cl | CF₃ | C—Cl |
| 42 | CN | SCCl₂F | CH₃ | Cl | SF₅ | C—Cl |
| 43 | CN | SCF₃ | CH₃ | Cl | CF₃ | C—CH₃ |
| 44 | CN | S(O)CF₃ | CH₃ | Cl | CF₃ | C—CH₃ |
| 45 | CN | SCCl₂F | CHF₂ | Cl | CF₃ | C—F |
| 46 | CN | S(O)CCl₂F | CHF₂ | Cl | CF₃ | C—F |
| 47 | CN | SCCl₂F | CH₃ | Cl | CF₃ | N |
| 48 | CN | S(O)CCl₂F | CH₃ | Cl | CF₃ | N. |

2. A method of claim 1, wherein the compound is Compound 5.

3. A method of claim 1, wherein the ectoparasites are selected from the group consisting of fleas, ticks, mites mosquitoes, flies, lice, blowfly and combinations thereof.

4. A method of claim 1 wherein the method is for controlling *Boophilus microplus* in cattle.

5. A method of claim 1 wherein the method is for controlling ticks in sheep.

6. A method of claim 1, wherein the solution is applied every month or every two months.

7. A method of claim 1 wherein the solution comprises from 0.05 to 10% weight/volume of the compound.

8. A method of claim 1 wherein the solution comprises from 0.1 to 2% weight/volume of the compound.

9. A method of claim 1 wherein the solution comprises from 0.25 to 1.5% weight/volume of the compound.

10. A method of claim 1 wherein the solution comprises about 1% weight/volume of the compound.

11. A method of claim 1 wherein the effective insecticidal amount of the compound is between 0.001 and about 100 mg/kg of the cattle or sheep.

12. The method of claim 1 wherein the effective insecticidal amount of the compound is between 0.001 to about 50 mg/kg of the cattle or sheep.

13. A method of claim 1 wherein the effective insecticidal amount of the compound is about 1 mg/kg of the cattle or sheep.

14. A method of claim 1 wherein the applying of the pour-on skin solution is prior to the cattle or sheep arriving in the feed lot.

15. A method of claim 1 wherein the applying of the pour-on skin solution ceases from between one to two months prior to slaughter.

16. A method of claim 1 wherein the applying of the pour-on skin solution is to the back of the sheep or cattle at one or more points along a line of the back.

17. A method of claim 1 wherein the solution comprises a solvent, a diluent, and optionally an emollient.

18. A method of claim 17, wherein the solvent is selected from the group consisting of:
acetyl tributyl citrate, fatty acid esters, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, N-methylpyrrolidone, diethylene glycol monoethyl ether, ethylene glycol and diethyl phthalate, or a mixture of at least two of these solvents.

19. A method of claim 17 wherein the diluent is selected from the group consisting of: plant oils;
mineral oils aliphatic or cyclic hydrocarbons.

20. A method of claim 17, wherein the emollient is selected from the group of agents:
(a) polyvinylpyrrolidone, polyvinyl alcohols, polyethylene glycols, benzyl alcohol, mannitol, glycerol, sorbitol, polyoxyethylenated sorbitan esters; lecithin, sodium carboxymethylcellulose, silicone oils, polydiorganosiloxane oils,
(b) anionic surfactants such as alkaline stearates, sodium, potassium or ammonium stearates; calcium stearate, triethanolamine stearate; sodium abietate; alkyl sulphates, sodium dodecylbenzenesulphonate, sodium dioctylsulphosuccinate; fatty acids,
(c) cationic surfactants,
(d) amine salts of formula N⁺R'R"R'" in which the radicals R are optionally hydroxylated hydrocarbon radicals; octadecylamine hydrochloride is among the cationic surfactants which can be used,
(e) nonionic surfactants, and
(f) amphoteric surfactants, or
(g) a mixture of at least two of these agents.

* * * * *